（12) United States Patent
Mootha et al.

(10) Patent No.: US 11,987,795 B2
(45) Date of Patent: May 21, 2024

(54) METHODS OF MODULATING SLC7A11 PRE-MRNA TRANSCRIPTS FOR DISEASES AND CONDITIONS ASSOCIATED WITH EXPRESSION OF SLC7A11

(71) Applicants: The Broad Institute, Inc., Cambridge, MA (US); The General Hospital Corporation, Boston, MA (US)

(72) Inventors: Vamsi Krishna Mootha, Cambridge, MA (US); Alexis André Jourdain, Cambridge, MA (US)

(73) Assignees: The Broad Institute, Inc., Cambridge, MA (US); The General Hospital Corporation, Boston, MA (US)

( * ) Notice: Subject to any disclaimer, the term of this patent is extended or adjusted under 35 U.S.C. 154(b) by 44 days.

(21) Appl. No.: 17/482,292

(22) Filed: Sep. 22, 2021

(65) Prior Publication Data

US 2022/0162617 A1    May 26, 2022

Related U.S. Application Data

(60) Provisional application No. 63/117,830, filed on Nov. 24, 2020.

(51) Int. Cl.
    *C07H 21/04*       (2006.01)
    *A61K 31/7088*     (2006.01)
    *C12N 15/113*      (2010.01)

(52) U.S. Cl.
    CPC ...... *C12N 15/1138* (2013.01); *A61K 31/7088* (2013.01)

(58) Field of Classification Search
    None
    See application file for complete search history.

(56) References Cited

U.S. PATENT DOCUMENTS

| | | |
|---|---|---|
| 3,687,808 A | 8/1972 | Merigan, Jr. et al. |
| 5,185,444 A | 2/1993 | Summerton et al. |
| 5,194,599 A | 3/1993 | Froehler et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,527,899 A | 6/1996 | Froehler |
| 5,539,082 A | 7/1996 | Nielsen et al. |
| 5,541,306 A | 7/1996 | Agrawal et al. |
| 5,550,111 A | 8/1996 | Suhadolnik et al. |
| 5,552,540 A | 9/1996 | Haralambidis |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,587,469 A | 12/1996 | Cook et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,633,360 A | 5/1997 | Bischofberger et al. |
| 5,645,985 A | 7/1997 | Froehler et al. |
| 5,646,269 A | 7/1997 | Matteucci et al. |
| 5,663,312 A | 9/1997 | Chaturvedula |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,714,331 A | 2/1998 | Buchardt et al. |
| 5,719,262 A | 2/1998 | Buchardt et al. |
| 5,721,218 A | 2/1998 | Froehler |
| 5,763,588 A | 6/1998 | Matteucci et al. |
| 5,792,608 A | 8/1998 | Swaminathan et al. |
| 5,830,653 A | 11/1998 | Froehler et al. |
| 6,005,096 A | 12/1999 | Matteucci et al. |
| 6,210,892 B1 | 4/2001 | Bennett et al. |
| 7,399,845 B2 | 7/2008 | Seth et al. |
| 7,468,418 B2 | 12/2008 | Iversen et al. |
| 7,737,110 B2 | 6/2010 | Slaugenhaupt et al. |

(Continued)

FOREIGN PATENT DOCUMENTS

| WO | WO-94/29442 A2 | 12/1994 |
|---|---|---|
| WO | WO-96/01313 A1 | 1/1996 |

(Continued)

OTHER PUBLICATIONS

Xu, Xiaotian, et al. "Targeting SLC7A11 specifically suppresses the progression of colorectal cancer stem cells via inducing ferroptosis." European Journal of Pharmaceutical Sciences 152 (2020).*
Jourdain, A., "Pre-mRNA Splicing Control of Mitochondria and Energy Metabolism," Presented on Oct. 28, 2020 at an on-line seminar series called "Webcam" (27 slides).
Jourdain, A. "Pre-mRNA Splicing Control of Mitochondria and Energy Metabolism," Presented on Dec. 10, 2020 at the ASCB-EMBO Cellbio meeting (18 slides).
Acin-Perez et al., "Respiratory Complex III Is Required to Maintain Complex I in Mammalian Mitochondria", Molecular Cell, vol. 13, Mar. 26, 2004, pp. 805-815.
Arensman et al., "Cystine-glutamate antiporter xCT deficiency suppresses tumor growth while preserving antitumor immunity", PNAS, vol. 116, No. 19, May 7, 2019, pp. 9533-9542.

(Continued)

*Primary Examiner* — Kimberly Chong
(74) *Attorney, Agent, or Firm* — Foley & Lardner LLP; Sunit Talapatra

(57) ABSTRACT

Described are methods for enhancing exon skipping in a pre-mRNA of interest, comprising contacting the pre-mRNA with interfering oligonucleotides such as antisense, siRNA, and miRNA. The exon skipping methods are associated with methods of treating a variety of diseases and conditions, including cancer.

12 Claims, 22 Drawing Sheets

Specification includes a Sequence Listing.

(56) References Cited

U.S. PATENT DOCUMENTS

| | | | |
|---|---|---|---|
| 7,879,992 | B2 | 2/2011 | Vickers et al. |
| 7,888,012 | B2 | 2/2011 | Iversen et al. |
| 7,902,160 | B2 | 3/2011 | Matsuo et al. |
| 7,960,541 | B2 | 6/2011 | Wilton et al. |
| 7,973,015 | B2 | 7/2011 | Van Ommen et al. |
| 8,614,095 | B2 | 12/2013 | Radovanovic et al. |
| 10,188,633 | B2 | 1/2019 | Nelson et al. |
| 2004/0224389 | A1 | 11/2004 | Bellgrau et al. |
| 2008/0200409 | A1 | 8/2008 | Wilton et al. |
| 2009/0131624 | A1 | 5/2009 | Reeves et al. |

FOREIGN PATENT DOCUMENTS

| | | | |
|---|---|---|---|
| WO | WO-98/55495 | A2 | 12/1998 |
| WO | WO-2007/146511 | A2 | 12/2007 |
| WO | WO-2009/005793 | A2 | 1/2009 |
| WO | WO-2009/147368 | A1 | 12/2009 |

OTHER PUBLICATIONS

Arroyo et al., "A Genome-wide CRISPR Death Screen Identifies Genes Essential for Oxidative Phosphorylation", Cell Metabolism, vol. 24, Dec. 13, 2016, pp. 875-885.

Ausubel et al., Eds., Current Protocols in Molecular Biology, 1987, Supplement 30, Spring 1995, section 7.7.18, Table 7.7.1, 6 pages.

Badgley et al., "Cysteine depletion induces pancreatic tumor ferroptosis in mice", Science, vol. 368, Apr. 3, 2020, pp. 85-89.

Bao et al., "Mitochondrial dysfunction remodels one-carbon metabolism in human cells", eLife, Jun. 16, 2016, pp. 1-24.

Berg et al., "U1 snRNP Determines mRNA Length and Regulates Isoform Expression", Cell, vol. 150, Jul. 6, 2012, pp. 53-64.

Bonnet et al., "A Mitochondria-K+ Channel Axis is Suppressed in Cancer and Its Normalization Promotes Apoptosis and Inhibits Cancer Growth", Cancer Cell, vol. 11, Jan. 15, 2007, pp. 37-51.

Bray et al., "Near-optimal probabilistic RNA-seq quantification", Nature Biotechnology, vol. 34, No. 5, May 6, 2016, pp. 525-527.

Cai et al., "xCT increases tuberculosis susceptibility by regulating antimicrobial function and inflammation", Oncotarget, vol. 7, No. 21, Apr. 27, 2016, pp. 31001-31013.

Christofk et al., "The M2 splice isoform of pyruvate kinase is important for cancer metabolism and tumour growth," Nature, Mar. 13, 2008, vol. 452, pp. 230-233.

Crabtree, "Observations on the Carbohydrate Metabolism of Tumours", Biochem J., vol. 23, Apr. 22, 1929, pp. 536-545.

De Conti et al., "Exon and intron definition in pre-mRNA splicing", Wires RNA, vol. 4, Jan. / Feb. 2013, pp. 49-60.

De Francisco Amorim et al., "The U1 snRNP Subunit LUC7 Modulates Plant Development and Stress Responses via Regulation of Alternative Splicing", The Plant Cell, vol. 30, Oct. 11, 2018, pp. 2838-2854.

Denti et al., "Long-Term Benefit of Adeno-Associated Virus/ Antisense-Mediated Exon Skipping in Dystrophic Mice", Human Gene Therapy, vol. 19, May 28, 2008, pp. 601-608.

Dephoure et al., "A quantitative atlas of mitotic phosphorylation" PNAS, vol. 105, No. 31, Aug. 5, 2008, pp. 10762-10767.

Ding et al., "Human Papillomavirus Type 16-Immortalized Endocervical Cells Selected for Resistance to Cisplatin are Malignantly Transformed and Have a Multidrug Resistance Phenotype", Int. J. Cancer, vol. 87, No. 6, Apr. 4, 2000, pp. 818-823.

Dobin, et al., "STAR: ultrafast universal RNA-seq aligner", Bioinformatics, vol. 29, No. 1, Oct. 25, 2012, pp. 15-21.

Du et al., "Inhibiting xCT/SLC7A11 induces ferroptosis of myofibroblastic hepatic stellate cells and protects against liver fibrosis", BioRxiv, doi: 10.1101/2019.12.23.886259, Dec. 23, 2019, pp. 1-44.

Eden et al., "GOrilla: a tool for discovery and visualization of enriched GO terms in ranked gene lists", BMC Bioinformatics, vol. 10, Feb. 3, 2009, pp. 1-7.

Englisch et al., "Chemically Modified Oligonucleotides as Probes and Inhibitors", Angewandte Chemie, International Edition, vol. 30, No. 6, Jun. 1991, pp. 613-629.

Fortes et al., "Luc7p, a novel yeast U1 snRNP protein with a role in 5' splice site recognition", Genes & Development, vol. 13, Jul. 23, 1999, pp. 2425-2438.

Friedman et al., "Ab initio identification of functionally interacting pairs of cis-regulatory elements", Genome Research, vol. 18, Sep. 17, 2008, pp. 1643-1651.

Gaffney et al., "A New Strategy for the Protection of Deoxyguanosine During Oligonucleotide Synthesis", Tetrahedron Letters, vol. 23, No. 22, Feb. 11, 1982, pp. 2257-2260.

Gaffney et al., "Synthesis of 0-6-Alkylated Deoxyguanosine Nucleosides", Tetrahedron Letters, vol. 23, No. 22, Feb. 11, 1982, pp. 2253-2256.

Gao et al., "CLUH regulates mitochondrial biogenesis by binding mRNAs of nuclear-encoded mitochondrial proteins", J. Cell Biol., vol. 207, No. 2, Sep. 18, 2014, pp. 213-223.

Gao et al., "Role of RBM25/LUC7L3 in Abnormal Cardiac Sodium Channel Splicing Regulation in Human Heart Failure", Circulation, vol. 124, Sep. 6, 2011, pp. 1124-1131.

Geiger et al., "Initial Quantitative Proteomic Map of 28 Mouse Tissues Using the SILAC Mouse*", Molecular & Cellular Proteomics, vol. 12, No. 6, Feb. 22, 2013, pp. 1709-1722.

GENBANK Accession No. LP899424.1, Sequence 14 from Patent EP3180435, accessed Apr. 20, 2023.

GENPEPT Accession No. 138593, Fibroblast Activation Protein-alpha—Human, accessed Apr. 20, 2023.

Gohil et al., "Nutrient-sensitized screening for drugs that shift energy metabolism from mitochondrial respiration to glycolysis", Nature Biotechnology, vol. 28, No. 3, Feb. 14, 2010, pp. 249-255.

Gossen et al., "Tight control of gene expression in mammalian cells by tetracycline-responsive promoters," Proceedings of the National Academy of Sciences, USA, Jun. 1992, vol. 89, pp. 5547-5551.

Gossen et al., "Transcriptional activation by tetracyclines in mammalian cells" Science, Jun. 23, 1995, vol. 268, No. 5218, pp. 1766-1769.

Gough et al., "The use of barium salts of protected deoxyribonucleoside-3' p-chlorophenyl phosphates for construction of oligonucleotides by the phosphotriester method: high-yield synthesis of dinucleotide blocks", Nucleic Acids Research, vol. 7, No. 7, Sep. 24, 1979, pp. 1955-1964.

Gu et al., "mTORC2 Regulates Amino Acid Metabolism in Cancer by Phosphorylation of the Cystine-Glutamate Antiporter xCT", Molecular Cell, vol. 67, Jul. 6, 2017, pp. 128-138.e7.

Hata et al., "Diphenylcarbamoyl and Propionyl Groups: A New Combination of Protecting Group for the Guanine Residue", Tetrahedron Letters, vol. 24, No. 27, Mar. 19, 1983, pp. 2775-2778.

Hayer et al., "Engulfed cadherin fingers are polarized junctional structures between collectively migrating endothelial cells", Nature Cell Biology, vol. 18, No. 12, Nov. 14, 2016, pp. 1311-1333.

Hermonat et al., "Use of adeno-associated virus as a mammalian DNA cloning vector: Transduction of neomycin resistance into mammalian tissue culture cells", Proceedings of the National Academy of Sciences USA, Oct. 1984, vol. 81, pp. 6466-6470.

Hillen et al., "Mechanisms Underlying Expression of TN10 Encoded Tetracycline Resistance", Annu. Rev. Microbiol., vol. 48, 1994, pp. 345-369.

Hillenmeyer et al., "The Chemical Genomic Portrait of Yeast: Uncovering a Phenotype for All Genes", Science, vol. 320, Apr. 18, 2008, pp. 362-365.

Huang et al., "Regulation of hypoxia-inducible factor 1alpha is mediated by an O2-dependent degradation domain via the ubiquitin-proteasome pathway", Proc. Natl. Acad. Sci. USA, vol. 95, Jul. 1998, pp. 7987-7992.

Huttlin et al., "A Tissue-Specific Atlas of Mouse Protein Phosphorylation and Expression", Cell, vol. 143, Dec. 23, 2010, pp. 1174-1189.

Incitti et al., "Exon Skipping and Duchenne Muscular Dystrophy Therapy: Selection of the Most Active U1 snRNA-Antisense Able to Induce Dystrophin Exon 51 Skipping", Molecular Therapy, vol. 18, No. 9, Jun. 15, 2010, pp. 1675-1682.

(56) References Cited

OTHER PUBLICATIONS

Ito et al., "Metabolic requirements for the maintenance of self-renewing stem cells", Nature Reviews, Molecular Cell Biology, vol. 15, Apr. 2014, pp. 243-256.

Jiang et al., "Ferroptosis as a p53-mediated activity during tumour suppression", Nature, vol. 520, Apr. 2, 2015, pp. 57-62.

Jourdain et al., "GRSF1 Regulates RNA Processing in Mitochondrial RNA Granules", Cell Metabolism, vol. 17, Mar. 5, 2013, pp. 399-410.

Kaleeba et al., "Kaposi's Sarcoma-Associated Herpesvirus Fusion-Entry Receptor: Cystine Transporter xCT", Science, vol. 311, No. 5769, Mar. 31, 2006, pp. 1921-1924.

Kimura et al., "Serine-arginine-rich nuclear protein Luc7I regulates myogenesis in mice", Gene, vol. 341, Sep. 17, 2004, pp. 41-47.

Koppula et al., "The glutamate/cystine antiporter SLC7A11/xCT enhances cancer cell dependency on glucose by exporting glutamate", J. Biol. Chem., vol. 292, No. 34, Jun. 19, 2017, pp. 14240-14249.

Kotini et al., "Functional analysis of a chromosomal deletion associated with myelodysplastic syndromes using isogenic human induced pluripotent stem cells", Nature Biotechnology, vol. 33, No. 6, Mar. 23, 2015, pp. 646-655.

Kroschwitz, "Polynucleotides", The Concise Encyclopedia of Polymer Science and Engineering, John Wiley & Sons, 1990, pp. 858-859.

Lebkowski et al., "Adeno-Associated Virus: a Vector System for Efficient Introduction and Integration of DNA into a Variety of Mammalian Cell Types", Mol. Cell. Biol., Oct. 1988, vol. 8, No. 10, pp. 3988-3996.

Li et al., "CryoEM structure of Saccharomyces cerevisiae U1 snRNP offers insight into alternative splicing", Nature Communications, vol. 8, vol. 1035, Oct. 19, 2017, pp. 1-13.

Li et al., "MAGeCK enables robust identification of essential genes from genome-scale CRISPR/Cas9 knockout screens", Genome Biology, vol. 15, No. 554, Dec. 5, 2014, pp. 1-12.

Lopez-Bigas et al., "Are splicing mutations the most frequent cause of hereditary disease?", FEBS Letters, vol. 579, Mar. 2, 2005, pp. 1900-1903.

Lovci et al., "Rbfox proteins regulate alternative mRNA splicing through evolutionarily conserved RNA bridges", Nature Structural & Molecular Biology, vol. 20, No. 12, Nov. 10, 2013, pp. 1434-1442.

Love et al., "Moderated estimation of fold change and dispersion for RNA-seq data with DESeq2," Genome Biology, vol. 15, No. 550, Dec. 5, 2014, pp. 1-21.

Makarov et al., "Functional mammalian spliceosomal complex E contains SMN complex proteins in addition to U1 and U2 snRNPs", Nucleic Acids Research, vol. 40, No. 6, Nov. 21, 2011, pp. 2639-2652.

Mitsunobu, "The use of diethyl azodicarboxylate and triphenylphosphine in synthesis and transformation of natural products", Synthesis, vol. 1, Jan. 1981, pp. 1-28.

Munoz et al., "Epidemiologic Classification of Human Papillomavirus Types Associated with Cervical Cancer", The New England Journal of Medicine, vol. 348, Feb. 6, 2003, pp. 518-527.

Nielsen et al., "Sequence-selective recognition of DNA by strand displacement with a thymine-substituted polyamide", Science, Dec. 6, 1991, vol. 254, No. 5037, pp. 1497-1500.

Oh et al., "U1 snRNP regulates cancer cell migration and invasion in vitro", Nature Commununications, vol. 11, No. 1, Jan. 7, 2020, pp. 1-8.

Oleinik et al., "Synthesis and Pharmacological Properties of Dantrolene and Sodium Dantrolene", Pharmaceutical Chemistry Journal, vol. 18, No. 5, May 1984, pp. 310-312.

Pasteur, "Animalcules infusoires vivant sans gaz oxygène libre et déterminant des fermentations (Infusorian animalcules living without free oxygen gas and determining fermentations)", Comptes rendus—de l'Académie des Sciences (Reports—Academy of Sciences), vol. 52, Aug. 1, 1861, pp. 344-347.

Pearce et al., "Fueling Immunity: Insights into Metabolism and Lymphocyte Function", Science, vol. 342, Oct. 11, 2013, pp. 1242454-1 to 1242454-11.

Perez-Riverol et al., "The Pride database and related tools and resources in 2019: improving support for quantification data", Nucleic Acids Research, vol. 47, 2019, published online Nov. 5, 2018, pp. D442-D450.

Pfeiffer et al., "Cooperation and Competition in the Evolution of ATP-Producing Pathways", Science, vol. 292, No. 5516, Apr. 20, 2001, pp. 504-507.

Ping et al., "Data Descriptor: Global quantitative analysis of the human brain proteome in Alzheimer's and Parkinson's Disease", Scientific Data, vol. 5, No. 180036, Mar. 13, 2018, pp. 1-12.

Plaschka et al., "Prespliceosome structure provides insights into spliceosome assembly and regulation", Nature, vol. 559, Jul. 19, 2018, pp. 419-422.

Puigserver et al., "A Cold-Inducible Coactivator of Nuclear Receptors Linked to Adaptive Thermogenesis", Cell, vol. 92, Mar. 20, 1998, pp. 829-839.

Reese et al., "The Protection of Thymine and Guanine Residues in Oligodeoxyribonucleotide Synthesis", J. Chem. Soc., Perkin Trans., Jan. 1, 1984, pp. 1263-1270.

Reese et al., "The Protection of Uracil and Guanine Residues in Oligonucleotide Synthesis", Tetrahedron Letters, vol. 22, No. 47, Sep. 10, 1981, pp. 4755-4758.

Reitzer et al., "Evidence That Glutamine, Not Sugar, Is the Major Energy Source for Cultured HeLa Cells*", The Journal of Biological Chemistry, vol. 254, No. 8, Apr. 25, 1979, pp. 2669-2676.

Rino et al., "A Stochastic View of Spliceosome Assembly and Recycling in the Nucleus", PLoS Computational Biology, vol. 3, No. 10, Oct. 2007, pp. 2019-2031.

Robinson et al., "Nonviability of Cells with Oxidative Defects in Galactose Medium: A Screening Test for Affected Patient Fibroblasts", Biochemical Medicine and Metabolic Biology, vol. 48, May 1, 1992, pp. 122-126.

Rossignol et al., "Energy Substrate Modulates Mitochondrial Structure and Oxidative Capacity in Cancer Cells", Cancer Research, vol. 64, Feb. 1, 2004, pp. 985-993.

Sanjana et al., "Improved vectors and genome-wide libraries for CRISPR screening," HHS Public Access Author Manuscript, vol. 11, 2014, pp. 2145-2148.

Sato et al., "Cloning and Expression of a Plasma Membrane Cystine/Glutamate Exchange Transporter Composed of Two Distinct Proteins*", The Journal of Biological Chemistry, vol. 274, No. 17, Apr. 23, 1999, pp. 11455-11458.

Sato et al., "Transcriptional control of cystine/glutamate transporter gene by amino acid deprivation*", Biochemical and Biophysical Research Communications, vol. 325, Sep. 29, 2004, pp. 109-116.

Schlesinger et al., "Alphavirus vectors for gene expression and vaccines", Curr. Opin. Biotechnol., Oct. 1999, vol. 5, pp. 434-439.

Shen et al., "rMATS: Robust and flexible detection of differential alternative splicing from replicate RNA-Seq data", PNAS, vol. 111, Dec. 5, 2014, pp. E5593-E5601.

Shin et al., "The glutamate/cystine xCT antiporter antagonizes glutamine metabolism and reduces nutrient flexibility", Nature Communications, vol. 8, No. 15074, Apr. 21, 2017, pp. 1-11.

Shuai et al., "The U1 spliceosomal RNA is recurrently mutated in multiple cancers", Nature, vol. 574, Oct. 9, 2019, pp. 712-716.

Singh et al., "Pre-mRNA splicing in disease and therapeutics", Trends in Molecular Medicine, vol. 18, No. 8, Aug. 2012, pp. 472-482.

Singh et al., "Putative RNA-splicing gene LUC7L2 on 7q34 represents a candidate gene in pathogenesis of myeloid malignancies", Blood Cancer Journal, vol. 3, No. e117, May 24, 2013, pp. 1-3.

Spellman et al., "Crossregulation and Functional Redundancy between the Splicing Regulator PTB and Its Paralogs nPTB and ROD1", Molecular Cell, vol. 27, Aug. 3, 2007, pp. 420-434.

Sprimont et al., "xCT/Slc7a11 deletion accelerates motor recovery and improves histological outcomes following cervial spinal contusion in mice", Front. Neurosci. Conference Abstract: Belgian Brain Congress 2018—Belgian Brain Council, 2018, Doi:10.3389/conf.fnins.2018.95.00035, 1 page.

(56) References Cited

OTHER PUBLICATIONS

Summerton et al., "Morpholino Antisense Oligomers: Design, Preparation, and Properties," Antisense Nucleic Acid Drug Dev. vol. 7, No. 3, Jun. 1997, pp. 187-195.
Suzuki et al., "Recurrent noncoding U1-snRNA mutations drive cryptic splicing in Shh medulloblastoma", Nature, vol. 574, Oct. 9, 2019, pp. 707-735.
Tarui et al., "Phosphofructokinase Deficiency in Skeletal Muscle. A New Type of Glycogenosis", Biochemical and Biophysical Research Communications, vol. 19, No. 4, Apr. 1, 1965, pp. 517-523.
To et al., "A Compendium of Genetic Modifiers of Mitochondrial Dysfunction Reveals Intra-organelle Buffering", Cell, vol. 179, Nov. 14, 2019, pp. 1222-1238.e17.
Tufarelli et al., "Characterization of a Widely Expressed Gene (LUC7-LIKE; LUC7L) Defining the Centromeric Boundary of the Human alpha-Globin domain", Genomics, vol. 71, No. 3, Feb. 1, 2001, pp. 307-314.
Tyynismaa et al., "Mitochondrial myopathy induces a starvation-like response", Human Molecular Genetics, vol. 19, No. 20, Jul. 23, 2010, pp. 3948-3958.
Ubaida-Mohien et al., "Discovery proteomics in aging human skeletal muscle finds change in spliceosome, immunity, proteostasis and mitochondria", eLife, Oct. 23, 2019, pp. 1-27.
Van Nostrand et al., "Robust transcriptome-wide discovery of RNA-binding protein binding sites with enhanced CLIP (eCLIP)", Nature Methods, vol. 13, No. 6, Jun. 2016, pp. 508-514.
Van Nostrand et al., "Robust, Cost-Effective Profiling of RNA Binding Protein Targets with Single-end Enhanced Crosslinking and Immunoprecipitation (seCLIP)", mRNA Processing: Methods and Protocols, Methods in Molecular Biology, vol. 1648, 2017, pp. 177-200.
Vandersluis et al., "Broad metabolic sensitivity profiling of a prototrophic yeast deletion collection", Genome Biology, vol. 15, No. R64, Apr. 10, 2014, pp. 1-18.

Verma et al., "Modified Oligonucleotides: Synthesis and Strategy for Users", Annu. Rev. Biochem., vol. 67, 1998, pp. 99-134.
Visanji et al., "Effect of Ser-129 Phosphorylation on Interaction of alpha-Synuclein with Synaptic and Cellular Membranes", Journal of Biological Chemistry, vol. 286, No. 41, Oct. 14, 2011 (Withdrawn Aug. 25, 2020), pp. 35863-35873.
Vives-Corrons et al., "First description of phosphofructokinase deficiency in spain: identification of a novel homozygous missense mutation in the PFKM gene", Frontiers in Physiology, vol. 4, No. 393, Dec. 30, 2013, pp. 1-6.
Walboomers et al., "Human Papillomavirus is a Necessary Cause of Invasive Cervical Cancer Worldwide", Journal of Pathology, vol. 189, No. 1, May 11, 1999, pp. 12-19.
Wang et al., "Splicing in disease: disruption of the splicing code and the decoding machinery", Nature Reviews Genetics, vol. 8, Aug. 29, 2007, pp. 749-761.
Warburg, "Über den Stoffwechsel der Carcinomzelle (About the metabolism of the carcinoma cell)", Naturwissenschaften (Natural Sciences), vol. 12, Dec. 1924, pp. 1131-1137.
Webby et al., "Jmjd6 Catalyses Lysyl-Hydroxylation of U2AF65, a Protein Associated with RNA Splicing", Science, vol. 325, Jul. 3, 2009, pp. 90-93.
Wold et al., "Adenovirus Vectors for Gene Therapy, Vaccination and Cancer Gene Therapy," Current Gene Therapy, vol. 13, No. 6, Dec. 2013, pp. 421-433.
Yin et al., "Tetracycline-Controlled Gene Expression System Achieves High-Level and Quantitative Control of Gene Expression", Analytical Biochemistry, vol. 235, No. 0112, 1996, pp. 195-201.
Yin et al., "U1 snRNP regulates chromatin retention of noncoding RNAs", Nature, vol. 580, Apr. 2, 2020, pp. 147-150.
Ying et al., "Cancer therapy using a self-replicating RNA vaccine", Nat. Med., Jul. 1999, vol. 5, No. 7, pp. 823-827.
Zhang et al., "Disease-associated mutation in SRSF2 misregulates splicing by altering RNA-binding affinities", PNAS, vol. 112, Aug. 10, 2015, pp. E4726-E4734.

\* cited by examiner

FIG. 4 (Cont.)

E
mRNAs bound by LUC7L2
(eCLIP)

HeLa          K562

2981   2614   764

METHODS OF MODULATING SLC7A11 PRE-MRNA TRANSCRIPTS FOR DISEASES AND CONDITIONS ASSOCIATED WITH EXPRESSION OF SLC7A11

CROSS REFERENCE TO RELATED APPLICATIONS

This application claims benefit of U.S. Provisional Application No. 63/117,830, filed Nov. 24, 2020, the disclosure of which is incorporated by reference herein in its entirety

STATEMENT OF GOVERNMENT SUPPORT

This invention was made with government support under the Grant No. R35GM122455 awarded by the National Institutes of Health. The government has certain rights to the invention.

FIELD

The subject matter of the present disclosure is generally drawn to methods of utilizing exon skipping as a means to downregulate expression of the human gene SLC7A11, a cystine/glutamate antiporter as a means to treat a variety of diseases and conditions, including cancer.

STATEMENT REGARDING SEQUENCE LISTING

The sequence listing associated with this application is provided in text format in lieu of a paper copy, and is hereby incorporated by reference into the specification. The name of the text file containing the sequence listing is 114203-5891_Sequence_Listing.txt. The text file is 28,426 bytes in size, was created on Nov. 30, 2021, and is being submitted electronically via EFS-Web.

BACKGROUND

Antisense technologies are being developed using a range of chemistries to affect gene expression at a variety of different levels (transcription, splicing, stability, translation). Much of that research has focused on the use of antisense compounds to correct or compensate for abnormal or disease-associated genes in a wide range of indications. Antisense molecules are able to inhibit gene expression with specificity, and because of this, many research efforts concerning oligomers as modulators of gene expression have focused on inhibiting the expression of targeted genes or the function of cis-acting elements. The antisense oligomers are typically directed against RNA, either the sense strand (e.g., mRNA), or minus-strand in the case of some viral RNA targets. In some instances, the antisense oligomers can be directed against pre-mRNA to direct or control the splicing that occurs during the formation of the mRNA.

To achieve a desired effect of specific gene down-regulation, the oligomers generally either promote the decay of the targeted mRNA, block translation of the mRNA or block the function of cis-acting RNA elements, thereby effectively preventing either de novo synthesis of the target protein or replication of the viral RNA.

In a variety of genetic diseases, the effects of mutations on the eventual expression of a gene can be modulated through a process of targeted exon skipping during the splicing process. The splicing process is directed by complex multi-component machinery that brings adjacent exon-intron junctions in pre-mRNA into close proximity and performs cleavage of phosphodiester bonds at the ends of the introns with their subsequent reformation between exons that are to be spliced together. This complex and highly precise process is mediated by sequence motifs in the pre-mRNA that are relatively short, semi-conserved RNA segments to which various nuclear splicing factors that are then involved in the splicing reactions bind. By changing the way the splicing machinery reads or recognizes the motifs involved in pre-mRNA processing, it is possible to create differentially spliced mRNA molecules. It has now been recognized that the majority of human genes are alternatively spliced during normal gene expression, although the mechanisms involved have not been identified. Bennett et al. (U.S. Pat. No. 6,210,892) describe antisense modulation of wild-type cellular mRNA processing using antisense oligomer analogs that do not induce RNAse H-mediated cleavage of the target RNA. This finds utility in being able to generate alternatively spliced mRNAs that lack specific exons (e.g., as described by (Sazani, Kole, et al. 2007) for the generation of soluble TNF superfamily receptors that lack exons encoding membrane spanning domains.

The process of targeted exon skipping is likely to be particularly useful in long genes where there are many exons and introns, where there is redundancy in the genetic constitution of the exons or where a protein is able to function without one or more particular exons. Efforts to redirect gene processing for the treatment of genetic diseases associated with truncations caused by mutations in various genes have focused on the use of antisense oligomers that either: (1) fully or partially overlap with the elements involved in the splicing process; or (2) bind to the pre-mRNA at a position sufficiently close to the element to disrupt the binding and function of the splicing factors that would normally mediate a particular splicing reaction which occurs at that element.

The aim of the present disclosure is to identify targets that are capable of being modified at the pre-mRNA or mRNA level with exon skipping that results in a downstream effect on cancers and other diseases and conditions.

SUMMARY OF THE DISCLOSURE

This present disclosure is generally drawn to methods of utilizing exon skipping in SLC7A11, a cystine/glutamate antiporter, to target SLC7A11 to mitigate a variety of diseases and conditions, such as cancer.

In some aspects, the present disclosure is drawn to a method of inducing exon skipping during splicing of pre-mRNA of human gene SLC7A11 to form mRNA, the method comprising contacting the SLC7A11 pre-mRNA sequence comprising exons 1-12 with an antisense oligonucleotide sequence comprising at least 8 consecutive nucleotides selected from SEQ ID NO:2, wherein exon 7 is absent from the mRNA.

In some aspects, the antisense oligonucleotide sequence comprises at least 15 consecutive nucleotides selected from SEQ ID NO:2. In some aspects, the antisense oligonucleotide sequence is complementary to the pre-mRNA sequence over all but 1 nucleotide. In some aspects, the antisense oligonucleotide sequence comprises 20 nucleotides and is complementary to the pre-mRNA sequence over all but 2 nucleotides. In some aspects, the antisense oligonucleotide sequence comprises 25 nucleotides and is complementary to the pre-mRNA sequence over all but 3 nucleotides. In some aspects, the antisense oligonucleotide sequence comprises 30 nucleotides and is complementary to the pre-mRNA sequence over all but 4 nucleotides. In some aspects, the antisense oligonucleotide sequence comprises 35 nucleotides and is complementary to the pre-mRNA sequence over all but 5 nucleotides.

In some aspects, the antisense oligonucleotide sequence comprises a sequence selected from one of SEQ ID NO:1-11. In some aspects, the antisense oligonucleotide sequence binds the pre-mRNA at a region comprising at least the 3' terminal nucleotide of exon 7 and at least the 5'terminal nucleotide of the flanking intron.

In some aspects, the present disclosure is drawn to a method of inducing exon skipping during splicing of pre-mRNA of human gene SLC7A11 to form mRNA, the method comprising contacting the SLC7A11 pre-mRNA comprising exons 1-12 with an antisense oligonucleotide sequence comprising at least 8 consecutive nucleotides selected from SEQ ID NO:13, wherein exon 9 is absent from the mRNA.

In some aspects, the antisense oligonucleotide sequence comprises at least 15 consecutive nucleotides selected from SEQ ID NO:13. In some aspects, the antisense oligonucleotide sequence is complementary to the pre-mRNA sequence over all but 1 nucleotide. In some aspects, the antisense oligonucleotide sequence comprises 20 nucleotides and is complementary to the pre-mRNA sequence over all but 2 nucleotides. In some aspects, the antisense oligonucleotide sequence comprises 25 nucleotides and is complementary to the pre-mRNA sequence over all but 3 nucleotides. In some aspects, the antisense oligonucleotide sequence comprises 30 nucleotides and is complementary to the pre-mRNA sequence over all but 4 nucleotides. In some aspects, the antisense oligonucleotide sequence comprises 35 nucleotides and is complementary to the pre-mRNA sequence over all but 5 nucleotides.

In some aspects, the antisense oligonucleotide sequence comprises a sequence selected from one of SEQ ID NO:1-11. In some aspects, the antisense oligonucleotide sequence binds the pre-mRNA at a region comprising at least the 3' terminal nucleotide of exon 9 and at least the 5' terminal nucleotide of the flanking intron.

In some aspects, the present disclosure is drawn to a method of inducing exon skipping during splicing of pre-mRNA of human gene SLC7A11 to form mRNA, the method comprising contacting the SLC7A11 pre-mRNA comprising exons 1-12 with: (a) a first antisense oligonucleotide sequence comprising at least 8 consecutive nucleotides selected from SEQ ID NO:2, and (b) a second antisense oligonucleotide sequence comprising at least 8 consecutive nucleotides selected from SEQ ID NO:13; wherein exons 7 and 9 are absent from the mRNA. In some aspects, the mRNA is subjected to nonsense-mediated decay.

In some aspects, the mRNA is translated to a protein deficient for cystine/glutamate antiporter activity, as compared to a protein translated from the mRNA comprising exons 1-12. In some aspects, the method is carried out in vitro. In some aspects, the method is carried out in vivo.

In some aspects, the present disclosure is drawn to a method of treating a cancer expressing a gene product of SLC7A11, a functional cystine/glutamate antiporter, the method comprising administering to a subject having the cancer a therapeutically effective amount of a composition comprising: (a) an antisense oligonucleotide sequence comprising at least 8 consecutive nucleotides selected from SEQ ID NO:2, and/or (b) an antisense oligonucleotide sequence comprising at least 8 consecutive nucleotides selected from SEQ ID NO:13; wherein the cancer exhibits a decrease in the expression of the functional cystine/glutamate antiporter or the expressed antiporter lacks antiporter activity.

In some aspects, the cancer is selected from the group consisting of lung cancer, colorectal cancer, pancreatic cancer, skin cancer, bladder cancer, brain cancer, liver cancer, breast cancer, prostate cancer, and hematological cancer.

In some aspects, the present disclosure is drawn to a method of reducing proliferation of one or more cancer cells characterized by expressing a gene product of SLC7A11, a functional cystine/glutamate antiporter, the method comprising administering to the one or more cancer cells a therapeutically effective amount of a composition comprising: (a) an antisense oligonucleotide sequence comprising at least 8 consecutive nucleotides selected from SEQ ID NO:2, and/or (b) an antisense oligonucleotide sequence comprising at least 8 consecutive nucleotides selected from SEQ ID NO:13; wherein the one or more cancer cells exhibit a decrease in the expression of the functional cystine/glutamate antiporter or the expressed antiporter lacks antiporter activity.

In some aspects, the one or more cancer cells are selected from the group consisting of lung cancer cells, colorectal cancer cells, pancreatic cancer cells, skin cancer cells, bladder cancer cells, brain cancer cells, liver cancer cells, breast cancer cells, prostate cancer cells, and hematological cancer cells. In some aspects, the one or more cancer cells exhibit an increase in the accumulation of reactive oxygen species after administration of the composition. In some aspects, the accumulation of reactive oxygen species results in senescence of the one or more cancer cells.

In some aspects, the present disclosure is drawn to a method of treating or suppressing cancer in a subject, the method comprising administering to the subject having the cancer an effective amount of one or more oligonucleotides comprising at least 8 nucleotides able to hybridize to and form a stable duplex with at least 8 consecutive nucleotides of SEQ ID NOs: 27 or 28; wherein the cancer expresses a gene product of SLC7A11, a functional cystine/glutamate antiporter.

In some aspects, the one or more oligonucleotides comprise at least 15 nucleotides and are able to hybridize to and form a stable duplex with at least 15 consecutive nucleotides of SEQ ID NOs: 27 or 28. In some aspects, the one or more oligonucleotides comprise at least 25 nucleotides and are able to hybridize to and form a stable duplex with at least 25 consecutive nucleotides of SEQ ID NOs: 27 or 28.

In some aspects, the present disclosure is drawn to an antisense oligonucleotide sequence selected from one of SEQ ID NOs:1-22. In some aspects, the present disclosure is drawn to a non-naturally occurring antisense oligonucleotide sequence selected from one of SEQ ID NOs:1-22.

In some aspects, the present disclosure is drawn to a pharmaceutical composition comprising the antisense oligonucleotide according to claim 33 or 34. In some aspects, the pharmaceutical composition according to claim 35, further comprising a pharmaceutically acceptable carrier.

In some aspects, the present disclosure is drawn to a method of administering an antisense molecule, the method comprising administering the antisense oligonucleotide sequence according to claim 33, to one or more cells expressing a gene product of SLC7A11, wherein the gene product exhibits cystine/glutamate antiporter activity.

In some aspects, the present disclosure is drawn to a cell comprising the antisense oligonucleotide sequence according to the present disclosure. In some aspects, the present disclosure is drawn to a vector comprising the antisense oligonucleotide sequence according to the present disclosure.

In some aspects, the vector is an expression vector. In some aspects, the cell comprises the vector. In some aspects, a liposome comprises the antisense oligonucleotide sequence according to claim 33 or 34. In some aspects, the liposome exhibits a negative charge. In some aspects, the liposome exhibits a neutral charge.

In some aspects, the present disclosure is drawn to a method of administering an antisense molecule, the method comprising administering the liposome described herein, to one or more cells expressing a gene product of SLC7A11, wherein the gene product exhibits cystine/glutamate antiporter activity.

In some aspects, the present disclosure is drawn to a method for inducing exon skipping during splicing of pre-mRNA of human gene SLC7A11 to form mRNA, the method comprising contacting the SLC7A11 pre-mRNA comprising exons 1-12 with: (a) a first RNAi oligonucleotide sequence comprising at least 15 consecutive nucleotides selected from SEQ ID NO:2, and/or (b) a second RNAi oligonucleotide sequence comprising at least 15 consecutive nucleotides selected from SEQ ID NO:13; wherein exons 7 and 9 are absent from the mRNA.

In some aspects, the mRNA is translated to a protein deficient for cystine/glutamate antiporter activity, as compared to a protein translated from the mRNA comprising exons 1-12.

In some aspects, the present disclosure is drawn to a method for treating a cancer expressing a gene product of SLC7A11, a functional cystine/glutamate antiporter, the method comprising administering to a subject having the cancer a therapeutically effective amount of a composition comprising: (a) a first RNAi oligonucleotide sequence comprising at least 15 consecutive nucleotides and capable of hybridizing to a sequence of SEQ ID NO:27, and/or (b) a second RNAi oligonucleotide sequence comprising at least 15 consecutive nucleotides and capable of hybridizing to a sequence of SEQ ID NO:28; wherein the cancer exhibits a decrease in the expression of the functional cystine/glutamate antiporter or the expressed antiporter lacks antiporter activity.

In some aspects, the present disclosure is drawn to an RNAi oligonucleotide sequence able to hybridize to a mRNA sequence comprising SEQ ID NO:27 or SEQ ID NO:28. In some aspects, the RNAi oligonucleotide sequence according to the present disclosure comprises at least 15 nucleotides. In some aspects, the RNAi oligonucleotide sequence according to the present disclosure comprises at least 20 nucleotides. In some aspects, the RNAi oligonucleotide sequence according to the present disclosure comprises at least 23 nucleotides. In some aspects, the RNAi oligonucleotide sequence according to the present disclosure comprises at least 25 nucleotides. In some aspects, the RNAi oligonucleotide sequence according to the present disclosure comprises at least 30 nucleotides. In some aspects, the RNAi oligonucleotide sequence according to the present disclosure comprises between 15 and 30 nucleotides. In some aspects, the RNAi oligonucleotide sequence according to the present disclosure comprises between 19 and 25 nucleotides.

In some aspects, the RNAi oligonucleotide sequence according to the present disclosure comprises a small interfering RNA (siRNA). In some aspects, the RNAi oligonucleotide sequence according to the present disclosure comprises a microRNA (miRNA). In some aspects, the present disclosure is drawn to a pharmaceutical composition comprising the RNAi oligonucleotide sequence disclosed herein.

In some aspects, the present disclosure is drawn to a method of administering an RNAi oligonucleotide sequence, the method comprising administering the RNAi disclosed herein, to one or more cells expressing a gene product of SLC7A11, wherein the gene product exhibits cystine/glutamate antiporter activity. In some aspects, the present disclosure is drawn to a cell comprising an RNAi oligonucleotide sequence described herein. In some aspects, the present disclosure is drawn to a vector comprising an RNAi oligonucleotide sequence described herein. In some aspects, the vector is an expression vector. In some aspects, the present disclosure is drawn to a cell comprising the vector described herein. In some aspects, the present disclosure is drawn to a liposome comprising an RNAi oligonucleotide sequence described herein.

In some aspects, the present disclosure is drawn to a method of treating, suppressing, or preventing tuberculosis in a subject, the method comprising administering to the respiratory tract of the subject an effective amount of: (a) a first antisense oligonucleotide sequence comprising at least 8 consecutive nucleotides selected from SEQ ID NO:2, and/or (b) a second antisense oligonucleotide sequence comprising at least 8 consecutive nucleotides selected from SEQ ID NO:13.

In some aspects, the present disclosure is drawn to a method of preventing human herpesvirus 8 infection in a subject, the method comprising systemic administration to the subject with an effective amount of: (a) a first antisense oligonucleotide sequence comprising at least 8 consecutive nucleotides selected from SEQ ID NO:2, and/or (b) a second antisense oligonucleotide sequence comprising at least 8 consecutive nucleotides selected from SEQ ID NO:13.

In some aspects, the present disclosure is drawn to a method of preventing Kaposi's in a subject, the method comprising administering to the circulatory system of the subject with an effective amount of: (a) a first antisense oligonucleotide sequence comprising at least 8 consecutive nucleotides selected from SEQ ID NO:2, and/or (b) a second antisense oligonucleotide sequence comprising at least 8 consecutive nucleotides selected from SEQ ID NO:13; wherein the subject is HIV positive or is both HIV positive and exhibiting signs of AIDS.

In some aspects, the present disclosure is drawn to a method of preventing liver fibrosis in a subject, the method comprising administering to the subject an effective amount of: (a) a first antisense oligonucleotide sequence comprising at least 8 consecutive nucleotides selected from SEQ ID NO:2, and/or (b) a second antisense oligonucleotide sequence comprising at least 8 consecutive nucleotides selected from SEQ ID NO:13.

In some aspects, the present disclosure is drawn to a method of increasing speed of recover in a subject with a spinal cord injury, the method comprising administering to the subject's spinal cord at the site of the spinal cord injury an effective amount of: (a) a first antisense oligonucleotide sequence comprising at least 8 consecutive nucleotides selected from SEQ ID NO:2, and/or (b) a second antisense oligonucleotide sequence comprising at least 8 consecutive nucleotides selected from SEQ ID NO:13.

The following detailed description is exemplary and explanatory, and is intended to provide further explanation of the invention.

electron transport chain. TCA: tricarboxylic acid cycle. (B) Gene-level analysis of a genome-wide CRISPR/Cas9 screen in glucose and galactose. Each dot represents an expressed, non-essential gene (n=9,189). (C) Gene ontology analysis generated using a gene list ranked by viability in galactose against GO components at FDR<0.001. (D-F) Functional validation of the screening results. Basal whole-cell oxygen consumption rates (OCR), extracellular acidification rates (ECAR) and OCR/ECAR ratios were simultaneously measured after CRISPR/Cas9-mediated gene depletion in K562 cells grown in glucose-containing media. Data are shown as mean±SEM (n≥3 independent experiments. *p<0.05, p<0.01, *p<0.001, t test relative to control (GFP) sgRNA-treated cells. NDUFB5 is a control with known role in OXPHOS.

Figure 2:
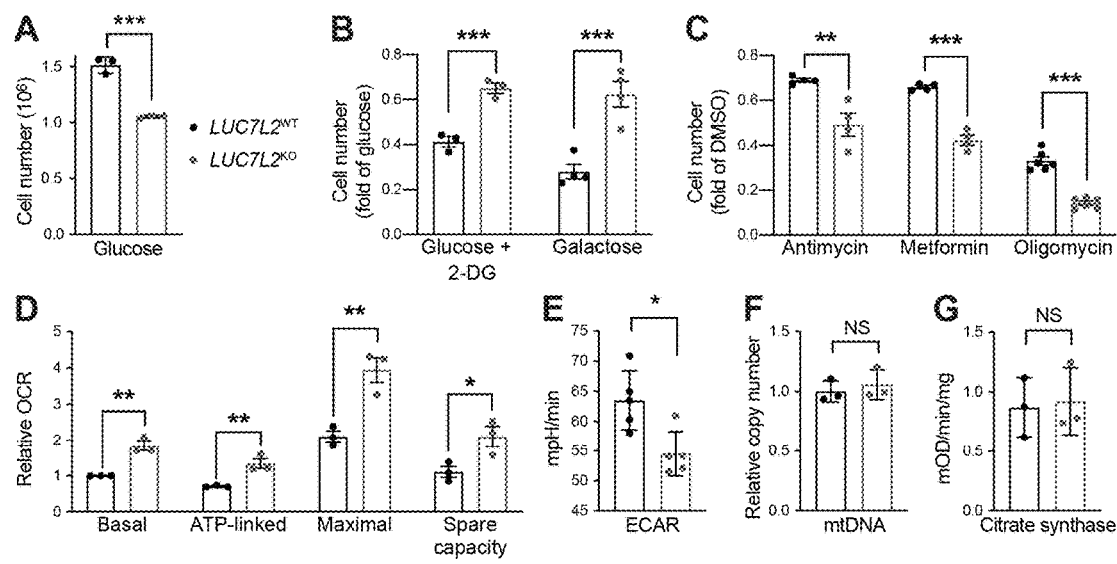

FIG. 2. (A-C) Cell proliferation of LUC7L2$^{WT}$ and LUC7L2$^{KO}$ K562 cells grown in (A) 25 mM glucose and (B) treated with 2-deoxyglucose (2-DG) or when glucose was replaced by 25 mM galactose or (C) 25 mM glucose with OXPHOS inhibitors. (D) Respiratory parameters of LUC7L2$^{WT}$ and LUC7L2$^{KO}$ cells as determined by whole-cell oxygen consumption rate (OCR). (E) Basal glycolytic activity in LUC7L2$^{WT}$ and LUC7L2$^{KO}$ cells as determined by whole-cell extracellular acidification rate (ECAR). (F) Relative mtDNA abundance and (G) citrate synthase activity of LUC7L2$^{WT}$ and LUC7L2$^{KO}$ cells. All data are shown as mean±SEM (n≥3). *p<0.05, p<0.01, *p<0.001 t-test relative to LUC7L2$^{WT}$ cells.

Figure 3:
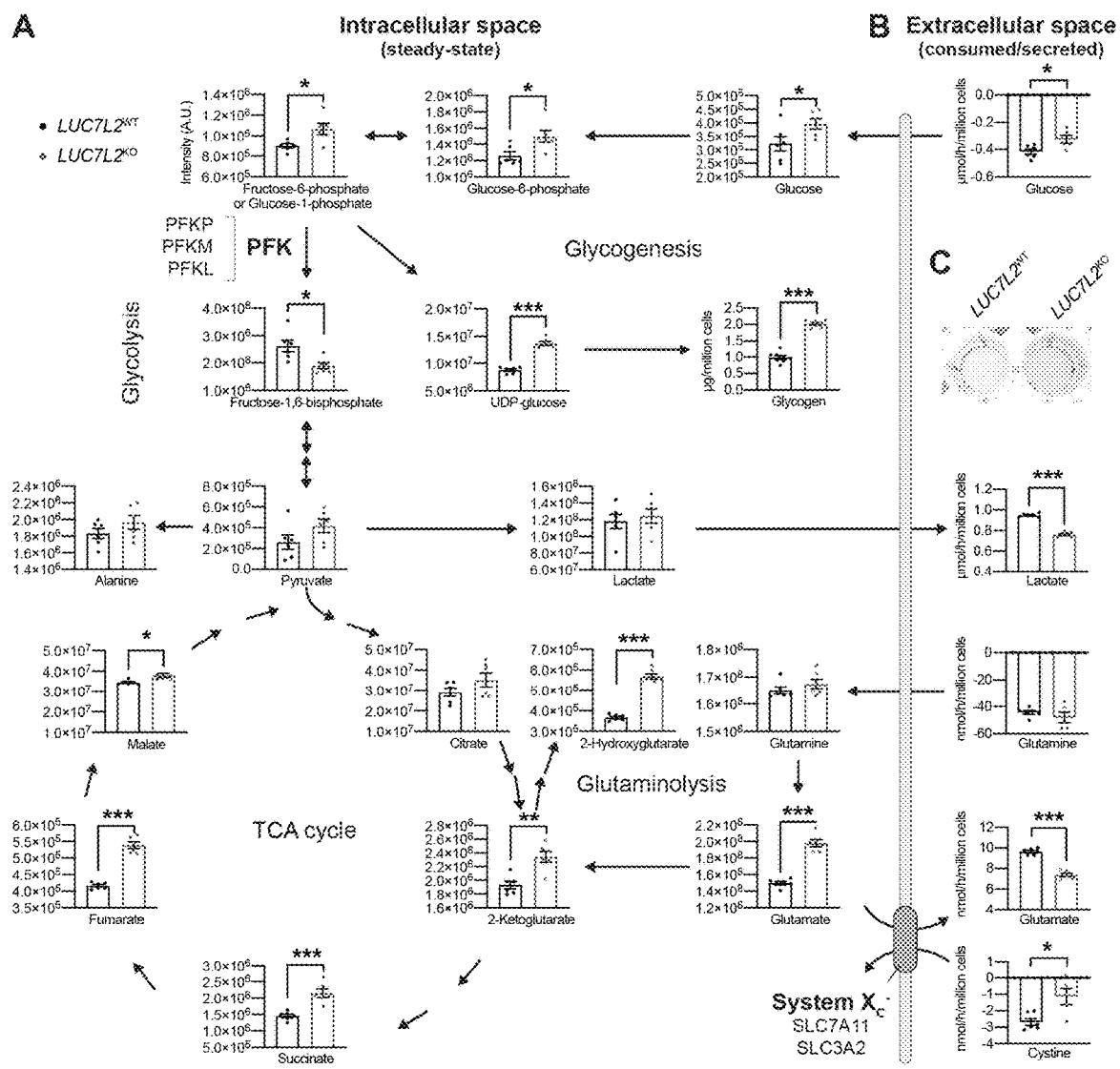

FIG. 3. (A) Intracellular levels of metabolites as determined by LC-MS. LUC7L2$^{WT}$ and LUC7L2$^{KO}$ cells were plated in fresh media 8 h before harvesting samples. (B) Extracellular levels of metabolites as determine by LC-MS analysis of the spent media from (A). Positive and negative values illustrate metabolite secretion and consumption by the cells, respectively. All data are shown as mean±SEM (n=5-8). *p<0.05, p<0.01, *p<0.001, t-test relative to LUC7L2$^{WT}$ cells. (C) Media acidification of LUC7L2$^{WT}$ and LUC7L2$^{KO}$ K562 cells grown in 25 mM glucose. An equal number of cells was plated in fresh media at high density 3 h before imaging.

Figure 4:
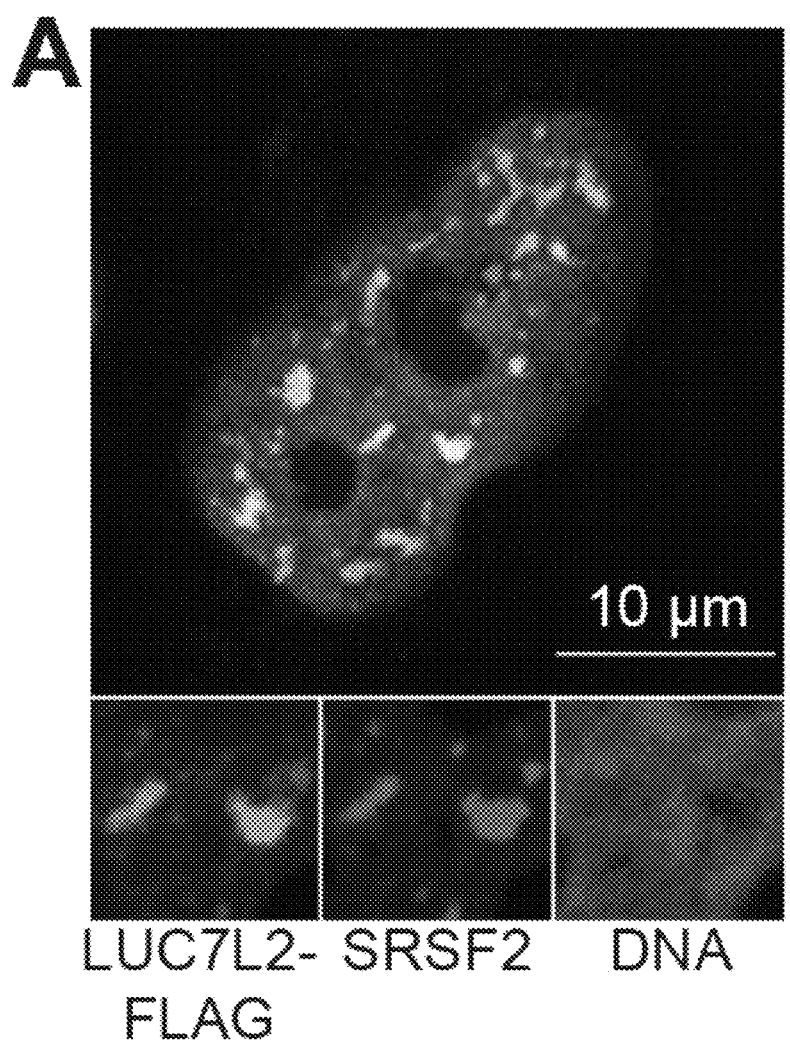
Figure 4:
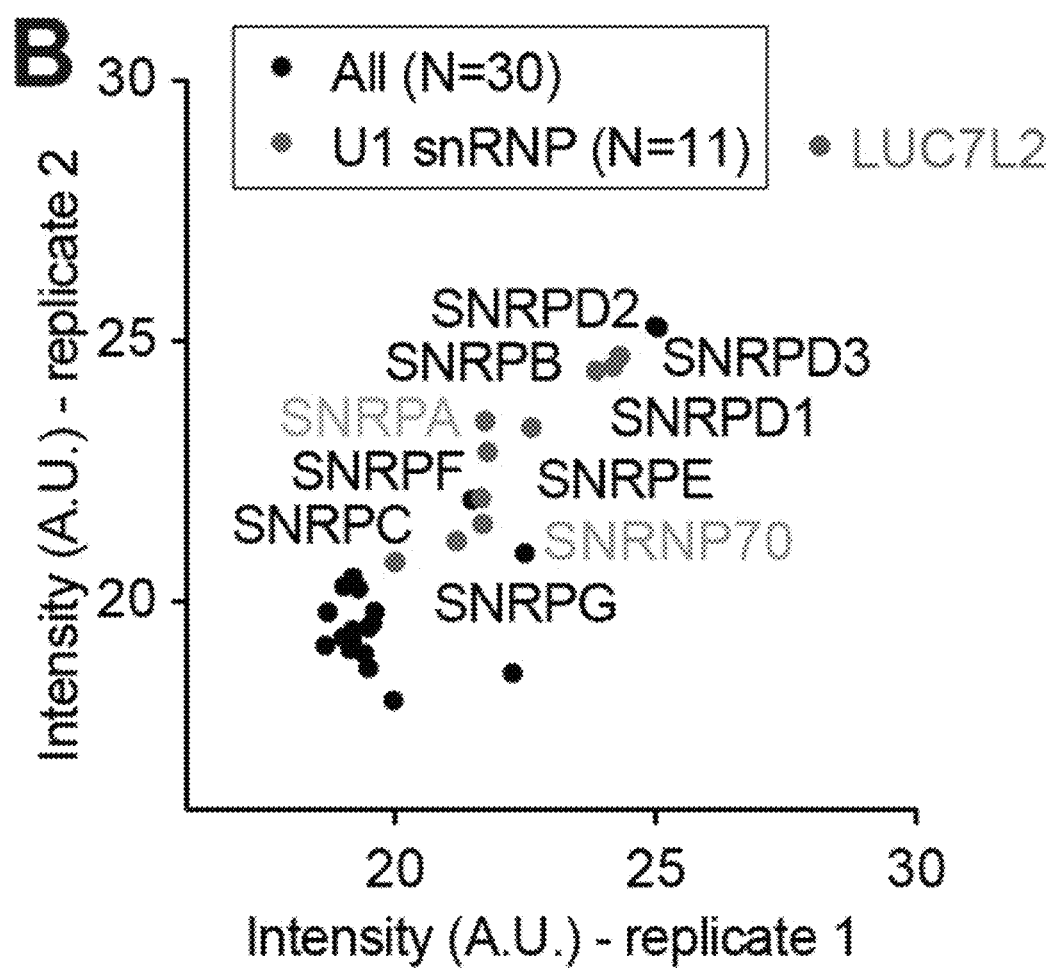
Figure 4:
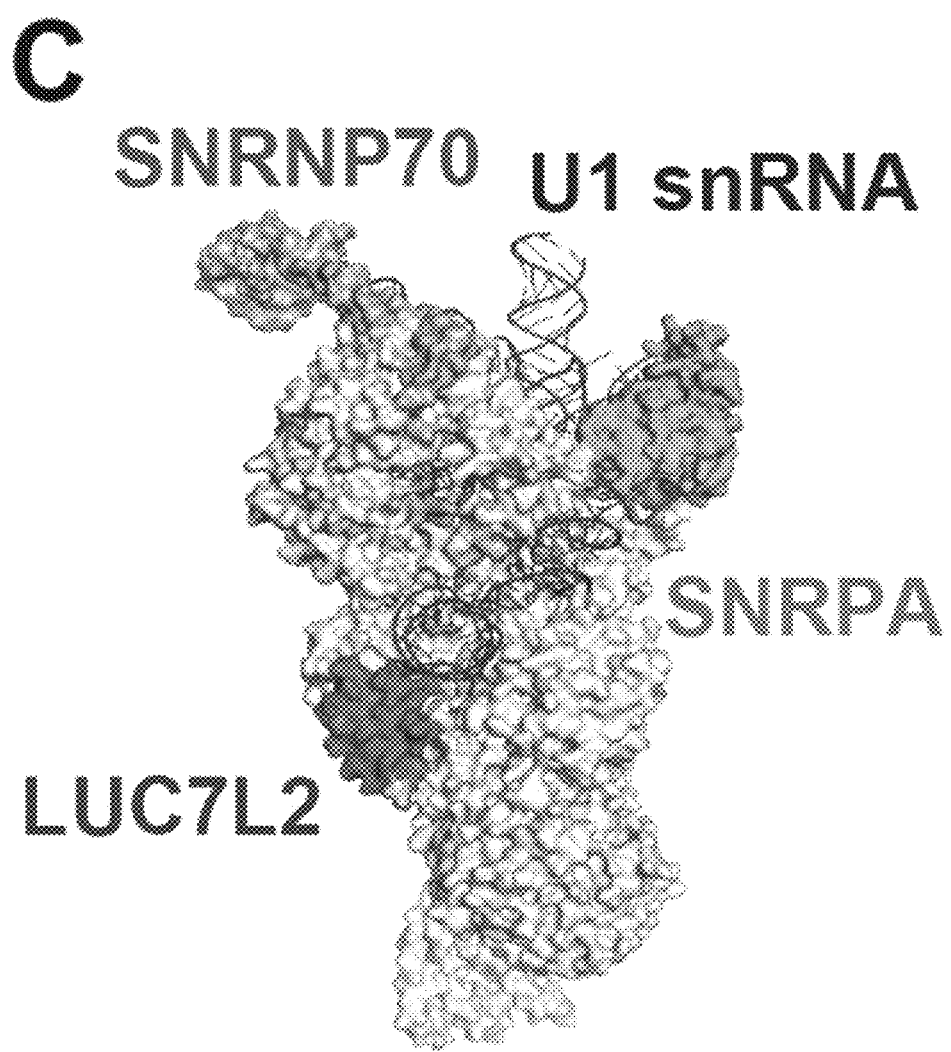
Figure 4:
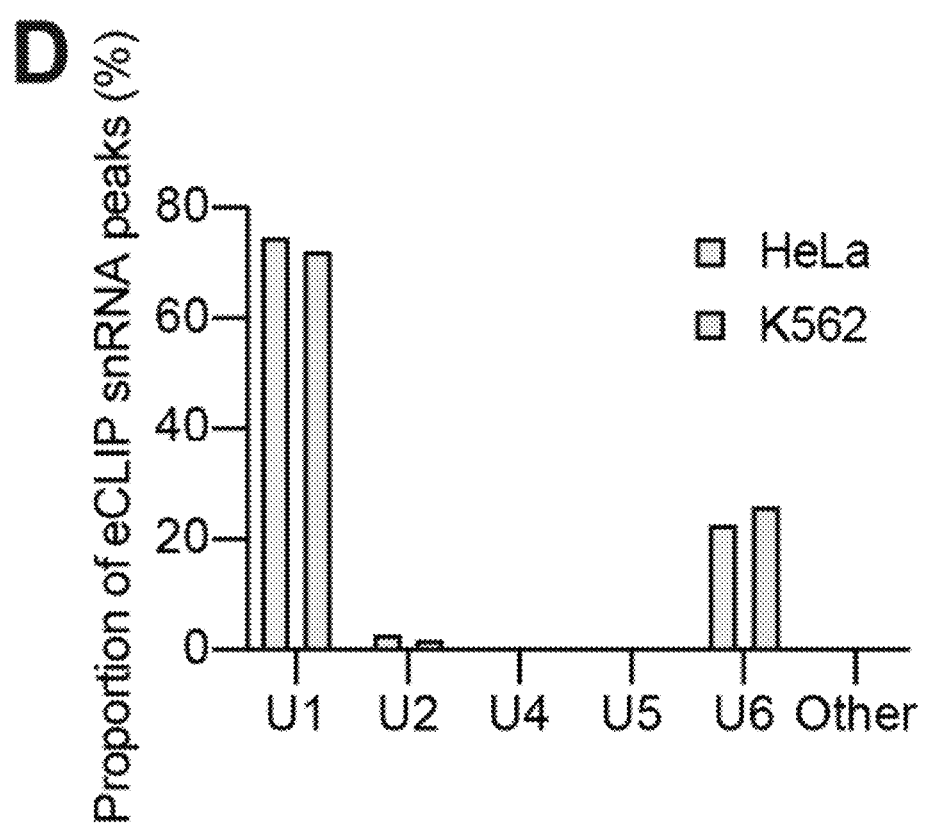
Figure 4:
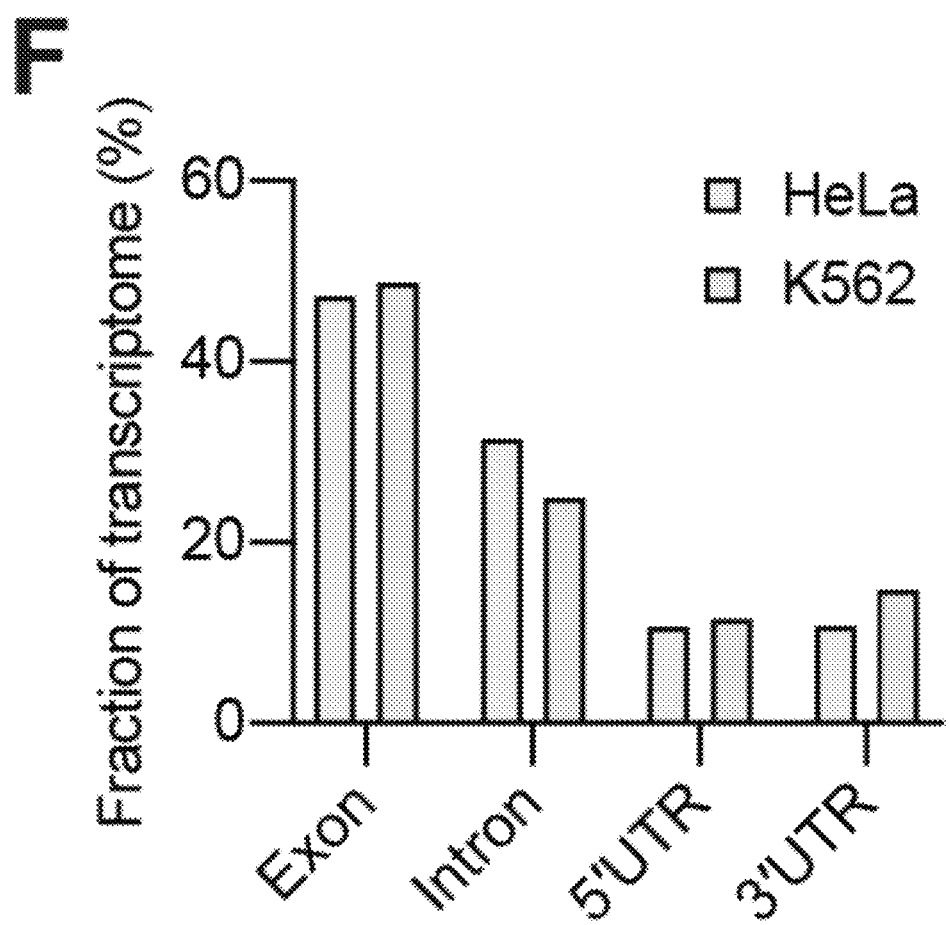
Figure 4:
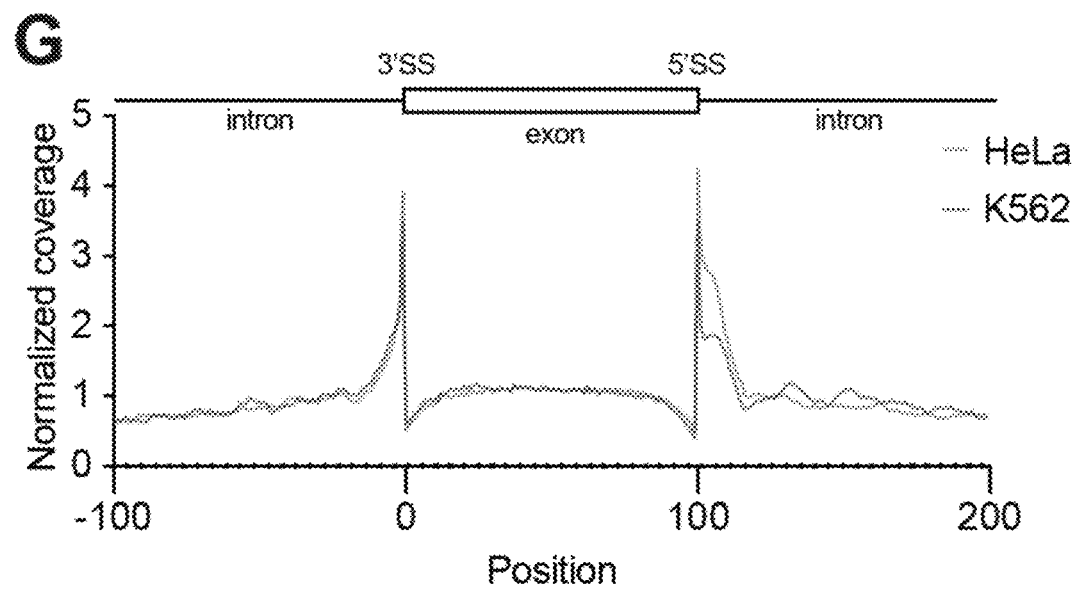
Figure 4:
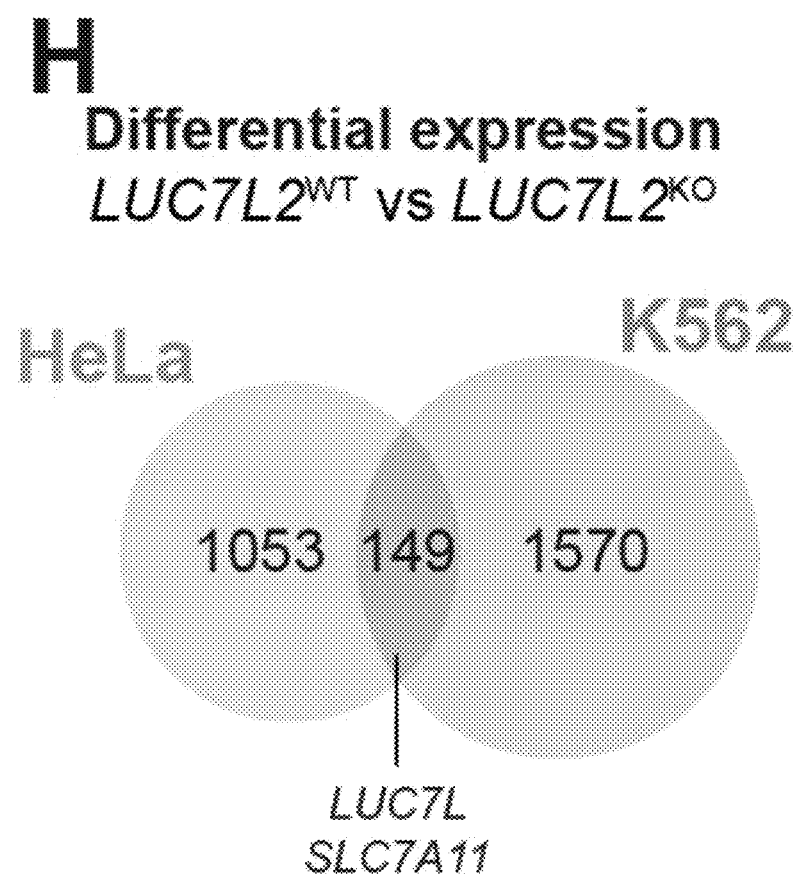
Figure 4:
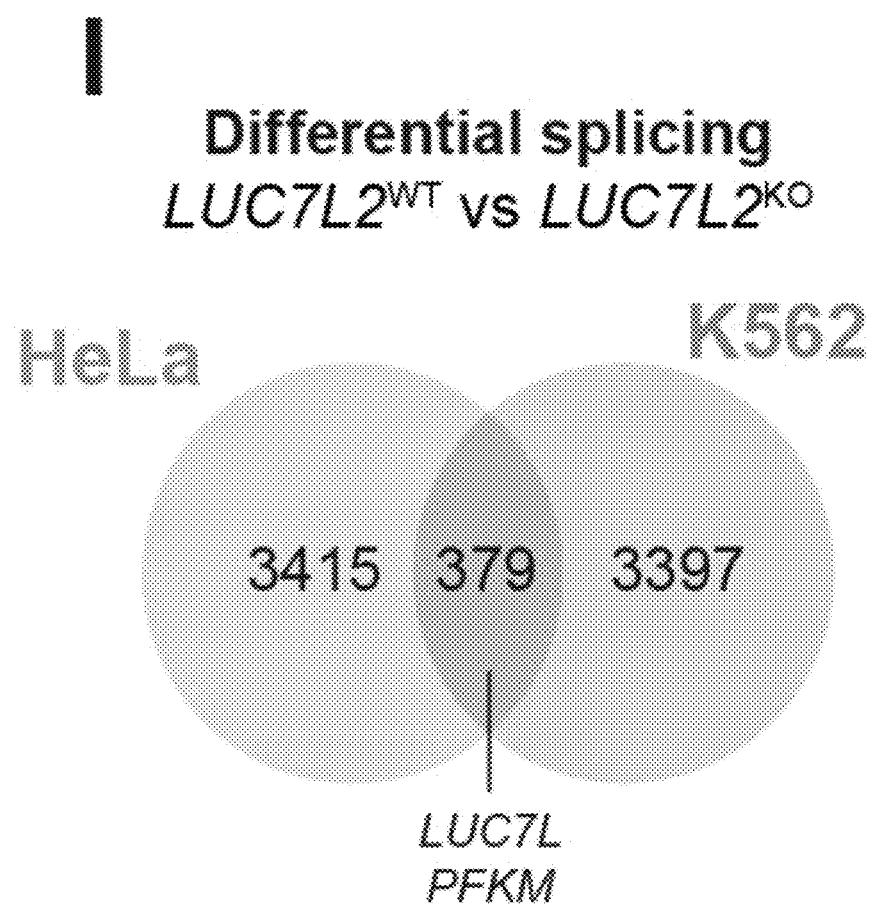
Figure 4:
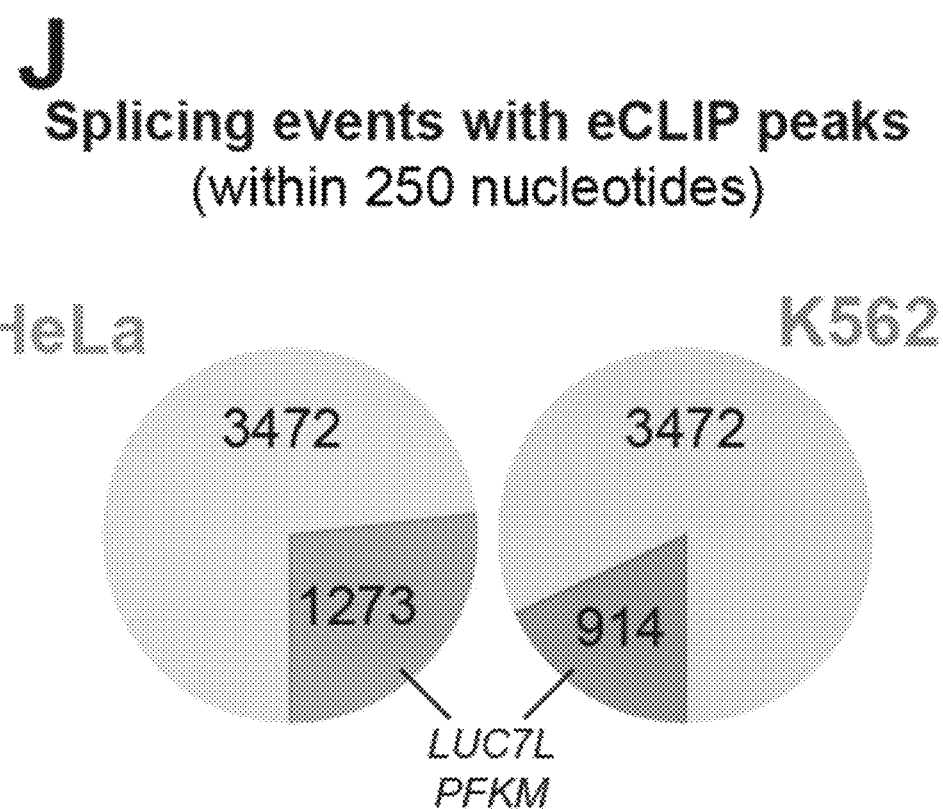
Figure 4:
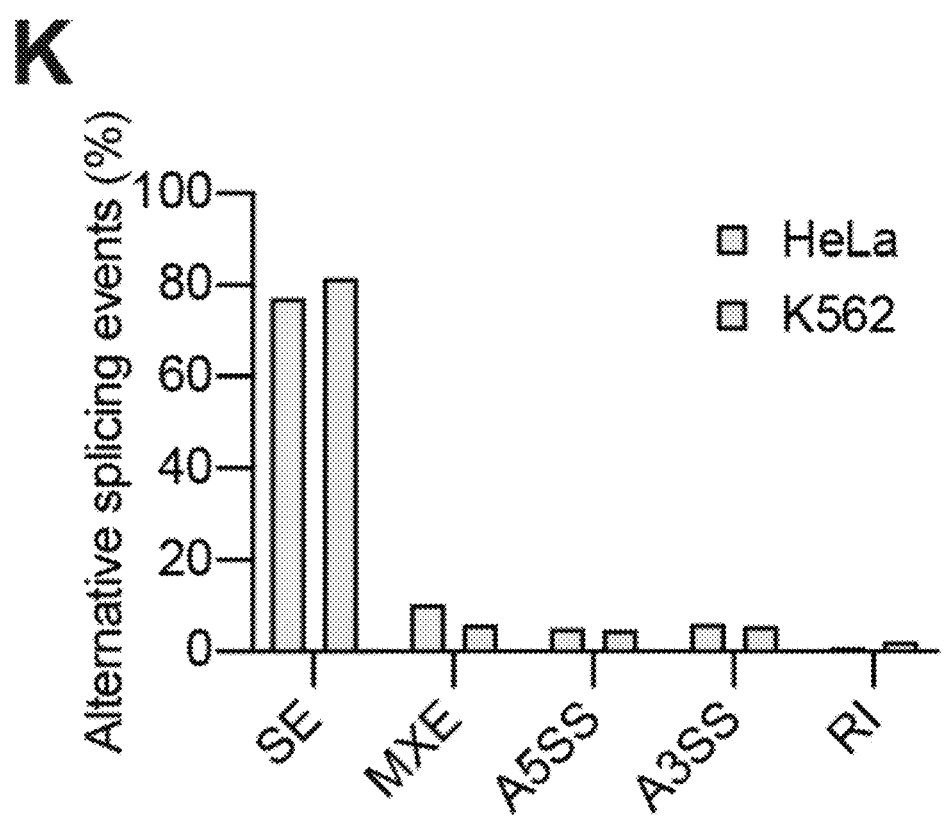

FIG. 4. (A) Confocal microscopy of a single nucleus from a HeLa cell expressing LUC7L2-FLAG and immunolabeled with antibodies to FLAG and SRSF2. (B) LUC7L2-interacting proteins as determined by IP-MS (n=2). Only proteins identified with unique peptides are reported. (C) Representation of LUC7, SNRPA and SNRNP70 on the yeast U1 snRNP (PDB 5UZ5) (Li et al., 2017). (D) Proportion of eCLIP peaks mapping to splicing U1 snRNAs in HeLa and K562 cells after eCLIP and CLIPper analysis at P<10$^{-4}$ (n=2, each). (E) Venn diagram representation of the mRNAs bound by LUC7L2 in HeLa and K562 cells at P<10$^{-4}$ (n=2, each). (F) Binding sites of LUC7L2 in pre-mRNAs at P<10$^{-4}$ (n=2, each). (G) Meta-analysis of LUC7L2 binding sites across shared eCLIP peaks in HeLa and K562 cells at P<10$^{-4}$ (n=2, each). (H) Venn diagram representation of differential gene expression analysis from LUC7L2$^{WT}$ and LUC7L2$^{KO}$ cells (n=3 for each cell type and each genotype) as determined by RNA deep sequencing at FDR<10$^{-4}$ and >|1.5| fold change. (I) Venn diagram representation of the alternative splicing events seen in LUC7L2$^{KO}$ cells as determined by rMATS at FDR<0.1 and |Δψ|>0.05 (n=3 for each cell type and each genotype). (J) Alternative events presenting an eCLIP peak at a 250-nucleotide distance at P<10$^{-2}$ (in darker shade, n=2 each). (K) Differential alternative splicing types in LUC7L2$^{WT}$ and LUC7L2$^{KO}$ cells with SE: skipped exon; MXE: mutually-exclusive exons; A5SS: alternative 5' splice site; A3SS: alternative 3' splice site; RI: retained intron.

Figure 5:
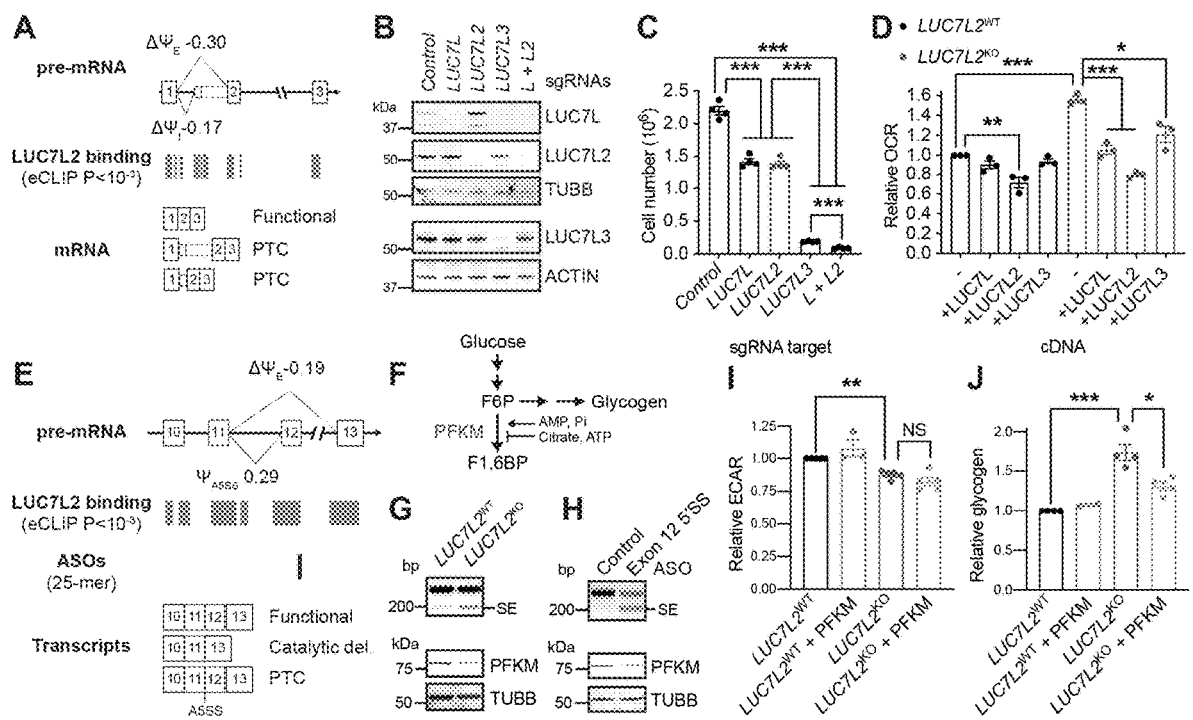

FIG. 5. (A) Representation of LUC7L exon 1-3, LUC7L2 binding sites as determined by eCLIP, and the expected transcripts. Ψ: percent spliced in reported by rMATS in K562 cells. I: intron. E: exon. (B) Immunoblot against all subunits of the LUC7 family in cell lines expressing Cas9 and sgRNAs targeting GFP (control), LUC7L, LUC7L2 and LUC7L3 using the indicated antibodies and (C) number of cells after 4 days of growth in glucose-containing media. (D) Oxygen consumption analysis of LUC7L2$^{WT}$ and LUC7L2$^{KO}$ K562 cells expressing cDNAs of LUC7 family members. (E) Representation of PFKM exons 10-13, LUC7L2 binding sites as determined by eCLIP, antisense oligonucleotides (ASOs) targeting sites and the expected transcripts. A positive Δψ value indicates increased exon inclusion. A5SS indicated alternative 5'SS. (F) Representation of the role of PFKM in metabolism. (G) RT-PCR (top) and immunoblot (bottom) of LUC7L2$^{WT}$ and LUC7L2$^{KO}$ K562 cells or (H) HAP1 cells treated for 48 h with ASOs targeting the 5'SS of PFKM exon 12. (I) Relative ECAR (n=3-5) and (J) glycogen in LUC7L2$^{WT}$ and LUC7L2$^{KO}$ K562 cells expressing control cDNAs (GFP) or PFKM cDNA (n=2-4). All data are shown as mean±SEM with *p<0.001, p<0.01, *p<0.05 t-test relative to the indicated control.

Figure 6:
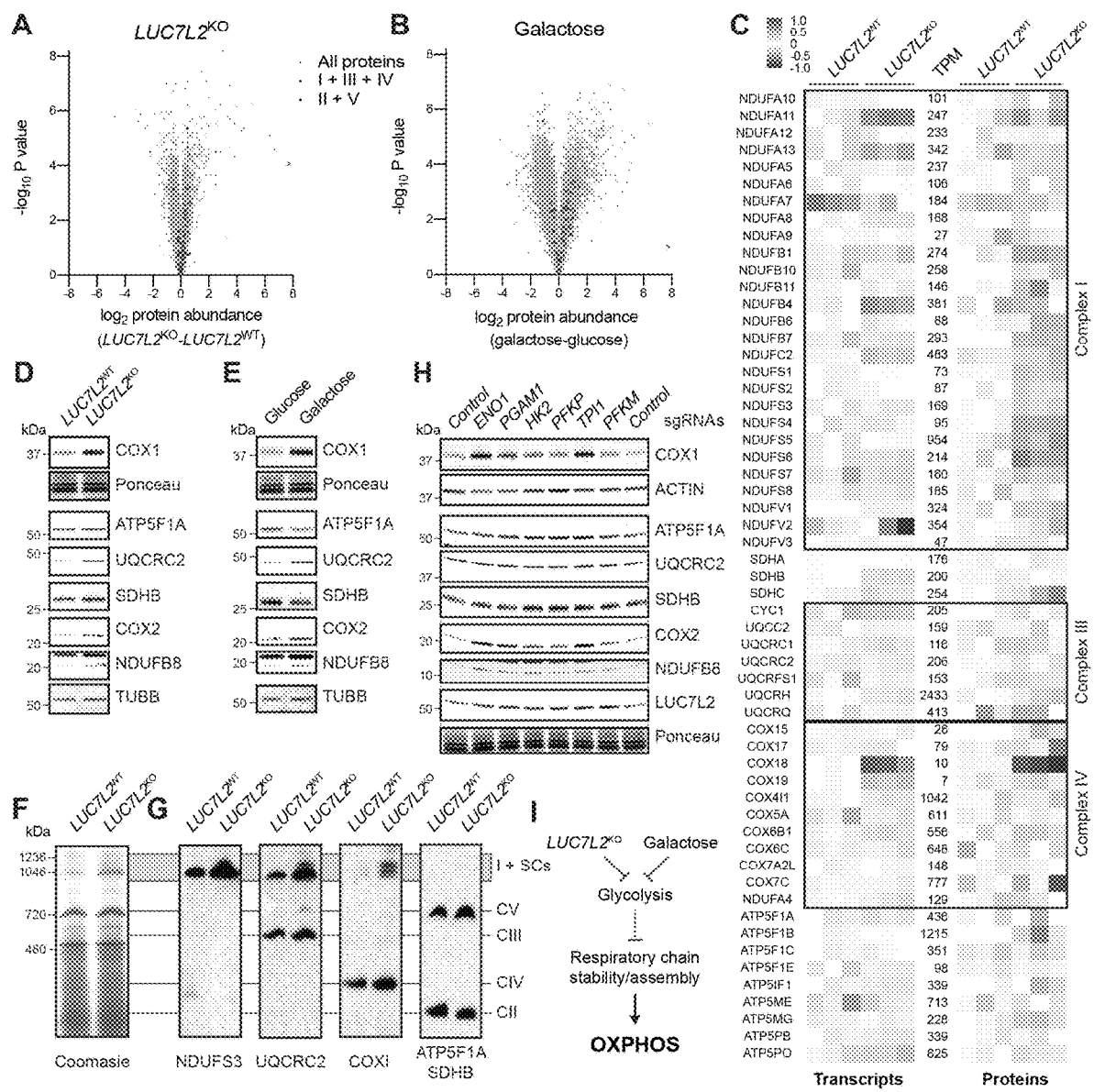

FIG. 6. (A) Volcano plots of differential protein expression in control vs. LUC7L2$^{KO}$ K562 cells and (B) K562 cells grown for two weeks in galactose media. (C) Heat-map of OXPHOS transcripts and proteins in LUC7L2$^{WT}$ and LUC7L2$^{KO}$ K562 cells expressed as fold of LUC7L2$^{WT}$ TPM: transcripts per million. Subunits of complex I, III and IV are framed. (D) Immunoblot on LUC7L2$^{WT}$ and LUC7L2$^{KO}$ K562 cells and (E) K562 cells grown for two weeks in galactose media with the indicated antibodies. (F) Blue-Native PAGE on a mitochondria-rich fraction isolated from LUC7L2$^{WT}$ and LUC7L2$^{KO}$ K562 cells and stained with coomasie or (G) immunoblotted with antibodies to NDUFS3, UQCRC2, COX1, SDHB or ATP5F1A. Parallel blots in which the same lysate was loaded were used to avoid antibodies cross-reactivity. SCs: supercomplexes. CI-V: complex I to complex V. (H) Immunoblot on K562 cells expressing Cas9 and treated with sgRNAs targeting glycolytic enzymes with the indicated antibodies. (I) Model of the secondary regulation of the respiratory chain by LUC7L2 and galactose.

Figure 7:
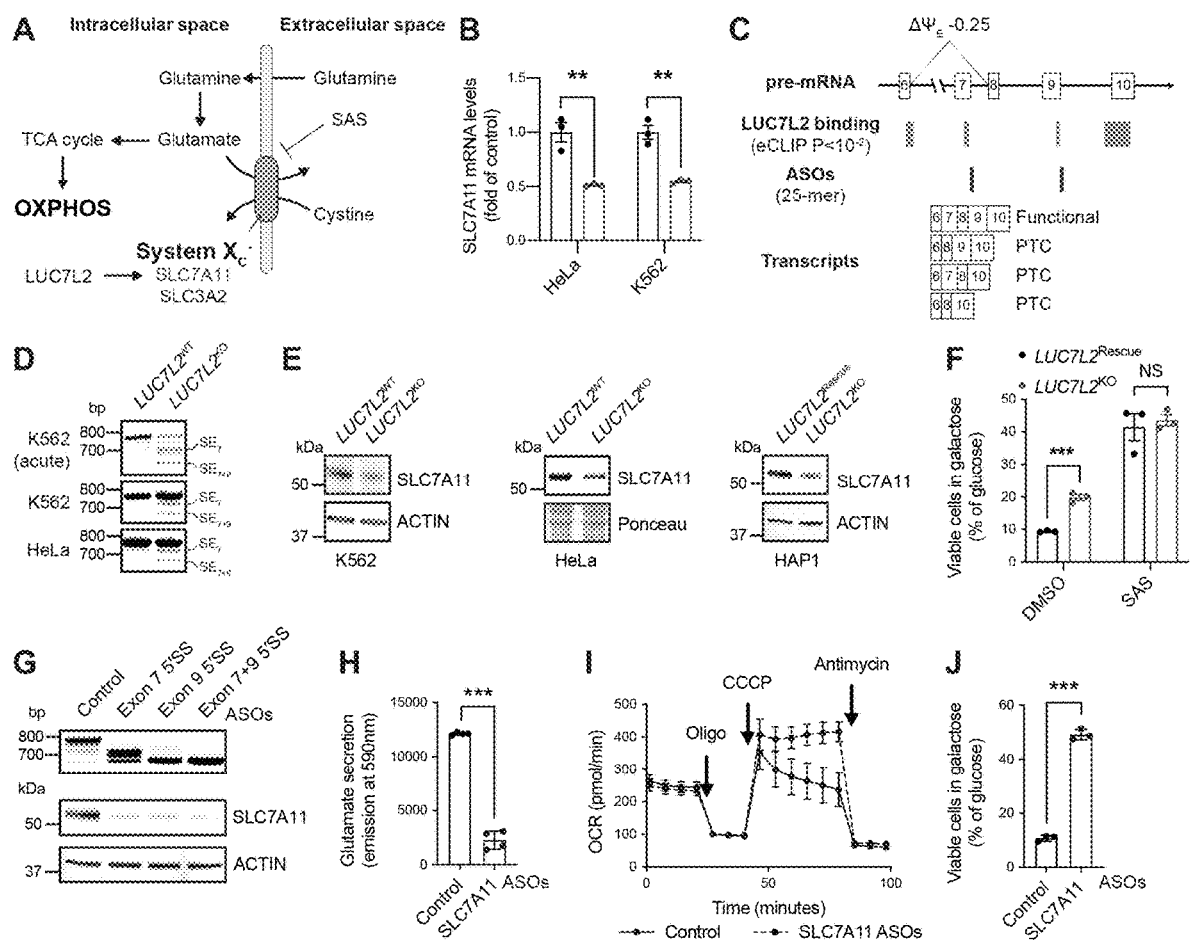

FIG. 7. (A) Role of the system X$_c^-$ in glutamate export and anaplerosis. SAS: sulfasalazine. (B) Quantitative PCR with probes detecting SLC7A11 in LUC7L2$^{WT}$ and LUC7L2$^{KO}$ HeLa and K562 cells (n=3). (C) Schematic representation of SLC7A11 exon 6-10 including LUC7L2 binding sites as determined by eCLIP, antisense oligonucleotides (ASOs) targeting sites and the expected transcripts. Ψ: percent spliced in reported by rMATS in K562 cells. E: exon. A negative Δψ value indicates exon skipping. PTC: premature termination codons. (D) RT-PCR of LUC7L2$^{WT}$ and LUC7L2$^{KO}$ K562 cells with primers amplifying transcripts corresponding to SLC7A11 exon 6-12. SE: skipped exon. (E) Immunoblot on LUC7L2$^{WT}$ (or LUC7L2$^{Rescue}$) and LUC7L2$^{KO}$ K562, HeLa and HAP1 cells with antibodies to SLC7A11 and ACTIN. (F) Cell viability of LUC7L2$^{Rescue}$ and LUC72L2$^{KO}$ cells grown for 24 h in galactose relative to glucose (n=3). SAS was used at 500 µM. (G) RT-PCR (top) and immunoblot (bottom) of HAP1 cells treated for 48 h with ASOs targeting the 5'SS of exon 7 and/or exon 9 of SLC7A11. (H) Media glutamate (n=4), (I)

representative seahorse trace (shown as mean±SD), and (J) viability in galactose of HAP1 cells treated for 48 h with ASOs targeting the 5'SS of SLC7A11 exon 7 and 9 (n=3). All data are shown as mean±SEM (unless otherwise stated) with * p<0.05,  p<0.01, *p<0.001 t-test relative to control.

DETAILED DESCRIPTION

Glycolysis and oxidative phosphorylation (OXPHOS) are the two major pathways for energy metabolism in human cells (FIG. 1A). While glycolysis occurs in the cytosol, OXPHOS is dependent on the mitochondrial respiratory chain. The two pathways are associated with key tradeoffs, and while glycolysis tends to be kinetically favorable, the ATP yield from OXPHOS is much higher (Pfeiffer et al., 2001). The relative balance of OXPHOS and glycolysis is known to vary across tissues, for example, cardiac tissue is rich in mitochondria and highly oxidative in its metabolism, whereas proliferating cells from the thymus are highly glycolytic (Warburg, 1924). The balance between these two programs can vary during cellular differentiation and in response to environmental stimuli. Activation of quiescent immune cells by antigens is often accompanied by rewiring towards glycolytic ATP production, while stem cell differentiation results in increased OXPHOS (Pearce et al., 2013, Ito and Suda, 2014). Cells also acutely respond to nutrient and oxygen availability to adjust flux through these energy metabolism pathways within minutes (Crabtree, 1929, Pasteur, 1861), while oncogenic transformation promotes aerobic glycolysis (Warburg, 1924). Notably, differential reliance on OXPHOS versus glycolysis can be exploited for therapeutic benefit (Bonnet et al., 2007, Gohil et al., 2010).

Certain genomic programs are known to shape the expression and balance of cellular energy metabolism. For example, the transcriptional co-activator PGC-1α integrates nutrient levels and physiological inputs to orchestrate an entire genomic program that induces the expression of the OXPHOS machinery (Puigserver et al., 1998). Conversely, the transcription factor HIF-1α promotes expression of a set of glycolytic enzymes in response to a decline in oxygen (Huang et al., 1998). Post-transcriptionally, RNA-binding proteins such as CLUH bind to a large number of mRNAs encoding mitochondrial proteins (Gao et al., 2014). A few instances of alternative splicing in regulating individual metabolic enzymes have also been reported. For example, alternative splicing generates the PKM2 isoform of the pyruvate kinase, re-routes lower glycolytic carbon flux, and is believed to contribute to cancer progression (Christofk et al., 2008).

High-throughput approaches are powerful tools for deciphering cellular metabolic programs (Hillenmeyer et al., 2008, VanderSluis et al., 2014). We previously reported a nutrient-sensitized screen for small molecules that impact the fitness of cells in galactose, a poor substrate for glycolysis, and focused on dozens of small molecules that induce a shift from OXPHOS to glycolysis (Gohil et al., 2010). More recently, we reported the first genome-wide identification of genes necessary to sustain OXPHOS (Arroyo et al., 2016). We systematically catalogued 300 genes whose loss impaired OXPHOS in human cells, including 72 that underlie known OXPHOS diseases. However, that report did not explore the opposite side of the screen, which could in principle include pathways that tonically suppress OXPHOS.

Here, we report the genome-wide identification of "OXPHOS repressors", defined as genes whose knockout promotes relative fitness in the absence of glucose as a fuel for glycolysis. We validate top-scoring genes and show that their depletion augments OXPHOS activity, while attenuating glycolysis. OXPHOS repressors are enriched for components of the pre-mRNA splicing machinery, including subunits of the U1 snRNP. Among them, we show that LUC7L2 is required for a splicing program involving a set of metabolic genes, including PFKM and SLC7A11 (xCT), that collectively favors glycolysis over OXPHOS. Together, our observations indicate that LUC7L2 and the U1 snRNP represent previously unappreciated factors in the expression and control of the machinery driving energy metabolism.

Disclosed herein, in certain embodiments, are methods of delivering a therapeutic transgene (e.g., a dimert disclosed herein) with use of a gene therapy vector. In some embodiments, the gene therapy vector provides a stable sustained expression of the therapeutic transgene (e.g., the dimert). In additional embodiments, the gene therapy vector provides a constitutive expression. In further embodiments, the gene therapy vector provides a regulated expression. In some cases, the gene therapy vector is transduced in normal cells (e.g., in organ cells such as liver cells or in muscle cells). In some cases, a single administration of the gene therapy vector is sufficient to induce a stable sustained expression of the therapeutic transgene (e.g., the dimert). In additional cases, the gene therapy vector provides a continuous, long-term expression of the therapeutic transgene (e.g., the dimert) which provides long-term pressure on cancer cells.

In certain embodiments, disclosed herein is a novel method that activates transgene expression (e.g., a dimert disclosed herein) which can be used as a gene therapy platform for a regulated expression, e.g., short-term gene expression (e.g., weeks to months, further optionally one week, two weeks, three weeks, four weeks, one month, 2 months, 3 months, 4 months, 5 months, 6 months, 8 months, or more). In some instances, the method utilizes a TransSkip. In one aspect, transgene expression is placed under control of a drug or an external agent (e.g., an OncoSkip), such that administration of the drug or the agent modulates (activates or inactivates) gene expression. On the other hand, lack of administration or withdrawal of the drug or the agent reverts to the original status of gene expression before the administration. For example, when the drug or the agent can activate the gene expression, if there are side effects or if expression of the transgene is no longer needed, withdrawal of the administration can inactive the gene expression, thereby minimizing the side effects, if any. In some instances, the TransSkip is transduced in normal cells (e.g., in organ cells such as liver cells or in muscle cells). In some cases, a single administration of the TransSkip is sufficient to induce a stable sustained expression of the therapeutic transgene (e.g., the dimert). In additional cases, the TransSkip provides a regulated but continuous expression of the therapeutic transgene (e.g., the dimert) which provides long-term pressure on cancer cells.

Exon-skipping is a technology used to treat certain genetic diseases in which a short region of a gene is defective. The DNA mutations result in a damaged protein either because the wrong amino acids appear in the protein, or they generate a stop mutation resulting a truncated protein, or they change the reading frame generating both. Because mammalian genes are typically encoded in exons, meaning they are split into multiple gene segments (exons) that get spliced together during processing of mRNA, the DNA mutations (changes in or deletions of base pairs) that underlie many diseases are contained within a single exon. If that exon can be skipped over, and not included in the final spliced mRNA, then the mutated region will not be included in the final protein. While the protein will be shorter and may be missing some parts, it will be still be "in frame" and might retain some of its function.

For example, Duchenne muscular dystrophy (DMD) and Becker muscular dystrophy (BMD) are the most common childhood forms of muscular dystrophy, which are caused by genetic defects in the DMD gene encoding dystrophin, a muscle protein that is required for interactions between the cytoskeleton and the extracellular matrix to maintain muscle fiber stability during contraction. DMD mutations in the dystrophin gene are characterized by frame shifting insertions or deletions or nonsense point mutations, resulting in the absence of functional dystrophin. BMD mutations in general keep the reading frame intact, allowing synthesis of a partly functional dystrophin. An exon-skipping based therapy resulted in transforming the out-of-frame mutations present in the DMD patients to in-frame mutations that encodes partially functional dystrophin. In 2016 the FDA approved the first exon-skipping drug, Eteplirsen™ (Sarepta Therapeutics) for Duchenne muscular dystrophy with mutations in exon 51 of the dystrophin gene. When the drug (which is a modified short stretch of DNA also called an oligo) is administered, exon 51 is "skipped" to restore a near full-length and more functional protein. Similar technology is being developed to skip other dystrophin exons as well as exons in other disease-causing genes.

In a further aspect, the extent and type of splicing is modified by the cell type, as many genes normally undergo alternative splicing that sometimes varies by cell type. In addition, splicing is sometimes altered in certain cancer cells (some exons of certain genes may be included or excluded in normal versus cancer cells). This technology can leverage these features to achieve transgene control that differs in normal versus cancer cells. Thus, in one aspect, modulation of splicing of the genes described herein provides a method of treating cancer.

Definitions

While the following terms are believed to be well understood by one of ordinary skill in the art, the following definitions are set forth to facilitate explanation of the presently disclosed subject matter.

The term "a" or "an" may refer to one or more of that entity, i.e. can refer to plural referents. As such, the terms "a" or "an", "one or more" and "at least one" are used interchangeably herein. In addition, reference to "an element" by the indefinite article "a" or "an" does not exclude the possibility that more than one of the elements is present, unless the context clearly requires that there is one and only one of the elements.

Reference throughout this specification to "one embodiment", "an embodiment", "one aspect", or "an aspect" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

As used herein, the terms "about" or "approximately" when preceding a numerical value indicates the value plus or minus a range of 10% of the value.

Also as used herein, "and/or" refers to and encompasses any and all possible combinations of one or more of the associated listed items, as well as the lack of combinations when interpreted in the alternative ("or").

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

As used herein, a "control" is an alternative sample used in an experiment for comparison purpose. A control can be "positive" or "negative." A "control sample" or "reference sample" as used herein, refers to a sample or reference that acts as a control for comparison to an experimental sample. For example, an experimental sample comprises compound A, B, and C in a vial, and the control may be the same type of sample treated identically to the experimental sample, but lacking one or more of compounds A, B, or C.

As used herein, the term "effective amount" refers to a quantity sufficient to achieve a desired therapeutic and/or prophylactic effect, e.g., an amount which results in the prevention of one or more outcomes, or an increase in one more outcomes.

As used herein, the terms "individual", "patient", or "subject" can be an individual organism, a vertebrate, a mammal, or a human. In a preferred aspect, the individual, patient, or subject is a human.

The term "cell" as used herein may refer to either a prokaryotic or eukaryotic cell, optionally obtained from a subject or a commercially available source.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect, and mammalian cells. Non-limiting examples of eukaryotic cells or hosts include simian, bovine, porcine, murine, rat, avian, reptilian, and human, e.g., HEK293 cells and 293T cells.

"Prokaryotic cells" that usually lack a nucleus or any other membrane-bound organelles and are divided into two domains, bacteria, and archaea. In addition to chromosomal DNA, these cells can also contain genetic information in a circular loop called on episome. Bacterial cells are very small, roughly the size of an animal mitochondrion (about 1-2 µm in diameter and 10 µm long). Prokaryotic cells feature three major shapes: rod shaped, spherical, and spiral. Instead of going through elaborate replication processes like eukaryotes, bacterial cells divide by binary fission.

Examples include but are not limited to *Bacillus* bacteria, *E. coli* bacterium, and *Salmonella* bacterium.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

The terms "equivalent" or "biological equivalent" are used interchangeably when referring to a particular molecule, biological, or cellular material and intend those having minimal homology while still maintaining desired structure or functionality. Non-limiting examples of equivalent polypeptides, include a polypeptide having at least 60%, or alternatively at least 65%, or alternatively at least 70%, or alternatively at least 75%, or alternatively 80%, or alternatively at least 85%, or alternatively at least 90%, or alternatively at least 95% identity or alternatively at least 96% identity, or alternatively at least 97% identity, or alternatively at least 98% identity, or alternatively at least 99% identity for polypeptide sequences, or a polypeptide which is encoded by a polynucleotide or its complement that hybridizes under conditions of high stringency to a polynucleotide encoding such polypeptide sequences that has substantially identical or identical function as the reference polypeptide and in one aspect, encodes the reference polypeptide. Conditions of high stringency are described herein and incorporated herein by reference. Alternatively, an equivalent thereof is a polypeptide encoded by a polynucleotide or a complement thereto, having at least 70%, or alternatively at least 75%, or alternatively 80%, or alternatively at least 85%, or alternatively at least 90%, or alternatively at least 95% identity, or at least 96% identity, or at least 97% sequence identity, or alternatively at least 98% identity, or alternatively at least 99% identity to the reference polynucleotide, e.g., the wild-type polynucleotide or referenced polynucleotide.

Non-limiting examples of equivalent polynucleotides, include a polynucleotide having at least 60%, or alternatively at least 65%, or alternatively at least 70%, or alternatively at least 75%, or alternatively 80%, or alternatively at least 85%, or alternatively at least 90%, or alternatively at least 95%, or at least 96% identity, or at least 97% sequence identity, or alternatively at least 98% identity, or alternatively at least 99% identity to a reference polynucleotide. An equivalent also intends a polynucleotide or its complement that hybridizes under conditions of high stringency to a reference polynucleotide.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain embodiments, default parameters are used for alignment. A non-limiting exemplary alignment program is BLAST, using default parameters. In particular, exemplary programs include BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.govicgi-bin/BLAST. Sequence identity and percent identity can be determined by incorporating them into clustalW (available at the web address: genome.jp/tools/clustalw/, last accessed on Jan. 13, 2017).

"Homology" or "identity" or "similarity" refers to sequence similarity between two peptides or between two nucleic acid molecules. Homology can be determined by comparing a position in each sequence that may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present disclosure.

"Homology" or "identity" or "similarity" can also refer to two nucleic acid molecules that hybridize under stringent conditions.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6× saline sodium citrate (SSC) to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. A high stringency hybridization refers to a condition in which hybridization of an oligonucleotide to a target sequence comprises no mismatches (or perfect complementarity). Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

A "gene" refers to a polynucleotide containing at least one open reading frame (ORF) that is capable of encoding a particular polypeptide or protein after being transcribed and translated. A "gene product" or alternatively a "gene expression product" refers to the amino acid (e.g., peptide or polypeptide) generated when a gene is transcribed and translated.

"Under transcriptional control" is a term well understood in the art and indicates that transcription of a polynucleotide sequence, usually a DNA sequence, depends on its being operatively linked to an element which contributes to the initiation of, or promotes, transcription. "Operatively linked" intends the polynucleotides are arranged in a manner that allows them to function in a cell. In one aspect, this invention provides promoters operatively linked to the downstream sequences.

The term "exon" refers to a nucleic acid sequence that comprises a protein-coding sequence. The gene typically includes more than one exons, which are separated by an intron in between.

The term "intron" as used here refers to a nucleic acid sequence is flanked by a splice donor site on the 5' end and a splice acceptor site on the 3' end. In some embodiments, the intron is spliced out of or removed from an RNA or mRNA sequence expressed from the vector in which it is present.

The term "splice donor site" is a nucleic acid sequence or domain on the 5' end of an intron. The splice donor site, in one embodiment, marks the start of the intron and/or the intron's boundary with an immediately preceding coding sequence (or exon).

The term "splice acceptor site" as used herein refers to a nucleic acid sequence or domain on the 3' end of an intron. In one embodiment, the splice acceptor site marks the start of the intron and its boundary with the following coding sequence-exon. In another embodiment, the splice acceptor site comprises an intron branch point is the point to which the 5' end of the intron becomes joined during the process of splicing. In some embodiments, the splice acceptor sequence and the intron branch site are placed adjacent to each other as a single unit. In some embodiments, the splice acceptor sequence and the intron branch site may be further separated, by moving the branch site further 5' of the splice acceptor sequence.

The term "splice site" as used herein refers to a sequence or domain of a nucleic acid present at either the 5' end or the 3' end of an intron as defined above.

The term "exon skipping" as used herein refers to the modification of pre-mRNA splicing by the targeting of splice donor and/or acceptor sites within a pre-mRNA with one or more complementary antisense oligonucleotides. By blocking access of a spliceosome to one or more splice donor or acceptor site, the one or more complementary antisense oligonucleotides can prevent a splicing reaction, thereby causing the deletion of one or more exons from a fully-processed mRNA. In one embodiment, exon skipping is achieved in the nucleus during the maturation process of pre-mRNAs. It includes the masking of key sequences involved in the splicing of targeted exons by using antisense oligonucleotides that are complementary to splice donor sequences within a pre-mRNA.

The term "gene regulation sequence" as used herein refers to a nucleic acid sequence capable of controlling the transcription, splicing, or modification of a gene, an open reading frame, or an exon or intron. A gene regulation sequence of the invention may include a promoter, a binding site for an antisense oligonucleotide, and/or an enhancer. Therefore, placing a gene under the regulatory control of a promoter or a regulatory element means positioning the gene such that the expression of the gene is controlled by the regulatory sequence(s). Thus, in the construction of promoter-gene combinations, the promoter is preferably positioned upstream of the gene and at a distance from the transcription start site that approximates the distance between the promoter and the gene it controls in the natural setting. The variation in this distance can be tolerated without loss of promoter function. Similarly, the preferred positioning of a regulatory element, such as an enhancer, with respect to a heterologous gene placed under its control reflects its natural position relative to the structural gene it naturally regulates. Enhancers are believed to be relatively position and orientation independent in contrast to promoter elements. In some embodiments, the gene regulation sequence comprises one or more of a binding sequence for an antisense oligonucleotide, a binding sequence for doxycycline, or a polynucleotide sequence encoding a riboswitch. In some embodiments, the antisense oligonucleotide (ASO) comprises one or more modified nucleotides. In one embodiment, the antisense oligonucleotide is a morpholino oligonucleotide.

In some embodiments, an antisense oligonucleotide (ASO) described herein comprises from about 8 to about 50 nucleotides in length. In some instances, the ASO comprises from about 8 to about 30, from about 8 to about 25, from about 8 to about 20, from about 8 to about 18, from about 8 to about 15, from about 10 to about 50, from about 10 to about 30, from about 10 to about 25, from about 10 to about 20, from about 10 to about 18, from about 10 to about 15, from about 12 to about 50, from about 12 to about 30, from about 12 to about 25, from about 12 to about 20, from about 12 to about 18, or from about 12 to about 15 nucleotides in length. In some embodiments, the ASO comprises 8, 9, 10, 11, 12, 13, 14, 15, 16, 17, 18, 19, 20, 21, 22, 23, 24, 25, 30, 40, or 50 nucleotides in length.

In some instances, the ASO comprises one or more modified nucleotides. In some instances, the ASO comprises about 5, 10, 20, 30, 40, 50, 60, 70, 80, 90, or 100% modified nucleotides. In other instances, the ASO comprises about 1, 2, 3, 4, 5, 6, 7, 8, 9, 10, 11, 12, 13, 14, 15, 20, 25, 30, 35, 40, or more modified nucleotides. In some instances, the modification is at a 2' hydroxyl group of the ribose moiety. In some instances, the modification includes an H, OR, R, halo, SH, SR, $NH_2$, NHR, $NR_2$, or CN, wherein R is an alkyl moiety. Exemplary alkyl moiety includes, but is not limited to, halogens, sulfurs, thiols, thioethers, thioesters, amines (primary, secondary, or tertiary), amides, ethers, esters, alcohols and oxygen. In some instances, the alkyl moiety further comprises a modification. In some instances, the modification comprises an azo group, a keto group, an aldehyde group, a carboxyl group, a nitro group, a nitroso, group, a nitrile group, a heterocycle (e.g., imidazole, hydrazino or hydroxylamino) group, an isocyanate or cyanate group, or a sulfur containing group (e.g., sulfoxide, sulfone, sulfide, and disulfide). In some instances, the alkyl moiety further comprises a hetero substitution. In some instances, the carbon of the heterocyclic group is substituted by a nitrogen, oxygen or sulfur. In some instances, the heterocyclic substitution includes but is not limited to, morpholino, imidazole, and pyrrolidino. In some instances, the modification at the 2' hydroxyl group is a 2'-O-methyl modification or a 2'-O-methoxyethyl (2'-O-MOE) modification. In some instances, the modified nucleotide is a locked or bridged ribose modification (e.g., locked nucleic acid or LNA), an ethylene nucleic acid (ENA) (e.g., a 2'-4'-ethylene-bridged nucleic acid), a peptide nucleic acid, or a morpholino. In some instances, the modified nucleotide further comprises one or more modified internucleotide linkages. Exemplary modified internucleotide linkage includes, but is not limited to, phosphorothioates, phosphorodithioates, methylphosphonates, 5'-alkylenephosphonates, 5'-methylphosphonate, 3'-alkylene phosphonates, borontrifluoridates, borano phosphate esters and selenophosphates of 3'-5'linkage or 2'-5'linkage, phosphotriesters, thionoalkylphosphotriesters, hydrogen phosphonate linkages, alkyl phosphonates, alkylphosphonothioates, arylphosphonothioates, phosphoroselenoates, phosphorodiselenoates, phosphinates, phosphoramidates, 3'-alkylphosphoramidates, aminoalkylphosphoramidates, thionophosphoramidates, phosphoropiperazidates, phosphoroanilothioates, phosphoroanilidates, ketones, sulfones, sulfonamides, carbonates, carbamates, methylenehydrazos, methylenedimethylhydrazos, formacetals, thioformacetals, oximes, methyleneiminos, methylenemethyliminos, thioamidates, linkages with riboacetyl groups, aminoethyl glycine, silyl or siloxane linkages, alkyl or cycloalkyl linkages with or without heteroatoms of, for example, 1 to 10 carbons that are saturated or unsaturated and/or substituted and/or contain heteroatoms, linkages with morpholino structures, amides, polyamides wherein the bases are attached to the aza nitrogens of the backbone directly or indirectly, and combinations thereof.

The term "morpholino" as used herein refers to a polymeric molecule having a backbone which supports bases capable of forming a hydrogen bond with a polynucleotide. In some embodiments, the polymer on the morpholino lacks a pentose sugar backbone moiety, and more specifically a ribose backbone linked by phosphodiester bonds which is typical of nucleotides and nucleosides. In one embodiment, the morpholino oligonucleotide contains a nitrogen ring. In another embodiment, the morpholino is a stereopure oligonucleotide (e.g., see wavelifesciences.com, last accessed on Jan. 25, 2019) or its derivatives. In another embodiment, the morpholino comprise a sequence at least 95% identical with a stereopure polynucleotide.

In another embodiment, morpholino comprises a structure from about 8 to about 50, from about 8 to about 30, from about 10 to about 50, from about 10 to about 30, or from about 12 to about 30 nucleotides, including a targeting base sequence that is complementary to a target region of a selected preprocessed mRNA or pre-mRNA, such as the intron region of a pre-mRNA. In another embodiment, the morpholino antisense oligonucleotide promotes splicing a target exon, which results in a transcript that lacks the target exon.

In some instances, an antisense oligonucleotide (ASO) is referred to herein as an OncoSkip. As used herein, the term "OncoSkip" refers to an ASO designed to induce skipping of a target exon during splicing of a target transgene, thereby inducing expression of the target transgene. In some instances, the target transgene encodes a polypeptide that binds to a surface polypeptide (e.g., a surface receptor) of a target cell. In some instances, the target cell is a tumor cell or an immune cell. In some instances, the target transgene is an oncogene. In such instances, the use of the OncoSkip induces skipping of a target exon during splicing to induce expression of the oncogene.

In some embodiments, an OncoSkip described herein comprises from about 8 to about 50 nucleotides in length. In some instances, the OncoSkip comprises from about 8 to about 30, from about 8 to about 25, from about 8 to about 20, from about 8 to about 18, from about 8 to about 15, from about 10 to about 50, from about 10 to about 30, from about 10 to about 25, from about 10 to about 20, from about 10 to about 18, from about 10 to about 15, from about 12 to about 50, from about 12 to about 30, from about 12 to about 25, from about 12 to about 20, from about 12 to about 18, or from about 12 to about 15 nucleotides in length. In some embodiments, the OncoSkip comprises 8, 9, 10, 11, 12, 13, 14, 15, 16, 17, 18, 19, 20, 21, 22, 23, 24, 25, 30, 40, or 50 nucleotides in length.

In some embodiments, the OncoSkip comprises one or more modified nucleotides, e.g., comprises about 5, 10, 20, 30, 40, 50, 60, 70, 80, 90, or 100% modified nucleotides. In some instances, the OncoSkip comprises about 1, 2, 3, 4, 5, 6, 7, 8, 9, 10, 11, 12, 13, 14, 15, 20, 25, 30, 35, 40, or more modified nucleotides. In some cases, the OncoSkip comprises one or more morpholino-modified nucleotides. In some cases, the OncoSkip comprises about 5, 10, 20, 30, 40, 50, 60, 70, 80, 90, or 100% morpholino-modified nucleotides. In some cases, the OncoSkip comprises about 1, 2, 3, 4, 5, 6, 7, 8, 9, 10, 11, 12, 13, 14, 15, 20, 25, 30, 35, 40, or more morpholino-modified nucleotides.

In some cases, the OncoSkip works in concert with a TransSkip. As used herein, the term "TransSkip" refers to a recombinant vector (e.g., a recombinant viral vector such as an AAV vector) that comprises a transgene that is interrupted by an intron-exon-intron region, in which the exon comprises a stop codon that prevents normal expression of the transgene-encoded polypeptide. In some instances, the transgene is further encompassed by a construct that comprises a polynucleotide encoding a dimert. In some cases, in conjunction with an OncoSkip, the OncoSkip skips the exon from the intron-exon-intron region during splicing to generate a mRNA which enables expression of the transgene-encoded polypeptide. In the absence of the OncoSkip, the transgene expression from the TransSkip is silenced due to the presence of the stop codon in the intron-exon-intron region.

The term "Adeno-associated virus" or "AAV" as used herein refers to a member of the class of viruses associated with this name and belonging to the genus Dependoparvovirus, family Parvoviridae. Multiple serotypes of this virus are known to be suitable for gene delivery; all known serotypes can infect cells from various tissue types. At least 11 sequentially numbered, AAV serotypes are known in the art. Non-limiting exemplary serotypes useful in the methods disclosed herein include any of the 11 serotypes, e.g., AAV2, AAV8, AAV9, or variant serotypes, e.g., AAV-DJ and AAV PHP.B. The AAV particle comprises three major viral proteins: VP1, VP2, and VP3. In one embodiment, the AAV refers to of the serotype AAV1, AAV2, AAV4, AAV5, AAV6, AAV7, AAV8, AAV9, AAV10, AAV11, AAV12, AAV13, AAV PHP.B, AAV rh74, or AAV-DJ (a chimera obtained by shuffling of eight different AAV wild-types).

The term "isolated" as used herein refers to molecules or biologicals or cellular materials being substantially free from other materials.

As used herein, the term "functional" may be used to modify any molecule, biological, or cellular material to intend that it accomplishes a particular, specified effect.

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically, or biochemically modified, non-natural, or derivatized nucleotide bases.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. Non-limiting exemplary promoters include Rous sarcoma virus (RSV) LTR promoter (optionally with the RSV enhancer), a cytomegalovirus (CMV) promoter, an SV40 promoter, a dihydrofolate reductase promoter, a β-actin promoter, a phosphoglycerol kinase (PGK) promoter, a U6 promoter, or an EF1alpha short form (EFS) promoter.

Additional non-limiting exemplary promoters with certain target specificity are provided herein below including but not limited to cytomegalovirus (CMV), human polypeptide chain elongation factor (EF1a), SV40, phosphoglycerate kinase (PGK) such as PGK1 (human or mouse), P5, Ubc, human beta actin, CAG, TRE, UAS, Ac5, Polyhedrin, CaMKIIa, Gal1, TEF1, GDS, ADH1, CaMV35S, ubiquitin (Ubi) such ubiquitin C (UbiC), H1, U6, Alpha-1-antitrypsin, spleen focus-forming virus (SFFV), and chicken beta-actin (CBA). Synthetically-derived promoters may be used for ubiquitous or tissue specific expression. Further, virus-derived promoters, some of which are noted above, may be useful in the methods disclosed herein, e.g., CMV, HIV, adenovirus, and AAV promoters.

In some embodiments, the promoter is a tissue-specific promoter. In some instances, the tissue-specific promoter is an endogenous promoter, or a promoter that is derived from genes solely expressed in a target cell type. Exemplary tissue specific promoters include, but are not limited to, liver-specific promoters such as ApoE/hAAT, LP1, SV40/hAlb (InvivoGen); photoreceptor-specific promoters such as human rhodopsin kinase (GRK1) and cone arrestin (CAR); B cell specific promoter such as B29 (InvivoGen); haematopoietic cell specific promoter such as CD45 promoter and SV40/CD45 from InvivoGen; muscle cell specific promoter such as desmin promoter (InvivoGen); pancreatic acinar cell specific promoter such as Elastase-1 promoter (InvivoGen); endothelial cell specific promoter such as Flt-1 promoter (InvivoGen); and neuron specific promoter such as SYN1 promoter (InvivoGen).

In some embodiments, the promoter is coupled to an enhancer to increase the transcription efficiency. Non-limiting examples of enhancers include an RSV enhancer, a CMV enhancer, and α-fetoprotein MERIT enhancer.

An enhancer is a regulatory element that increases the expression of a target sequence. A "promoter/enhancer" is a polynucleotide that contains sequences capable of providing both promoter and enhancer functions. For example, the long terminal repeats of retroviruses contain both promoter and enhancer functions. The enhancer/promoter may be "endogenous" or "exogenous" or "heterologous." An "endogenous" enhancer/promoter is one which is naturally linked with a given gene in the genome. An "exogenous" or "heterologous" enhancer/promoter is one which is placed in juxtaposition to a gene by means of genetic manipulation (i.e., molecular biological techniques) such that transcription of that gene is directed by the linked enhancer/promoter.

In some embodiments, a vector utilized herein (e.g., a viral vector such as an AAV vector) further comprises one or more additional regulatory elements. Exemplary regulatory elements include, but are not limited to, transcription terminators, polyadenylation sites, and inverted terminal repeats (ITRs) such as 5' ITR and 3' ITR. In some instances, a regulatory element comprises Woodchuck Hepatitis Virus (WHP) post-transcriptional regulatory element (WPRE).

The term "protein," "peptide," and "polypeptide" are used interchangeably and in their broadest sense to refer to a compound of two or more subunits of amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs, and peptidomimetics.

As used herein, the term "vector" refers to a non-chromosomal nucleic acid comprising an intact replicon such that the vector may be replicated when placed within a cell, for example by a process of transformation. Vectors may be viral or non-viral. Viral vectors include Retroviruses, Adenoviruses, Herpesvirus, Baculoviruses, modified Baculoviruses, Papovavirus, or otherwise modified naturally occurring viruses. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA. In another embodiment, the vector is a recombinant viral vector comprising a backbone vector selected from the group of a retroviral vector, a lentiviral vector, a murine leukemia viral ("MLV") vector, an Epstein-Barr viral ("EBV") vector, an adenoviral vector, a herpes viral ("HSV") vector, or an Adeno-associated viral ("AAV") vector. In another embodiment, the vector is an AAV vector, or optionally a self-complementary AAV vector.

A "viral vector" is defined as a recombinantly produced virus or viral particle that comprises a polynucleotide to be delivered into a host cell, either in vivo, ex vivo or in vitro. Examples of viral vectors include retroviral vectors, AAV vectors, lentiviral vectors, adenovirus vectors, alphavirus vectors and the like. Alphavirus vectors, such as Semliki Forest virus-based vectors and Sindbis virus-based vectors, have also been developed for use in gene therapy and immunotherapy. See, Schlesinger and Dubensky (1999) Curr. Opin. Biotechnol. 5: 434-439 and Ying, et al. (1999) Nat. Med. 5(7): 823-827. In some instances, the viral vector is an AAV vector, e.g., AAV1, AAV2, AAV4, AAV5, AAV6, AAV7, AAV8, AAV9, AAV10, AAV11, AAV12, AAV13, AAV PHP.B, AAV rh74, or AAV-DJ. In some cases, the viral vector is AAV rh74. In some cases, the AAV rh74 comprises the vector sequence with the GenBank accession number LP899424.1 (accessed on Feb. 7, 2020).

In some embodiments, there is a limited carrying capacity for a viral vector (e.g., an AAV vector). For example, an AAV vector has a carrying capacity limit of 4.7 kb. As such, the combination of the dimert along with the promoter, enhancer, and other regulatory elements need to be within the 4.7 kb capacity. In such instances, a promoter utilized herein is selected based on its nucleic acid length to enable packaging of the dimert and other regulatory elements into a viral vector, e.g., an AAV vector. In some cases, the promoter for such use is SFFV, EF1α, PGK, UbiC, CMV, CBA, or EFS. In some cases, the promoter is EFS.

In another embodiment, the promoter is an inducible promoter. In a specific related embodiment, the promoter an inducible tetracycline promoter. The Tet-Off and Tet-On Gene Expression Systems give researchers ready access to the regulated, high-level gene expression systems described by Gossen & Bujard (1992; Tet-Off) and Gossen et al. (1995; Tet-On). In the Tet-Off system, gene expression is turned on when tetracycline (Tc) or doxycycline (Dox; a Tc derivative) is removed from the culture medium. In contrast, expression is turned on in the Tet-On system by the addition of Dox. Both systems permit gene expression to be tightly regulated in response to varying concentrations of Tc or Dox. Maximal expression levels in Tet systems are very high and compare favorably with the maximal levels obtainable from strong, constitutive mammalian promoters such as CMV (Yin et al., 1996). Unlike other inducible mammalian expression systems, gene regulation in the Tet Systems is highly specific, so interpretation of results is not complicated by pleiotropic effects or nonspecific induction. In E. coli, the Tet repressor protein (TetR) negatively regulates the genes of the tetracycline-resistance operon on the Tn10 transposon. TetR blocks transcription of these genes by binding to the tet operator sequences (tetO) in the absence of Tc. TetR and tetO provide the basis of regulation and induction for use in mammalian experimental systems. In the Tet-On system, the regulatory protein is based on a "reverse" Tet repressor (rTetR) which was created by four amino acid changes in TetR (Hillen & Berens, 1994; Gossen et al., 1995). The resulting protein, rtTA (reverse tTA also referred to tetracycline activator protein), is encoded by the pTet-On regulator plasmid.

In a related embodiment, the vector further comprises, or alternatively consists essentially of, or yet further consists of a nucleic acid encoding a tetracycline activator protein; and a promoter that regulates expression of the tetracycline activator protein.

Other inducible systems useful in vectors, isolated cells, viral packaging systems, and methods described herein include regulation by ecdysone, by estrogen, progesterone, chemical inducers of dimerization, and isopropyl-beta-D1-thiogalactopyranoside (EP TG).

As used herein, the term "recombinant expression system" or "recombinant vector" refers to a genetic construct or constructs for the expression of certain genetic material formed by recombination.

A "gene delivery vehicle" is defined as any molecule that can carry inserted polynucleotides into a host cell. Examples of gene delivery vehicles are liposomes, micelles biocompatible polymers, including natural polymers and synthetic polymers; lipoproteins; polypeptides; polysaccharides; lipopolysaccharides; artificial viral envelopes; metal particles; and bacteria, or viruses, such as Baculovirus, Adenovirus and Retrovirus, Bacteriophage, cosmid, plasmid, fungal vectors, and other recombination vehicles typically used in the art which have been described for expression in a variety of eukaryotic and prokaryotic hosts, and may be used for gene therapy as well as for simple protein expression.

A polynucleotide disclosed herein can be delivered to a cell or tissue using a gene delivery vehicle. "Gene delivery," "gene transfer," "transducing," and the like as used herein, are terms referring to the introduction of an exogenous polynucleotide (sometimes referred to as a "transgene") into a host cell, irrespective of the method used for the introduction. Such methods include a variety of well-known techniques such as vector-mediated gene transfer (by, e.g., viral infection/transfection, or various other protein-based, or lipid-based gene delivery complexes) as well as techniques facilitating the delivery of "naked" polynucleotides (such as electroporation, "gene gun" delivery and various other techniques used for the introduction of polynucleotides). The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are known to be capable of mediating transfer of genes to mammalian cells, as is known in the art and described herein.

A "plasmid" is an extra-chromosomal DNA molecule separate from the chromosomal DNA which is capable of replicating independently of the chromosomal DNA. In many cases, it is circular and double-stranded. Plasmids provide a mechanism for horizontal gene transfer within a population of microbes and typically provide a selective advantage under a given environmental state. Plasmids may carry genes that provide resistance to naturally occurring antibiotics in a competitive environmental niche, or alternatively the proteins produced may act as toxins under similar circumstances.

"Plasmids" used in genetic engineering are called "plasmid vectors." Many plasmids are commercially available for such uses. The gene to be replicated is inserted into copies of a plasmid containing genes that make cells resistant to particular antibiotics and a multiple cloning site (MCS, or polylinker), which is a short region containing several commonly used restriction sites allowing the easy insertion of DNA fragments at this location. Another major use of plasmids is to make large amounts of proteins. In this case, researchers grow bacteria containing a plasmid harboring the gene of interest. Just as the bacterium produces proteins to confer its antibiotic resistance, it can also be induced to produce large amounts of proteins from the inserted gene.

In aspects where gene transfer is mediated by a DNA viral vector, such as an Adenovirus (Ad) or Adeno-associated virus (AAV), a vector construct refers to the polynucleotide comprising the viral genome or part thereof, and a transgene. Adenoviruses (Ads) are a relatively well characterized, homogenous group of viruses, including over 50 serotypes. Ads do not require integration into the host cell genome. Recombinant Ad derived vectors, particularly those that reduce the potential for recombination and generation of wild-type virus, have also been constructed. Such vectors are commercially available from sources such as Takara Bio USA (Mountain View, CA), Vector Biolabs (Philadelphia, PA), and Creative Biogene (Shirley, NY). Wild-type AAV has high infectivity and specificity integrating into the host cell's genome. See, Wold and Toth (2013) Curr. Gene. Ther. 13(6): 421-433, Hermonat & Muzyczka (1984) Proc. Natl. Acad. Sci. USA 81: 6466-6470, and Lebkowski et al. (1988) Mol. Cell. Biol. 8: 3988-3996.

Vectors that contain both a promoter and a cloning site into which a polynucleotide can be operatively linked are well known in the art. Such vectors are capable of transcribing RNA in vitro or in vivo, and are commercially available from sources such as Agilent Technologies (Santa Clara, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

The terms "substantially homologous" or "substantially identical" mean a polypeptide or nucleic acid molecule that exhibits at least 50% or greater homology or identity to a reference amino acid sequence (for example, any one of the amino acid sequences described herein) or nucleic acid sequence (for example, any one of the nucleic acid sequences described herein). For example, such a sequence is at least about 60%, about 65%, about 70%, about 75%, about 80%, about 85%, about 90%, about 95%, or about 96%, or about 97%, or about 98%, or about 99% homologous or identical at the amino acid level or nucleic acid to the sequence used for comparison (e.g., a wild-type, or native, sequence). In some embodiments, a substantially homologous or substantially identical polypeptide contains one or more amino acid amino acid substitutions, insertions, or deletions relative to the sequence used for comparison. In some embodiments, a substantially homologous or substantially identical polypeptide contains one or more non-natural amino acids or amino acid analogs, including, D-amino acids, and retroinverso amino, to replace homologous sequences.

Sequence homology or sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. In an exemplary approach to determining the degree of identity, a BLAST program may be used, with a probability score between $e^{-3}$ and $e^{-100}$ indicating a closely related sequence.

As used herein, the term "analog" refers to a structurally related polypeptide or nucleic acid molecule having the function of a reference polypeptide or nucleic acid molecule.

As used herein, the term "a conservative sequence modification" refers to an amino acid modification that does not significantly affect or alter the binding characteristics of the presently disclosed engineered receptor (e.g., the extracellular antigen-binding domain of the engineered receptor) comprising the amino acid sequence. Conservative modifications can include amino acid substitutions, additions, and deletions. Modifications can be introduced into the human scFv of the presently disclosed engineered receptor by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cystine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cystine, glycine, isoleucine, leucine, methionine, phenylalanine, proline, tryptophan, and valine. Thus, one or more amino acid residues within a particular region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence are altered.

A "composition" is intended to mean a combination of active polypeptide, polynucleotide or antibody and another compound or composition, inert (e.g., a detectable label) or active (e.g., a gene delivery vehicle).

A "pharmaceutical composition" is intended to include the combination of an active polypeptide, polynucleotide or antibody with a carrier, inert or active such as a solid support, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

As used herein, the term "cancer" comprises solid tumors and hematologic malignancies. Exemplary solid tumors include, but are not limited to, bladder cancer, bone cancer, brain cancer (e.g., glioblastoma), breast cancer, colorectal cancer, esophageal cancer, eye cancer, head and neck cancer, kidney cancer, lung cancer, melanoma, mesothelioma, ovarian cancer, pancreatic cancer, prostate cancer, or stomach cancer. Exemplary hematologic malignancy include, but are not limited to, acute myeloid leukemia (AML), chronic lymphocytic leukemia (CLL), small lymphocytic lymphoma (SLL), follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis. In some instances, the cancer is a metastatic cancer (e.g., a metastatic solid tumor or metastatic hematologic malignancy). In some instances, the cancer is a relapsed or refractory cancer (e.g., a relapsed or refractory solid tumor or a relapsed or refractory hematologic malignancy).

In some embodiments, the cancer is characterized with an upregulated expression of fibroblast activation protein (FAP) (in which the amino acid sequence of the human FAP is disclosed in GenPept Accession Number 138593, accessed on Feb. 10, 2020). FAP, also known as FAP-alpha and prolyl endopeptidase FAP, is a membrane-bound glycoprotein and part of the dipeptidyl peptidase (DPP) family. FAP has both post-proline exopeptidase activity and gelatinase activity. In some instances, cancers that are characterized with an upregulated expression of FAP (FAP-positive cancers) include, but are not limited to, bone cancer, brain cancer, breast cancer, colorectal cancer, esophageal cancer, gastric cancer, liver cancer, lung cancer, oral cancer, ovarian cancer, pancreatic cancer, parathyroid cancer, and renal cancer. In some instances, the FAP-positive cancers comprise a high level of fibrosis. In some instances, this level is compared to an equivalent cancer in which FAP is not upregulated. In additional instances, this level is compared to a fibrosis level of a normal subject. In some aspects, the cancer cells are characterized as expressing SLC7A11 or a homolog thereof.

As used herein, "first-line therapy" comprises a primary treatment for a subject, optionally a subject with a cancer. In some instances under a cancer setting, the cancer is a primary cancer. In other instances, the cancer is a metastatic or recurrent cancer. In some cases, the first-line therapy comprises chemotherapy. In other cases, the first-line treatment comprises radiation therapy. A skilled artisan would readily understand that different first-line treatments may be applicable to different type of cancers.

As used herein, a second-line therapy encompasses treatments that are utilized after the primary or first-line treatment stops. A third-line therapy, a fourth-line therapy, or a fifth-line therapy encompass subsequent treatments. As indicated by the naming convention, a third-line therapy encompass a treatment course upon which a primary and second-line therapy have stopped.

A "subject" of diagnosis or treatment is a cell or an animal such as a mammal, or a human. A subject is not limited to a specific species and includes non-human animals subject to diagnosis or treatment and are those subject to infections or animal models, for example, simians, murines, such as, rats, mice, chinchilla, canine, such as dogs, leporids, such as rabbits, livestock, sport animals, and pets. Human patients are included within the term as well.

The term "tissue" is used herein to refer to tissue of a living or deceased organism or any tissue derived from or designed to mimic a living or deceased organism. The tissue may be healthy, diseased, and/or have genetic mutations. The biological tissue may include any single tissue (e.g., a collection of cells that may be interconnected) or a group of tissues making up an organ or part or region of the body of an organism. The tissue may comprise a homogeneous cellular material or it may be a composite structure such as that found in regions of the body including the thorax which for instance can include lung tissue, skeletal tissue, and/or muscle tissue. Exemplary tissues include, but are not limited to those derived from liver, lung, thyroid, skin, pancreas, blood vessels, bladder, kidneys, brain, biliary tree, duodenum, abdominal aorta, iliac vein, heart and intestines, including any combination thereof.

As used herein, the term "specifically binds" or "specifically binds to" or "specifically target" is meant a polypeptide or fragment thereof that recognizes and binds a biological molecule of interest (e.g., a polypeptide), but which does not substantially recognize and bind other molecules in a sample, for example, a biological sample, which includes or expresses a tumor antigen.

As used herein, "treating" or "treatment" of a disease in a subject refers to (1) preventing the symptoms or disease from occurring in a subject that is predisposed or does not yet display symptoms of the disease; (2) inhibiting the disease or arresting its development; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. In one aspect, the term "treatment" excludes prevention.

As used herein the term "effective amount" intends to mean a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions. In the context of gene therapy, in some embodiments the effective amount is the amount sufficient to result in regaining part or full function of a gene that is deficient in a subject. In other embodiments, the effective amount of a recombinant polynucleotide, vector or an AAV viral particle is the amount sufficient to result in expression of a gene in a subject. In some embodiments, the effective amount is the amount required to increase galactose metabolism in a subject in need thereof. The skilled artisan will be able to determine appropriate amounts depending on these and other factors.

In some embodiments the effective amount will depend on the size and nature of the application in question. It will also depend on the nature and sensitivity of the target subject and the methods in use. The skilled artisan will be able to determine the effective amount based on these and other considerations. The effective amount may comprise one or more administrations of a composition depending on the embodiment.

As used herein, the term "administer" or "administration" intends to mean delivery of a substance to a subject such as an animal or human. Administration can be effected in one dose, continuously or intermittently throughout the course of treatment. Methods of determining the most effective means and dosage of administration are known to those of skill in the art and will vary with the composition used for therapy, the purpose of the therapy, as well as the age, health or gender of the subject being treated. Single or multiple administrations can be carried out with the dose level and pattern being selected by the treating physician or in the case of pets and animals, treating veterinarian. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated and the target cell or tissue. Non-limiting examples of route of administration include intravenous, intra-arterial, intramuscular, intracardiac, intrathecal, subventricular, epidural, intracerebral, intracerebroventricular, sub-retinal, intravitreal, intraarticular, intraocular, intraperitoneal, intrauterine, intradermal, subcutaneous, transdermal, transmucosal, and inhalation.

Sequences of the Disclosure

The sequences utilized in the present disclosure are defined in the sequence listing. The below Table 1 details SEQ ID NOs:1-38 as the related to the present disclosure.

TABLE 1

| Polypeptide and Polynucleotide Sequences of the Disclosure | | |
|---|---|---|
| SEQ ID NO | Description | Sequence |
| 1 | Exon 7 antisense oligo SLC7A11 exon7_55 | CCAACTTGGACTTACCACTGCCACT |
| 2 | Exon 7 antisense oligo | ATTTTGGGAACTTGGACTTACCACTGCCACTGCCACTGCC |
| 3 | Exon 7 antisense oligo (subsequence of SEQ ID NO: 2) | ACTTACCACTGCCACTGCCACTGCC |
| 4 | Exon 7 antisense oligo (subsequence of SEQ ID NO: 2) | ATTTTGGGAACTTGGACTTACCACTGC |
| 5 | Exon 7 antisense oligo (subsequence of SEQ ID NO: 2) | ACCACTGCCACTGCCACTGCC |
| 6 | Exon 7 antisense oligo (subsequence of SEQ ID NO: 2) | CTGCCACT |
| 7 | Exon 7 antisense oligo (subsequence of SEQ ID NO: 2) | CCACTGCCACT |
| 8 | Exon 7 antisense oligo (subsequence of SEQ ID NO: 2) | TGGACTTACCACTGCC |
| 9 | Exon 7 antisense oligo (subsequence of SEQ ID NO: 2) | GGAACTTGGACTTACCACTGCCAC |
| 10 | Exon 7 antisense oligo (subsequence of SEQ ID NO: 2) | ATTTTGGGAACTTGGACTTACCACTG |
| 11 | Exon 7 antisense oligo (subsequence of SEQ ID NO: 2) | GAACTTGGACTTACCACTG |
| 12 | Exon 9 antisense oligo SLC7A11 exon9_55 | ATATACTTGTTAATATGCATTACCA |
| 13 | Exon 9 antisense oligo | ATATACTTGTTAATATGCATTACCAAAACAATAAC |
| 14 | Exon 9 antisense oligo (subsequence of SEQ ID NO: 13) | ATGCATTACC |
| 15 | Exon 9 antisense oligo (subsequence of SEQ ID NO: 13) | GCATTACC |
| 16 | Exon 9 antisense oligo (subsequence of SEQ ID NO: 13) | TAATATGCATTACCA |

TABLE 1-continued

Polypeptide and Polynucleotide Sequences of the Disclosure

| SEQ ID NO | Description | Sequence |
|---|---|---|
| 17 | Exon 9 antisense oligo (subsequence of SEQ ID NO: 13) | CTTGTTAATATGCATTAC |
| 18 | Exon 9 antisense oligo (subsequence of SEQ ID NO: 13) | CTTGTTAATATGCATTACCAAAC |
| 19 | Exon 9 antisense oligo (subsequence of SEQ ID NO: 13) | GTTAATATGCATTACCAAAAC |
| 20 | Exon 9 antisense oligo (subsequence of SEQ ID NO: 13) | AATATGCATTACCAA |
| 21 | Exon 9 antisense oligo (subsequence of SEQ ID NO: 13) | GCATTACCAAAAC |
| 22 | Exon 9 antisense oligo (subsequence of SEQ ID NO: 13) | TACCAAAACAATAAC |
| 23 | Exon 7 of SLC7A11 | AACCATTCCCCTTGCAATATGTATATCCATGGCCATTGTCACCATTGGCTATGTGCTGAC |
| 24 | 5' fragment of intron adjacent to 3' end of Exon 7 of SLC7A11 | gtaagtccaagttgggaaaatgcca |
| 25 | Exon 9 of SLC7A11 | GTTATTCTATGTTGCGTCTCGAGAGGGTCACCTTCCAGAAATCCTCTCCATGATTCATGTCCGCAAGCACACTCCTCTACCAGCTGTTATTGTTTTG |
| 26 | 5' fragment of intron adjacent to 3' end of Exon 9 of SLC7A11 | gtaatgcatattaacaagtatatct |
| 27 | Combination of SEQ ID NOs: 23 & 24 | AACCATTCCCCTTGCAATATGTATATCCATGGCCATTGTCACCATTGGCTATGTGCTGACgtaagtccaagttgggaaaatgcca |
| 28 | Combination of SEQ ID NOs: 25 & 26 | GTTATTCTATGTTGCGTCTCGAGAGGGTCACCTTCCAGAAATCCTCTCCATGATTCATGTCCGCAAGCACACTCCTCTACCAGCTGTTATTGTTTTGgtaatgcatattaacaagtaatct |
| 29 | SLC7A11 long isoform mRNA (coding for a protein) | See sequence listing |
| 30 | SLC7A11 long isoform polypeptide sequence | See sequence listing |
| 31 | SLC7A11 short isoform mRNA missing exon 7 | See sequence listing |
| 32 | SLC7A11 short isoform mRNA missing exon 7 and 9 | See sequence listing |

TABLE 1-continued

Polypeptide and Polynucleotide Sequences of the Disclosure

| SEQ ID NO | Description | Sequence |
|---|---|---|
| 33 | GFP-3xFLAG | See sequence listing |
| 34 | LUC7L-3xFLAG | See sequence listing |
| 35 | LUC7L2-3xFLAG | See sequence listing |
| 36 | LUC7L3-3xFLAG | See sequence listing |
| 37 | SLC7A11-HA | See sequence listing |
| 38 | PFKM | See sequence listing |

Interfering Oligonucleotides—Antisense, siRNA, miRNA

As used herein, the term "antisense oligonucleotide (AO)" refers to a single-stranded oligonucleotide that is specific for, and complementary to, a splicing sequence of interest, and accordingly is capable of hydrogen bonding to the sequence. One of skill in the art can readily design AOs to be specific for suitable target sequences, many of which are well-known in the art. For example, one can access pre-mRNA sequences comprising suitable splicing sequences in publications or in annotated, publically available databases, such as the GenBank database operated by the NCBI. A skilled worker will be able to design, make and use suitable antisense oligonucleotides, based on these or other sequences, without undue experimentation. A number of AO's have been designed for enhancing exon skipping and some are currently in preclinical or clinical trials. Any of these AOs is suitable for use in a method of the invention.

An antisense nucleic acid may be, e.g., an oligonucleotide, or a nucleic acid comprising an anti sense sequence that is operably linked to an expression control sequence and that is expressed in a cell.

Antisense oligonucleotides may have a variety of different backbone chemistries, such as morpholino phosphorodiamidate (PMO) or 2'-O-methyl' or peptide nucleic acids, etc., which stabilize them. For example, it can be DNA, RNA, PNA or LNA, or chimeric mixtures or derivatives or modified versions thereof. The nucleic acid can be modified at the base moiety, sugar moiety, or phosphate backbone, using conventional procedures and modifications. Modifications of the bases include, e.g., methylated versions of purines or pyrimidines. Modifications may include other appending groups that will be evident to a skilled worker. See, U.S. Pat. No. 10,188,633.

Anti sense oligonucleotides can be constructed using chemical synthesis procedures known in the art. An AO can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used.

For guidance in methods of synthesizing morpholino AO's for use in the present invention, see, e.g., US patent application 2009/0131624 ("Synthesis of morpholino oligomers using double protecte guanine morpholino subunits").

For guidance in synthesizing oligonucleotides, see, e.g., Gough et al. (1979) Nucleic Acids Research 7, 1955-1964; Hata et al. (1983) Tetrahedron Lett. 24, 2775-2778; Jones et al. (1982A Tetrahedron Lett. 23, 2253-2256 Jones et al. (1982) Tetrahedron Lett. 23, 2257-2260 O. Mitsunobu (1981) Synthesis 1, 1-28; Reese et al. (1981) Tetrahedron Lett. 22, 4755-4758; Reese et al. (1984) J. Chem. Soc., Perkin Trans. 111263-1270; Summerton et al. (1993) U.S. Pat. No. 5,185,444; Summerton et al. (1997) Antisense Nucl. Acid Drug Dev. 7(3), 187-195.

For guidance in synthesizing 2-O-methyl' oligos, see e.g. Verma et al. (1998) MODIFIED OLIGONUCLEOTIDES: Synthesis and Strategy for Users, Annu. Rev. Biochem. 67, 99-134

For guidance in synthesizing dantrolene, see e.g. Oleinik et al. (1984) Pharmaceutical Chemistry Journal 18 (5), 3110-312.

To enhance exon skipping in cells in culture, AO's can be added to cells in culture media. Typically, synthetic oligonucleotides are added to a final concentration of about 10 nM to about 10 microM, e.g., about 50 nM to about 1000 nM (e.g., at increments of 10 nM within the indicated ranges). The term "about" a particular value, as used herein, means plus or minus 10% of the indicated value.

Effective doses of AOs for in vivo administration can be determined, e.g., on the basis of the amounts used for exon skipping in the absence of a small molecule of the present invention. Many AO's have been administered to subjects in the absence of small molecule compounds of the invention, and doses have been established which are at least partially effective and are nontoxic to the subjects. In general, doses of AOs ranging from about 5-100 mg/kg/wk IV (intravenous) (or comparable amounts for other modes of admin) are effective for inducing at least a detectable amount of dystrophin expression with targeted removal of a given exon.

Alternatively, an antisense oligonucleotide can be produced biologically using an expression vector into which a nucleic acid has been subcloned in an antisense orientation (i.e., nucleic acid transcribed from the inserted nucleic acid will be of an antisense orientation to a target sequence of interest). Expression control sequences (e.g., regulatory sequences) operatively linked to a nucleic acid cloned in the antisense orientation can be chosen which direct the expression of the antisense RNA molecule in a cell of interest. For instance, promoters and/or enhancers or other regulatory sequences can be chosen which direct constitutive, tissue specific or inducible expression of an AO. Inducible expression of antisense RNA, regulated by an inducible eukaryotic regulatory system, such as the Tel system (e.g., as described err Gossen et al. (1992) *Proc. Natl. Acad. Sci. USA* 89, 5547-5551; Gossen et al. (1995) *Science* 268, 1766-1769; PCT Publication No. WO 94/29442; and PCT Publication No. WO 96/01313) can be used. The antisense expression vector can be in the form of, for example, a recombinant phagemid or attenuated virus. Suitable viral vectors include, adeno-associated virus (ANY) or lentivirus vectors. The antisense expression vector can be introduced into cells using standard techniques well known in the art. For guidance in using AAV vectors for introducing antisense molecules into mdx mice, see e.g. Denti et at (2008) *Hum Gene Ther* 19, 601-608 or Incitti et al. (2010) *Mol. Ther.* 18, 1675-1682.

In one embodiment of the invention, an RNA molecule that comprises the sequence antisense to a splicing sequence in, e.g., the dystrophin pre-mRNA, is produced biologically by using an expression vector into which a nucleic acid has been subcloned. Expression control sequences (e.g. regulatory sequences) operably linked to the cloned nucleic acid can be chosen which direct the expression of the antisense RNA molecule comprising the sequence antisense to a splicing sequence in, e.g., dystrophin pre-mRNA, in a cell of interest. The RNA molecule may, comprise, e.g., a U1 snRNA, U2 snRNA, U6 snRNA or U7 snRNA. Without wishing to be limited by any particular mechanism, it is suggested that expression of the snRNA generates an snRNP particle which then hinds to the target sequence in dystrophin pre-mRNA via the complementary fragment of snRNA. Any of the types of expression control sequences described in the previous paragraph can be used to direct the expression of the desired RNA in this embodiment.

In one embodiment of the invention, an AO comprises a strand that is completely complementary (100% identical in sequence) to a splicing sequence that it is designed to inhibit. That is, every contiguous nucleotide in the AO is hybridized to every nucleotide in a splicing sequence. However, 100% sequence identity between the AO and the target splicing sequence is not required to practice the present invention. Thus, the invention has the advantage of being able to tolerate naturally occurring sequence variations that might be expected due to genetic mutation, strain polymorphism, or evolutionary divergence. Alternatively, the variants may be artificially generated. Nucleic acid sequences with, e.g., small insertions, deletions, and single point mutations relative to the target sequence can be effective for inhibition. The degree of sequence identity can be, e.g., 95%, 98%, 99%, or 100%. Such a variant AO must, of course, retain the relevant activity of the AO from which it is derived. (e.g., the ability to suppress splicing at a site of interest). Such variants are sometimes referred to herein as "active variants."

The length of an AO may vary, provided that it is capable of binding selectively to the intended splicing sequence within the pre-mRNA molecule. A skilled worker can readily determine a satisfactory length. Generally, an AO is from about 10 lit in length to about 50 nt in length. Any length of nucleotides within this range, including the endpoints, can be used in a method of the invention. In one embodiment, the length of the AO is about 17-30 nt in length.

For further guidance for designing suitable antisense molecules that are complementary to a region of a pre-mRNA involved in splicing (thereby blocking splicing), and for methods for making and delivering such molecules to a cell or a subject, see, e.g., US 2008/0200409 or U.S. Pat. No. 7,973,015, 7,960,541, 7,902,160, 7,888,012, 7,879,992 or 7,737,110.

A method of the invention can be carried out in vitro (e.g., to elucidate the mechanism by which splicing occurs, such as to reveal novel molecular interactions in the processing of mRNA; or to screen for compounds that can block a splicing event and thus, for example, enhance exon skipping).

In some aspects, the disclosure is directed to modulating pre-mRNA, mRNA, and the corresponding proteins associated of human SLC7A11, which is a cystine/glutamate antiporter. SLC7A11 is largely produced by various cancer cells, but there are various diseases and conditions discussed herein that indicate that SLC7A11 is expressed in more cell types than just uncontrolled cancer cells. However, genetic ablation of SLC7A11 in mice has demonstrated that the modification is remarkably well tolerated, and complete SLC7A11 −/− mice are viable and fertile. See Arensman et al. (2019) *PNAS*, 116(19):9533-9542. Thus, the genetic or gene expression interventions described herein are expected to have few or no side effects, and certainly no deleterious outcomes in the cells in which the interventions are carried out. In contrast, there are drugs, such as sulfasalazine, that are capable of inhibiting the activity of SLC7A11, however, these drugs have side effects that may result in problematic treatment outcomes.

SLC7A11 is not a transitory name for the gene, rather it is the short form symbol assigned by the HUGO Gene Nomenclature Committee (HGNC) at the European Bioinformatics Institute. SLC7A11, a gene, encodes two spice variants, a short isoform and a long isoform. The long isoform, also defined as ENST00000280612.9, results in a 501 amino acid that exhibits cystine/glutamate antiporter activity. The protein translated from the long isoform is defined as as UniProt Accession Q9UPY5. The SLC7A11 short isoform, which is also called ENST00000509248.1, is predicted to undergo nonsense mediated decay. SLC7A11 is also referred to as xCT.

The short isoform may result in no protein at all, but it is unknown whether the short isoform is translated or not. Production of the short isoform drastically increases in LUC7L2$^{KO}$ cells. The SLC7A11 short isoform is the result of alternative splicing of the pre-mRNA of SLC7A11 as it is processed to mRNA. The short isoform lacks exons 7 and 9 out of the 12 total exons that occur in the long isoform. While the state of the art indicates that there are only two isoforms, the exon silencing of just exon 7 or just exon 9 each yields a different short isoform. Thus, the present disclosure utilizes exon skipping mechanisms to create three distinct short isoforms of SLC7A11 mRNA.

The ability to force the pre-mRNA SLC7A11 to form the short isoform is achieved with exon skipping. In the present case, an antisense oligonucleotide is targeted to the junction in the pre-mRNA between 3' end of exon 7 and the immediately adjacent 5' end of the corresponding intron. This results in exon skipping of exon 7 during the process of splicing to produce the mRNA, meaning that the resulting mRNA does not comprise exon 7. An identical process is carried out to skip exon 9, wherein an antisense oligonucleotide is targeted to the junction in the pre-mRNA between 3' end of exon 9 and the immediately adjacent 5' end of the corresponding intron. This results in exon skipping of exon 9 during the process of splicing to produce the mRNA, meaning that the resulting mRNA does not comprise exon 9. Exon skipping can be used to create mRNA that lacks only exon 7, lacks only exon 9, or lacks both exons 7 and 9.

In some aspects, the 5' splice site (occurring at the 5' terminus of the exons) of exon 7 and or exon 9 is targeted with an antisense oligonucleotide to achieve an mRNA that lacks exon 7 and/or exon 9. The method in which the 5' splice site is targeted is the same as the method for targeting the 3' splice site, only the sequences differ. In some aspects, the antisense oligonucleotide targets a region comprising the 3' end of the intron that is adjacent to the 5' end of the exon 7. In some aspects, the antisense oligonucleotide targets a region comprising the 3' end of the intron that is adjacent to the 5' end of the exon 9. In some aspects, the antisense oligonucleotide overlays the splice site, a portion of the 5' end of the exon, and a portion of the 3' end of the corresponding intron. In some aspects, the antisense oligonucleotide overlays the splice site, one or more nucleotides of the 5' end of the exon, and one or more nucleotides of the 3' end of the corresponding intron.

In some aspects, the antisense oligonucleotides of SEQ ID NO:1-11 are capable of targeting exon 7 for exon skipping. In some aspects, the antisense oligonucleotides are single stranded. In some aspects, the antisense oligonucleotides are double stranded. Exon 7 consists of SEQ ID NO:23. The 5' end of the intron fragment of SEQ ID NO:24, immediately follows exon 7. The junction and the immediately surrounding nucleotides is the location being targeted with antisense oligonucleotides to induce exon skipping of exon 7.

In some aspects, the antisense oligo nucleotides of SEQ ID NO:12-22 are capable of targeting exon 9 for exon skipping. In some aspects, the antisense oligonucleotides are single stranded. In some aspects, the antisense oligonucleotides are double stranded. Exon 9 consists of SEQ ID NO:25. The 5' end of the intron fragment of SEQ ID NO:26, immediately follows exon 9. The junction and the immediately surrounding nucleotides is the location being targeted with antisense oligonucleotides to induce exon skipping of exon 9.

In some aspects, the entire length of the antisense oligonucleotide hybridizes to the target pre-mRNA sequence. In some aspects, one of the nucleotides of the antisense oligonucleotide does not hybridize with the target pre-mRNA sequence. In some aspects, 1, 2, 3, 4, 5, 6, 7, 8, 9, or 10 of the nucleotides of the antisense oligonucleotide does not hybridize with the target pre-mRNA. In some aspects, less than 10, less than 9, less than 8, less than 7, less than 6, less than 5, less than 4, less than 3, or less than 2 nucleotides of the antisense oligonucleotide do not hybridize with the target pre-mRNA. In some aspects, 99%, 98%, 97%, 96%, or 95% of the nucleotides of the antisense oligonucleotide hybridize with the target pre-mRNA sequence.

In some aspects, the antisense oligonucleotide sequence is 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides in length. In some aspects, the antisense oligonucleotide sequence In some aspects, the antisense oligonucleotide hybridizes to a sequence comprising the 3' junction of exon 7 or exon 9 and the corresponding intron to induce exon skipping of exon 7 or exon 9.

In some aspects, the antisense oligonucleotides hybridize to the nucleotides 5' upstream of the junction, wherein one end of the oligo is separated from the junction by less than 10, less than 9, less than 8, less than 7, less than 6, less than 5, less than 4, less than 3, or less than 1 nucleotide. In some aspects, the antisense oligonucleotides hybridize to the nucleotides 3' downstream of the junction, wherein one end of the oligo is separated from the junction by less than 10, less than 9, less than 8, less than 7, less than 6, less than 5, less than 4, less than 3, or less than 1 nucleotide.

In some aspects, the antisense oligonucleotides hybridize to nucleotides on both sides of the junction. In some aspects, the antisense oligonucleotides hybridize to nucleotides on both sides of the junction, such that the oligonucleotide spans at least 1, at least 2, at least 3, at least 4, at least 5, at least 6, at least 7 at least 8, at least 9, at least 10, at least 11, at least 12, at least 13, at least 14, or at least 15 nucleotides over both sides of the junction.

In some aspects, the antisense oligonucleotide is a synthetic oligonucleotide. In some aspects, the antisense oligonucleotide is an artificial oligonucleotide. In some aspects, the antisense oligonucleotide is a non-naturally occurring oligonucleotide. In some aspects, the antisense oligonucleotide is modified to comprise a non-nucleotide moiety, molecule, or protein.

In some aspects, other interfering oligonucleotides can be utilized to achieve the same effects as antisense oligonucleotides. In some aspects, RNAi oligonucleotides are utilized to target the pre-mRNA for exon skipping. In some aspects, the RNAi is a small interfering RNA (siRNA). In some aspects, the RNAi is a microRNA (miRNA).

In another embodiment of the invention, the method is carried out in a subject, in vivo. A "subject," as used herein, can refer to any animal which is subject to a disease or condition that can be treated by a method of the invention. Suitable subjects include, e.g., a mammal, such as an experimental animal or disease model, a farm animal, pet, or the like. In some embodiments, the animal is a primate, for example a human.

In some embodiments of the invention, a subject is treated with an effective amount of a compound of the invention, or with a combination of a compound of the invention and a suitable AO, each of which is designed to block a splicing event of interest. An "effective amount" of a compound (or combination) of the invention is an amount that is effective to elicit a measurable amount of biological activity, e.g. a measurable amount of enhancement of exon skipping (in some embodiments in the absence of AOs, and in some embodiments in the presence of a suitable AO). Preferably, an effective amount of a compound or combination of the invention does not elicit substantial amounts of undesirable (e.g., toxic) effects. The enhancement can occur prophylactically (e.g. preventively, to inhibit the development of the disorder), or in a subject who already has the condition. For example, treatment by a method of the invention can ameliorate one or more symptoms of the condition.

A skilled worker will recognize a variety of conditions that can be treated by a method of the invention. A probabilistic analysis indicated that over 60% of human disease-causing, mutations affect splicing rather than directly affecting coding sequences (Lopez-Biggs et al. (2005) *FEBS Letters* 579, 1900-3). See also Wang et al. (2007), Splicing in disease: disruption of the splicing code and the decoding machinery, *Nature Reviews Genetics* 8, 749-761 and Singh et al. (2012), Pre-mRNA splicing in disease and therapeutics, *Trends in Molecular Medicine* 18, (8), 472-482. Diseases associated with aberrant splicing or missplicing that can be inhibited by a method of the invention include e.g. beta-thalassemia and certain forms of cancers. Alternatively, exon skipping by a method of the invention can remove exons that contain mutations which are associated with diseases, such as mutations that alter the reading frame of the protein encoded by an mRNA. These conditions include, e.g., DMD, as described above (changing DMD dystrophin to a more functional form of dystrophin, in effect converting Duchenne MD into Becker MD). One embodiment of the invention is a method for treating a subject that has Duchenne muscular dystrophy (MID), or is a non-human model of MAD, comprising administering to the subject an effective amount of small molecule selected from the compounds shown in Table 1, in conjunction with an AO specific for modulating splicing of dystrophin pre-mRNA, such as one for exon 23, 44, 45, 50, 51, 52, or 53 of the DMD gene. The exon skipping can be either single or multi-exon skipping (e.g., skipping of many possible 2-10 exon combinations that will be evident to a skilled worker).

In embodiments of the invention, a compound of the invention is administered to a subject, e.g. as part of an adjuvant treatment, or is contacted (e.g., in vitro) with a pre-mRNA target of interest, in conjunction with a suitable AO that is designed to specifically block a splicing event of interest. "In conjunction with" means that the AO can be administered before, or at the same time as, or after, the compound, and that the two components can be administered in separate delivers' vehicles or in the same delivery vehicle. The two agents can be administered with the same, or different, dosage regimens. As used herein, the singular forms "a," "an," and "the" include plural referents unless the context clearly dictates otherwise. For example, "an" AO, as used above, means one or more AO molecules, which can be the same or different.

A number of considerations are generally taken into account in designing delivery systems, routes of administration, and formulations for compounds or combinations of compounds and an AO of the invention. The appropriate delivery system for an agent of the invention will depend upon its particular nature, the particular clinical application, and the site of drug action. One skilled in the art can easily determine the appropriate dose, schedule, and method of administration for the exact formulation of the composition being used, in order to achieve the desired response in the individual patient.

Any of a variety of conventional methods can be used to introduce AOs and/or small molecules of the invention into cells, in vitro or in vivo. These methods include, for example, transfection, electroporation, hydrodynamic "high pressure" delivery, nanoparticle delivery, liposomes, colloidal dispersal systems, or other methods known in the art. Intracellular AO delivery can be enhanced by conjugating cell penetrating peptides to the AO using methods and compounds known in the art. See, e.g., U.S. Pat. No. 7,468,418 and PCT publications WO2009/005793 and WO2009/147368.

Compounds and AO's can be administered (delivered) to a subject by the same or by different modes of administration. Suitable modes of administration include, e.g., subcutaneous, intramuscular, intravenous, oral, intranasal, cutaneous, or suppository routes, depending on the formulation, the compound, and the condition to be treated. Compounds and AO's of the invention may be delivered via a variety of routes including all of the above routes, in dosing patterns that can be optimized with routine, conventional methods. In one embodiment, the compounds are administered chronically to subjects (patients) in conjunction with therapeutic antisense oligonucleoties. In some embodiments, a compound of the invention is administered frequently (e.g., daily or more frequently) to augment less frequent (e.g., monthly or weekly) administration, such as by intravenous or subcutaneous injection, of AO.

Formulations for delivery by a particular method (e.g., solutions, buffers, and preservatives) can be optimized by routine, conventional methods that are well-known in the art. See, e.g., Remington's Pharmaceutical Sciences, 18$^{th}$ edition (1990, Mack Publishing Co., Easton, Pa.), for guidance in suitable formulations.

An "effective" dose of an agent of the invention (either a compound, or a compound in conjunction with an AO, or the AO), or composition thereof, is a dose that, when administered to an animal, particularly a human, in the context of the present invention, is sufficient to effect at least a detectable amount of a therapeutic response in the individual over a reasonable time frame.

The exact amount of the dose (of a small molecule of the invention, used alone or in conjunction with an AO, or of the AO), will vary from subject to subject, depending on the species, age, weight and general condition of the subject, the severity or mechanism of any disorder being treated, the particular agent or vehicle used, its mode of administration and the like. The dose will also be a function of the exon that is being skipped/removed from the mature RNA and the sequence of the AO. The dose used to achieve a desired effect in vivo will be determined by the potency of the particular agent employed, the pharmacodynamics associated with the agent in the host, the severity of the disease state of infected individuals, as well as, in the case of systemic administration, the body weight and age of the individual. The size of the dose also will be determined by the existence of any adverse side effects that may accompany the particular inhibitory agent, or composition thereof, employed. It is generally desirable, whenever possible, to keep adverse side effects to a minimum.

For example, a dose of a small molecule of the invention can range from about 4-10 mg/kg/day, or can be higher or lower. In general, the dose of a small molecule of the invention is one, or close to one, which has been shown to be safe for subjects, such as human patients. Dantrolene, for example, has been shown to be safe when administered to humans up to 8 mg/kg/day during long term administration. Suitable oral doses of Dantrolene include doses of about 4-10, e.g. about 6-8, mg/kg/day. An example herein shows a functional benefit (wire hang test in mdx mice) using 10 mg/kg/week of the oligo AON23 and dantrolene at 10 mg/kg/day compared to 10 mg/kg/week of the AON23 alone (p=0.022).

Dosages for administration of a therapeutic agent of the invention can be in unit dosage form, such as a tablet or capsule. The term "unit dosage form" as used herein refers to physically discrete units suitable as unitary dosages for human and animal subjects, each unit containing a predetermined quantity of an inhibitor of the invention, alone or in combination with other therapeutic agents, calculated in an amount sufficient to produce the desired effect in association with a pharmaceutically acceptable diluent, carrier, or vehicle.

Human cells express a number of unique chimeric mitochondrial RNA molecules. These molecules are non-coding (i.e., they are not known to serve as a template for the translation of a protein) and comprise the 16S mitochondrial ribosomal RNA covalently linked at the 5' end to an inverted repeat sequence. Chimeric mitochondrial RNA molecules are found in two forms: sense and antisense.

The sense chimeric non-coding mitochondrial RNA (SncmtRNA) molecule corresponds to the 16S mitochondrial ribosomal RNA transcribed from the "H-strand" of the circular mitochondrial genome. Covalently linked to the 5' end of this RNA molecule is a nucleotide sequence or inverted repeat sequence corresponding to an RNA transcribed from the "L-strand" of the mitochondrial 16S gene. The size of the inverted repeat sequence in the SncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, or 800 nucleotides or more to between about 100-200, 150-250, 200-300, 250-350, 400-500, 450-550, 500-600, 550-650, 600-700, 650-750, or 700-800 nucleotides or more, including any number in between these values.

The antisense chimeric non-coding mitochondrial RNA (ASncmtRNA) molecule corresponds to the 16S mitochondrial ribosomal RNA transcribed from the "L-strand" of the circular mitochondrial genome. Covalently linked to the 5' end of this RNA molecule is a nucleotide sequence or the inverted repeat sequence corresponding to an RNA transcribed from the "H-strand" of the mitochondrial 16S gene. The size of the inverted repeat sequence in the ASncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800 nucleotides or more to between about 100-200, 150-250, 200-300, 250-350, 400-500, 450-550, 500-600, 550-650, 600-700, 650-750, or 700-800 or more, including any number in between these values.

Further information related to chimeric mitochondrial RNA molecules can be found in U.S. Pat. No. 8,318,686, the disclosure of which is incorporated by reference herein in its entirety.

In one aspect, the invention provides one or more oligonucleotide complementary to an ASncmtRNA molecule or a SncmtRNA molecule, wherein the oligonucleotide is able to hybridize with the chimeric mitochondrial RNA molecules to form a stable duplex for use in a method disclosed herein. In some aspects, provided herein are methods for suppressing metastasis of a cancer in an individual using one or more oligonucleotides described herein. In some aspects, provided herein are methods for treating or preventing relapse of a cancer in an individual. In some aspects, provided herein are methods for treating metastatic cancer in an individual. In some embodiments herein, the individual has been previously treated for cancer with a therapy (e.g., chemotherapy, radiation therapy, surgery or combinations thereof). In some embodiments, the one or more oligonucleotide complementary to an ASncmtRNA molecule or a SncmtRNA molecule described herein has or more of the following characteristics when used in a method disclosed herein: (1) hybridizes with the chimeric mitochondrial RNA molecules (i.e., an ASncmtRNA molecule or a SncmtRNA molecule) to form a stable duplex; (2) hybridizes with the chimeric mitochondrial RNA molecules expressed by tumor cells and inhibits, arrests, kills or abolishes tumor cells; (3) hybridizes with the chimeric mitochondrial RNA molecules expressed by cancer stem cells (CSCs) and inhibits, arrests, kills or abolishes CSCs; (4) suppresses metastasis of a cancer in an individual (e.g., an individual previously treated for cancer with a therapy); (5) treats or prevents relapse of a cancer in an individual (e.g., an individual previously treated for cancer with a therapy); (6) treats metastatic cancer in an individual (e.g., an individual previously treated for cancer with a therapy), and (7) prolongs overall survival in an individual previously treated for cancer with a therapy (e.g., chemotherapy, radiation therapy, surgery or combinations thereof).

In one aspect, the oligonucleotides for use in any of the methods described herein can be complementary to a SncmtRNA molecule and/or to an ASncmtRNA molecule disclosed herein. Without being bound to theory, it is believed that the complementary oligonucleotides bind to the ncmtRNAs and interfere with their cellular functions. As used herein, an oligonucleotide sequence is "complementary" to a portion of an ncmtRNA, as referred to herein, if the oligonucleotide possesses a sequence having sufficient complementarity to be able to hybridize with the ncmtRNA to form a stable duplex. The ability to hybridize will depend on both the degree of complementarity and the length of the oligonucleotide. Generally, the longer the hybridizing oligonucleotide, the more base mismatches with an ncmtRNA it may contain and still form a stable duplex. In some aspects, the one or more oligonucleotide used according to the methods disclosed herein is at least 8 (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more) base pairs in length. Those skilled in the art can ascertain a tolerable degree of mismatch by use of standard procedures to determine the melting point of the hybridized complex. In some embodiments, the one or more oligonucleotide is at least 85% (such as at least 86%, 87%, 88%, 89%, 90%, 91%, 92%, 93%, 94%, 95%, 96%, 97%, 98%, 99%, or 100%) complementary to a SncmtRNA molecule and/or to a ASncmtRNA molecule disclosed herein.

The naturally occurring internucleoside linkage of RNA and DNA is a 3' to 5 phosphodiester linkage. The oligonucleotides (e.g., an antisense oligonucleotide) used for suppressing metastasis of a cancer, treating or preventing relapse of a cancer, or treating metastatic cancer according to any of the methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases present in bodily fluids.

Oligonucleotides (e.g, an antisense oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known in the art.

In one embodiment, oligonucleotides (e.g., an antisense oligonucleotide) targeted to a SncmtRNA molecule and/or to an ASncmtRNA molecule disclosed herein comprise one or more modified internucleoside linkages. In some embodiments, the modified internucleoside linkages are phosphorothioate linkages.

As is known in the art, a nucleoside is a base-sugar combination. The base portion of the nucleoside is normally a heterocyclic base. The two most common classes of such heterocyclic bases are the purines and the pyrimidines Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific, though nonlimiting, examples of oligonucleotides (e.g., an antisense oligonucleotide) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also be employed. Various salts, mixed salts and free acid forms are also included. Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones, alkene containing backbones; sulfamate backbones, methyleneimino and methylenehydrazino backbones; sulfonate and sulfonamide backbones; amide backbones; and others having mixed N, O, S and $CH_2$ component parts.

In other embodiments, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*. 254:1497-1500, 1991.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified oligonucleotides (e.g, antisense oligonucleotides) complementary to SncmtRNA and/or ASncmtRNA used as anticancer therapies in combination with any of the methods disclosed herein (e.g., method of suppressing metastasis of a cancer) may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

The oligonucleotides (e.g, antisense oligonucleotides) for use in the methods disclosed herein (e.g., method of suppressing metastasis of a cancer) can optionally contain one or more nucleotides having modified sugar moieties Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position Modified sugars include, but are not limited to: substituted sugars, especially 2'-substituted sugars having a 2'-F, 2'-OCH2 (2'-OMe) or a 2'-O($CH_2)_2$—$OCH_3$ (2'-O-methoxyethyl or 2'-MOE) substituent group; and bicyclic modified sugars (BNAs), having a 4'-($CH_2$)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In other embodiments, the bicyclic sugar moiety comprises a bridge group between the 2' and the 4'-carbon atoms. In certain such embodiments, the bridge group comprises from 1 to linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—, where each R1 and R2 is, independently, H, hydroxyl, C1-C12 alkyl, substituted C1-C12 alkyl. C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl. C5-C7 alicyclic radical, substituted C5-C7 alicyclic radical halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

Oligonucleotides (e.g, antisense oligonucleotides) for use in any of the methods disclosed herein (e.g., method of suppressing metastasis of a cancer) may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as an ncmtRNA).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2 (3H)-one), phenothiazine cytidine (1H-pyrimido[5,4-b][1,4] benzothiazin-2(3H)-one), O-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4.5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859 Kroschwitz, J. I., ed. John Wiley & Sons, 1990, those disclosed by Englisch et al, *Angewandte Chemie*, International Edition, 1991, 30, 613, and those disclosed by Sanghvi, Y. S., Chapter 15. *Antisense Research and Applications*, pages 289-302. Crooke, S. T. and Lebleu, B. ed., CRC Press, 1993.

Representative United States patents that teach the preparation of certain of the above noted modified nucleobases as well as other modified nucleobases include, but are not limited to, U.S. Pat. Nos. 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, each of which is herein incorporated by reference.

Oligonucleotide Delivery

In one embodiment, a recombinant vector can be used for delivering one or more oligonucleotides (such as any of the oligonucleotides disclosed herein) complementary to a sense and/or antisense chimeric non-coding mitochondrial RNA molecule to the individual. This can include both systemic delivery and delivery localized to a particular region of the body (such as, the bone marrow). Any vector capable of enabling recombinant production of one or more oligonucleotides complementary to a sense or antisense chimeric ncmtRNA molecule and/or which can deliver one or more oligonucleotides complementary to a sense or antisense chimeric ncmtRNA molecule into a host cell is contemplated herein. The vector can be either RNA or DNA, either prokaryotic or eukaryotic, and typically is a virus or a plasmid. The vector can be part of a DNA vaccine or used as part of any other method for delivering a heterologous gene for expression in a host cell that is known to one having skill in the art Recombinant vectors are capable of replicating when transformed into a suitable host cell. Viral vectors infect a wide range of non-dividing human cells and have been used extensively in live vaccines without adverse side effects. A viral vector (such as, but not limited to, an adenoviral vector or an adeno-associated viral (AAV) vector (e.g. AAV-1, AAV-2, AAV-3, AAV-4, AAV-5, AAV-6, etc. or hybrid AAV vectors comprising the same) is an example of a vector for use in the present methods for delivering one or more oligonucleotides complementary to a sense or antisense chimeric ncmtRNA molecule to cancer cells (such as a plasmocyte, see, e.g. U S Patent Application Publication No. 2004/0224389, the disclosure of which is incorporated by reference herein, or a CSC). In some embodiments, a recombinant vector (e.g, a viral vector) described herein can be used in any method described herein. In some embodiments, a method of suppressing metastasis of a cancer in an individual comprises administering to the individual an effective amount of a recombinant vector (e.g., a viral vector) comprising one or more oligonucleotide described herein. In some embodiments, a method for treating or preventing relapse of cancer in an individual comprises administering to the individual an effective amount of a recombinant vector (e.g., a viral vector) comprising one or more oligonucleotide described herein. In some embodiments, a method for treating metastatic cancer in an individual comprises administering to the individual an effective amount of a recombinant vector (e.g., a viral vector) comprising one or more oligonucleotide described herein. In some embodiments, a method for treating a refractory cancer (e.g, a refractory HPV-associated cancer) in an individual comprises administering to the individual an effective amount of a recombinant vector (e.g., a viral vector) comprising one or more oligonucleotide described herein. In some embodiments, the individual has been previously treated for cancer with a therapy (e.g., chemotherapy, radiation therapy, surgery or combinations thereof).

In another aspect, one or more oligonucleotides (such as any of the oligonucleotides disclosed herein) complementary to a sense and/or antisense chimeric non-coding mitochondrial RNA molecule is encapsulated within a microcarrier for deliver to an individual. In certain embodiments, a mixture of different oligonucleotides (such as any of the oligonucleotides disclosed herein) complementary to a sense and/or antisense chimeric non-coding mitochondrial RNA molecule may be encapsulated with a microcarrier, such that the microcarrier encapsulates more than one oligonucleotide species.

Methods of encapsulating oligonucleotides in microcarriers are well known in the art, and described, for example, International application WO98/55495. Colloidal dispersion systems, such as microspheres, beads, macromolecular complexes, nanocapsules and lipid-based system, such as oil-in-water emulsions, micelles, mixed micelles and liposomes can provide effective encapsulation of oligonucleotides within microcarrier compositions. The encapsulation composition may further comprise any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Compositions

Any of the anti-cancer agents (such as oligonucleotide-based agents) disclosed herein can be administered in the form of compositions (e.g, pharmaceutical compositions). These compounds can be administered by systemic administration or local administration through various routes. The route(s) of administration useful in a particular application are apparent to one of skill in the art. Routes of administration include but are not limited to oral, rectal, cerebrospinal, transdermal, subcutaneous, topical, transmucosal, nasopharangeal, pulmonary, intravenous, intramuscular, and intranasal. In some embodiments, the administration is a local administration. In some embodiments, the local administration is selected from the group consisting of administration into an organ, into a cavity, into a tissue, and subcutaneous administration. In some embodiments, the administration is systemic administration. In some embodiments, the systemic administration is intravenous or intraperitoneal administration. These compounds are effective as both injectable and oral compositions. Such compositions are prepared in a manner well known in the pharmaceutical art and comprise at least one active compound. The compositions herein may also contain more than once active compound as necessary for the particular indication being treated, preferably those with complementary activities that do not adversely affect each other. When employed as oral compositions, the oligonucleotides, and other anti-cancer agents disclosed herein, are protected from acid digestion in the stomach by a pharmaceutically acceptable protectant.

This invention also includes pharmaceutical compositions which contain, as the active ingredient, one or more of the anti-cancer agents disclosed herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, in preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents, emulsifying and suspending agents, preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any one of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The anti-cancer agents (such as oligonucleotide-based agents) disclosed herein are effective over a wide dosage range and are generally administered in a therapeutically effective amount. It will be understood, however, that the amount of the anti-cancer agents actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient anticancer therapy is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the anticancer therapies (such as an oligonucleotide) from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Parenteral routes of administration include but are not limited to direct injection into a central venous line, intravenous, intramuscular, intraperitoneal, intradermal, or subcutaneous injection. Oligonucleotide (e.g., an oligonucleotide and microcarrier formulation) formulations suitable for parenteral administration are generally formulated in USP water or water for injection and may further comprise pH buffers, salts bulking agents, preservatives, and other pharmaceutically acceptable excipients. Oligonucleotide(s), for example as oligonucleotide microcarrier complexes or encapsulates, for parenteral injection may be formulated in pharmaceutically acceptable sterile isotonic solutions such as saline and phosphate buffered saline for injection.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

Methods of Treatment

Methods for Suppressing or Preventing Metastasis of a Cancer

In one aspect, provided herein is one or more oligonucleotide (or composition thereof) for use in suppressing or preventing metastasis of a cancer in an individual. In another aspect, provided herein is one or more oligonucleotide (or compositions thereof) for use in combination with at least one therapy for suppressing or preventing metastasis of a cancer in an individual. In any of the aspects, herein, the individual may have been previously treated for cancer with a therapy.

In some aspects, the invention provides a method for suppressing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

In some aspects, the invention provides a method for preventing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing or preventing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxonibicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

As non-limiting examples, a method for suppressing or preventing metastasis of cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

Methods for Treating or Preventing Relapse of a Cancer

In other aspects, provided herein is one or more oligonucleotide (or compositions thereof) for use in treating or preventing relapse of a cancer in an individual. In some embodiments, the individual has responded to initial treatment and is in remission.

In some aspects, the invention provides a method for treating or preventing relapse of cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating or preventing relapse of cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual.

In some embodiments, the oligonucleotide and the at least one therapy is administered simultaneously. For example, one or more oligonucleotide described herein can be administered to an individual during surgical resection of a tumor(s) from the individual.

As non-limiting examples, a method for treating or preventing relapse of a cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stein cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In other embodiments, a "maintenance schedule" may be used in which one or more maintenance oligonucleotide-based (such as antisense-based) therapies are administered less frequency than in the original treatment administered prior to remission, such as once per week or once every two weeks. The maintenance schedule can be continued either for a fixed period of time, generally about 1 or about 2 years, or indefinitely as long as the patient is continuing to show no signs of progressive disease and is tolerating the treatment without significant toxicity.

Methods for Treating Metastatic Cancer

In yet other aspects, provided herein is one or more oligonucleotide (or compositions thereof) for use in treating metastatic cancer (such as relapsed metastatic cancer) in an individual.

In some aspects, the invention provides a method for the treatment of metastatic cancer (such as relapsed metastatic cancer) in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating metastatic cancer (such as relapsed metastatic cancer) in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaneously. For example, one or more oligonucleotide described herein can be administered to an individual during surgical resection of a tumor(s) from the individual.

As non-limiting examples, a method for the treatment of metastatic cancer (such as relapsed metastatic cancer) according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stein cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In another embodiment, the therapeutically effective amount of said one or more oligonucleotide (or compositions thereof) is administered as part of a salvage therapy in treating an individual wherein the cancer has become refractory to other treatment for cancer. In some embodiments, the individual relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine.

Without being bound by theory, it is believed that CSCs give rise to the relapse and/or metastasis of a cancer following treatment of the primary tumor. In some aspects, methods of treatment as described herein (e.g, a method for suppressing or preventing metastasis of a cancer, etc.) eliminates or supresses cancer stem cells. In some embodiments, the oligonucleotides disclosed herein can kill or inhibit cancer stein cells (CSCs) to suppress metastasis, prevent metastasis or prevent relapse of a cancer in an individual. In some embodiments, the individual has been previously treated for cancer with a therapy. In one embodiment, the oligonucleotides disclosed herein can kill or inhibit cancer stem cells (CSCs) that are resistant to treatment (e.g., chemotherapy). In one embodiment, treatment of an individual with any one or more oligonucleotide disclosed herein (e.g., an oligonucleotide complementary to an ASncmtRNA molecule) non-selectively inhibits, arrests, kills, or abolishes the CSCs in the individual. In one embodiment, any one or more oligonucleotide disclosed herein (e.g., an oligonucleotide complementary to an ASncmtRNA molecule) reduces the number of CSCs in the individual as compared to an individual not administered the oligonucleotide. In a further embodiment, the individual has been previously treated for cancer with a therapy.

In any embodiments of the methods herein, any one or more oligonucleotide disclosed herein (e.g., an oligonucleotide complementary to an ASncmtRNA molecule) inhibits tumor growth and/or metastasis in the individual as compared to an individual not administered the oligonucleotide.

In any of the embodiments of the methods herein (e.g., a method for suppressing or preventing metastasis of a cancer, a method for treating or preventing relapse of a cancer, a method for treating metastatic cancer, etc.), the cancer may be a solid cancer or a non-solid cancer. In any of the embodiments herein, the cancer is a solid cancer. Examples of solid cancers contemplated herein include, without limitation, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, brain cancer, cervical cancer, ovarian cancer, liver cancer, sarcoma, bladder cancer, hepatoma, breast cancer, colon cancer, colorectal cancer, endometrial or uterine carcinoma, oralpharyngeal cancer, salivary gland carcinoma, renal cancer, liver cancer, prostate cancer, vulval cancer, thyroid cancer, hepatic carcinoma, gastric cancer, melanoma, and various types of head and neck cancer.

In some embodiments, the cancer is associated with a human papilloma virus (HPV) infection, also referred to herein as "HPV-associated cancer", such as in cervical cancer, oralpharyngeal cancer, and head and neck cancer. For example, one of the most important risk factors for development of cervical cancer is an HPV infection. Over 100 strains of HPV have been identified, however, only a subset are classified as high-risk (16, 18, 31, 33, 35, 39, 45, 51, 52, 56, 58, 59, 68, 73, and 82) or probable high-risk (26, 53, and 66) types for the development of cancer (Munoz et al, NEJM, 348:518-527, 2003). Of these HPV types. HPV16 and HPV18 are reported to cause nearly 70% of all cervical cancer cases while HPV 31 and 35 cause another 10% of cervical cancer cases. See Walboomers et al., J Pathol., 189(1):12-9, 1999. HPV-associated cancer can involve one or more of the following steps: (1) initial HPV infection, (2) persistent HPV infection, (3) transforming HPV infection, in the presence or absence of integration of HPV DNA into the host cell genome, (4) development of precancerous lesions, (5) development of at least one primary tumor, and (6) development of invasive cancer (e.g., metastatic cancer).

In some instances, the HPV-associated cancer is resistant to chemotherapeutic agents regularly used for the treatment of cancer. For example, HPV 16-immortalized cervical cells can develop resistance to cisplatin, paclitaxel, actinomycin D, doxrubicin, etoposide, and 5-fluorouracil which presents a major obstacle in cancer treatment. See Ding et al., Int J Cancer, 15:87(6)818-23, 2000. In some embodiments herein, provided herein is one or more oligonucleotide (or compositions thereof) for use in suppressing metastasis of a cancer in an individual wherein the cancer is resistant to a chemotherapeutic agent, and wherein the cancer is an HPV-associated cancer. In some embodiments herein, provided herein is one or more oligonucleotide (or compositions thereof) for use in treating or preventing relapse of a cancer in an individual, wherein the cancer is resistant to a chemotherapeutic agent, and wherein the cancer is an HPV-associated cancer. In some embodiments herein, provided herein is one or more oligonucleotide (or compositions thereof) for use in treating metastatic cancer (such as relapsed metastatic cancer) in an individual, wherein the metastatic cancer is resistant to a chemotherapeutic agent, and wherein the metastatic cancer is an HPV-associated cancer. In some embodiments herein, provided herein is one or more oligonucleotide (or compositions thereof) for use in treating a refractory cancer in an individual. In some embodiments, the refractory cancer is a refractory HPV-associated cancer. In some embodiments, the refractory HPV-associated cancer is resistant to a chemotherapeutic agent. As used herein, the term "refractory cancer" refers to a cancer (e.g., an HPV-associated cancer) that does not respond to treatment, for example, a cancer that is resistant at the beginning of treatment (e.g., treatment with a chemotherapeutic agent) or a cancer that may become resistant during treatment. In some embodiments, the chemotherapeutic agent is selected from the group consisting of cisplatin, paclitaxel, actinomycin D, doxrubicin, etoposide, and 5-fluorouracil in some embodiments, the chemotherapeutic agent is cisplatin. In some of the embodiments herein, the HPV-associated cancer (e.g., a refractory HPV-associated cancer) is from an infection with one or more HPV strains selected from the group consisting of HPV 16, HPV 18, HPV 31 and HPV 45.

In some embodiments, provided herein is one or more oligonucleotide (or compositions thereof) for use in treating a refractory cancer in an individual. In some embodiments, the refractory cancer is resistant to a chemotherapeutic agent. In some embodiments, the chemotherapeutic agent is cisplatin. In some embodiments, the refractory cancer is a solid cancer disclosed herein. For example, the refractory solid cancer may be one or more of bladder cancer, brain cancer, breast cancer, cervical cancer (e.g., a refractory HPV-associated cervical cancer), colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In some embodiments, the refractory cancer is a non-solid cancer disclosed herein. For example, the refractory cancer may be one or more of multiple myeloma, leukemia, or lymphoma.

In any of the embodiments herein, the cancer is a non-solid cancer. "Non-solid cancer" refers to a hematological malignancy involving abnormal growth and/or metastasis of a blood cell. Examples of non-solid cancers contemplated herein include, without limitation, multiple myeloma, acute myeloid leukemia, acute lymphoblastic leukemia, chronic myelogenous leukemia, chronic lymphocytic leukemia, acute nonlymphocytic leukemia, acute granulocytic leukemia, chronic granulocytic leukemia, acute promyelocytic leukemia, adult T-cell leukemia, a leukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, undifferentiated cell leukemia, idiopathic myelofibrosis, lymphoma (such as Non-Hodgkin's lymphoma, and Hodgkin's lymphoma), and myelodysplastic syndrome.

The methods disclosed herein can be practiced in an adjuvant setting. "Adjuvant setting" can refers to a clinical setting in which an individual has had a history of cancer, and generally (but not necessarily) been responsive to therapy, which includes, but is not limited to, surgery (such as surgical resection), radiotherapy, and chemotherapy. However, because of their history of the cancer (such as melanoma or colon cancer), these individuals are considered at risk of development of cancer Treatment or administration in the "adjuvant setting" refers to a subsequent mode of treatment. The degree of risk (i.e., when an individual in the adjuvant setting is considered as "high risk" or "low risk")

depends upon several factors, most usually the extent of disease (cancer) when first treated.

The present invention is accordingly directed to methods for inhibiting the symptoms or conditions (disabilities, impairments) associated with cancer (e.g, metastatic cancer or relapsed cancer) as described in detail below. As such, it is not required that all effects of the condition be entirely prevented or reversed, although the effects of the presently disclosed methods likely extend to a significant therapeutic benefit for the individual. As such, a therapeutic benefit is not necessarily a complete prevention or cure for the condition, but rather, can encompass a result which includes reducing or preventing the symptoms that result from cancer (e.g, metastatic cancer or relapsed cancer), reducing or preventing the occurrence of such symptoms (either quantitatively or qualitatively), reducing the severity of such symptoms or physiological effects thereof, and/or enhancing the recovery of the individual after experiencing cancer (e.g., metastatic cancer or relapsed cancer) symptoms.

Specifically, the therapies (e.g., one or more oligonucleotide) of the present invention, when administered to an individual, can treat or prevent one or more of the symptoms or conditions associated with cancer (e.g, metastatic cancer or relapsed cancer) and/or reduce or alleviate symptoms of or conditions associated with this disorder. As such, protecting an individual from the effects or symptoms resulting from cancer (e.g, metastatic cancer or relapsed cancer) includes both preventing or reducing the occurrence and/or severity of the effects of the disorder and treating a patient in which the effects of the disorder are already occurring or beginning to occur A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such individual in those who have been treated with the methods of the present invention as compared to those that have not. For example, the at least one clinical or biological score, value, or measure used to evaluate such an individual is the capability of cells (e.g, cancer stem cells) taken from a primary tumor, a secondary tumor, a biopsy, or ascites fluid of an individual to form spheres in a sphere formation assay. Methods for purifying cells such as cancer stem cells from tumors or other biological samples are well known in the art such as in U.S. Pat. No. 8,614,095, the disclosure of which is incorporated by reference herein in its entirety. In an exemplary sphere formation assay, a tumor is surgically removed from a subject and minced with a scalpel into fragments of approximately 2 to 3 mm3 The fragments are washed with a buffer (e.g., PBS) and then incubated with buffer containing sodium hypochlorite. The tumor tissue fragments are washed with buffer and digested with PBS and digested with a medium containing one or more of collagenase 1, collagenase IV, dispase, hyaluronidase and DNAase. The cell suspension is centrifuged and the pellet is suspended in buffer containing βFGF and EGF. The cells are washed to remove serum and suspended in medium supplemented with human EGF, human βFGF, B27 supplement without vitamin A, hydrocortisone, insulin, and N2 supplement. The cells are subsequently cultured in non-adherent plates After 10 days in culture, spheres of 100 to 200 μm in diameter are obtained and counted. The spheres can be further expanded clonally, or injected into a subject to observe the capability of tumor formation. In some embodiments, an individual that has received an effective amount of one or more oligonucleotide (or compositions thereof) disclosed herein, alone or in combination with at least one therapy disclosed herein, has reduced sphere formation as compared to an individual not treated with the oligonucleotides of the present invention.

Treating Viral Infections

SLC7A11 is implicated as a fusion entry receptor utilized by herpesvirus.

Kaposi's sarcoma-associated herpesvirus (KSHV, human herpesvirus 8) is the causative agent of Kaposi's sarcoma and other lymphoproliferative syndromes often associated with HIV/AIDS. Functional complementary DNA selected for a receptor mediating KSHV cell fusion identified SLC7A11. Expression of recombinant SLC7A11 rendered otherwise unsusceptible target cells permissive to both KSHV cell fusion and virion entry. Antibodies against SLC7A11 blocked KSHV fusion and entry with naturally permissive target cells. KSHV target cell permissiveness correlated closely with endogenous expression of SLC7A11 mRNA and protein in diverse human and nonhuman cell types. See Kaleeba et al. (2006). *Science,* 311(5769):1921-1924.

The methods of protecting against herpesvirus infection are largely the same as those described throughout the present disclosure in treating/mitigating/preventing cancer. The difference being that the molecular biology methods applied to modulating the expression of SLC7A11 mRNA and SLC7A11 protein in cancer cells are applied to the cells typically permissive of herpesvirus infection, such as cells permissive of KSHV infection. The inventors specifically contemplate the methods described herein, as applied to cancer cells, to be further applied to cells permissive of herpesvirus infection, human herpesvirus 8 infection, and KSHV infection.

In some aspects, the location of the herpesvirus is in blood vessels or lymph nodes. In some aspects, the location of the herpesvirus is in the skin, particularly on or near the genitals and/or mouth. In some aspects, the location of the herpesvirus is in the mouth, buccal cavity. In some aspects, the herpesvirus, particularly KSHV, results in the formation of Kaposi's sarcoma. The Kaposi's sarcoma presents as a lesions that may be visible on the skin, particularly the legs, feet, or face. In some aspects, lesions may appear in the genital area, mouth, or lymph nodes.

In some aspects, the interfering RNAs, which include antisense RNA, RNAi, siRNA, and miRNA are administered directly to one or more lymph nodes in the form of an injection. In some aspects, the interfering RNAs are administered systemically via intravenous injection. In some aspects, the interfering RNAs are administered to the mouth in an oral administration. In some aspects, the interfering RNAs are administered to the surface of the skin or administered via injection beneath the epidermis.

In some aspects, the interfering RNAs are administered only once. In some aspects, one or more subsequence administrations of the interfering RNAs occur. In some aspects, the one or more subsequence administrations comprising 1, 2, 3, 4, 5, 6, 7, 8, 9, 10, 11, 12, 13, 14, 15, 16, 17, 18, 19 or 20 administrations of the interfering RNAs after an initial administration.

In some aspects, administration of the interfering RNAs yield a decrease in the incidence of herpesvirus infection. In some aspects, administration of the interfering RNAs yield a decrease in the incidence of human herpesvirus 8 infection. In some aspects, administration of the interfering RNAs yield a decrease in the incidence of KSHV infection. In some aspects, administration of the interfering RNAs prevent formation of Kaposi's sarcoma. In some aspects, administration of the interfering RNAs decrease formation of Kaposi's sarcoma. In some aspects, administration of the interfering RNAs to HIV+ subjects or HIV+ subjects exhibiting signs of AIDS yields a prevention of the formation of Kaposi's sarcoma or a decrease in the formation of Kaposi's sarcoma.

Protecting Against Tuberculosis

SLC7A11 is Implicated in Tuberculosis.

Physiological functions of macrophages play a central role in the pathogenesis of tuberculosis, and these physiological functions depend on redox state. The SLC7A11 cystine-glutamate transporter influences may ROS-dependent pathways by regulating the production of the antioxidant glutathione. SLC7A11 is able to alter this critical host redox balance by increasing the glutathione synthesis aspect of phagocyte physiology, suggesting a link in tuberculosis pathogenesis. SLC7A11 expression was found to be increased in peripheral blood monocytes in active tuberculosis. SLC7A11 expression in macrophages was induced by *Mycobacterium tuberculosis* through TLR2/Akt- and p38-dependent signaling pathway. Importantly, SLC7A11 deficiency conferred protection against tuberculosis, as SLC7A11 knockout mice displayed increased *M. tuberculosis* load and reduced pulmonary pathology in the lungs compared to wild type mice. SLC7A11 disruption enhanced the mycobacteriacidal activity of macrophages through increasing the mycothiol oxidation. Importantly, chemical inhibition of SLC7A11 with sulfasalazine, a specific SLC7A11 inhibitor already approved by the FDA for treatment of inflammatory bowel disease, produces similar protective effects in vivo and in vitro, indicating that SLC7A11 may be a novel and useful target for host-directed tuberculosis treatment strategy. See Cai et al. (2016). Oncotarget, 7(21):31001-31013.

The methods of protecting against tuberculosis are largely the same as those described throughout the present disclosure in treating/mitigating/preventing cancer. The difference being that the molecular biology methods applied to modulating the expression of SLC7A11 mRNA and SLC7A11 protein in cancer cells are applied to the cells of the respiratory tract, particularly those of the lungs. The inventors specifically contemplate the methods described herein, as applied to cancer cells, to be further applied to cells of the respiratory tract.

In some aspects, the interfering RNAs, which include antisense RNA, RNAi, siRNA, and miRNA are administered directly to the respiratory tract in the form of an inhalant. In some aspects, the interfering RNAs are administered systemically via intravenous injection. In some aspects, the interfering RNAs are administered to a location in the lungs via injection into one or both of the lungs.

In some aspects, the interfering RNAs are administered only once. In some aspects, one or more subsequence administrations of the interfering RNAs occur. In some aspects, the one or more subsequence administrations comprising 1, 2, 3, 4, 5, 6, 7, 8, 9, 10, 11, 12, 13, 14, 15, 16, 17, 18, 19 or 20 administrations of the interfering RNAs after an initial administration.

In some aspects, administration of the interfering RNAs are used to treat a tuberculosis infection caused by any member of the genus *Mycobacterium*. In some aspects, administration of the interfering RNAs are used to treat a tuberculosis infection caused by *Mycobacterium tuberculosis*. In some aspects, administration of the interfering RNAs are used to treat a tuberculosis infection caused by multi-drug resistant *Mycobacterium tuberculosis*.

In some aspects, administration of the interfering RNAs are used to prevent a tuberculosis infection caused by any member of the genus *Mycobacterium*. In some aspects, administration of the interfering RNAs are used to prevent a tuberculosis infection caused by *Mycobacterium tuberculosis*. In some aspects, administration of the interfering RNAs are used to prevent a tuberculosis infection caused by multi-drug resistant *Mycobacterium tuberculosis*. In some aspects, the prevention of tuberculosis is desired in those that spend time around others that have been infected with a bacterium of genus of *Mycobacterium* that causes tuberculosis, or infected with *M. tuberculosis* or multi-drug resistant *M. tuberculosis*. In some aspects, administration of the interfering RNAs are used to prevent the development of tuberculosis in a subject that has been infected with a bacterium of genus of *Mycobacterium* that causes tuberculosis, or infected with *M. tuberculosis* or multi-drug resistant *M. tuberculosis*.

Protecting Against Liver Fibrosis

SLC7A11 is implicated liver fibrosis.

Liver fibrosis develops in the context of excessive oxidative stress, cell death, and accumulation of myofibroblasts (MFs) derived from hepatic stellate cells (HSCs). Ferroptosis is a type of regulated cell death that can be caused by inhibiting SLC7A11 cystine/glutamate antiporter. While SLC7A11 is inducted in various liver diseases, its role in HSC activation and liver fibrosis was only recently discovered. SLC7A11 appears to be required for HSCs to antagonize ferroptosis and remain myfibroblastic. See Du et al. (2019) *BioRxiv*, doi: 10.1101/2019.12.23.886259.

Compared to healthy hepatocytes, MF-HSCs are exquisitely sensitive to ferroptosis induced by inhibiting SLC7A11. In acutely injured livers, systemic inhibitors of SLC7A11 can inhibit fibrosis without worsening liver injury. Thus, mitigating the expression of SLC7A11 is expected to protect against liver fibrosis.

The methods of protecting against liver fibrosis are largely the same as those described throughout the present disclosure in treating/mitigating/preventing cancer. The difference being that the molecular biology methods applied to modulating the expression of SLC7A11 mRNA and SLC7A11 protein in cancer cells are applied to the cells of the liver. The inventors specifically contemplate the methods described herein, as applied to cancer cells, to be further applied to cells of the liver.

In some aspects, the location of the liver fibrosis is in the right lobe of the liver. In some aspects, the location of the liver fibrosis is in the left lobe of the liver. In some aspects, the location of the liver fibrosis is in the caudate lobe of the liver.

In some aspects, the interfering RNAs, which include antisense RNA, RNAi, siRNA, and miRNA are administered directly to the liver in the form of an injection in one or more of the right lobe, left lobe, or caudate lobe. In some aspects, the interfering RNAs are administered systemically via intravenous injection. In some aspects, the interfering RNAs are administered to a location in the liver via injection into one or more sites that exhibit a more dense occurrence of MF-HSCs as compared to other sections/lobes of the liver.

In some aspects, the interfering RNAs are administered only once. In some aspects, one or more subsequence administrations of the interfering RNAs occur. In some aspects, the one or more subsequence administrations comprising 1, 2, 3, 4, 5, 6, 7, 8, 9, 10, 11, 12, 13, 14, 15, 16, 17, 18, 19 or 20 administrations of the interfering RNAs after an initial administration.

In some aspects, administration of the interfering RNAs yield a decrease in formation of liver fibrosis, as compared to a similarly situated subject not having been administered the interfering RNAs.

Aiding Recovery in Spinal Cord Injury (SCI)

SLC7A11 is implicated in the recovery from SCI in mammals.

In situ hybridization allowed for the detection of SLC7A11 mRNA in astrocyte subpopulations and in meningeal fibroblasts in the normal spinal cord. During the early phase of spinal cord injury, SLCA11 mRNA could also be detected in microglial cells and overall mRNA levels were upregulated, peaking at 4 days post-injury. While both injured SLC7A11+/+ and SLC7A11 −/− mice partly recovered their motor functions, the SLC7A11 −/− mice progressed further by recovering muscular grip strength as well as pre-SCI weight substantially faster than SLC7A11 −/− mice. Histology of injured spinal cords revealed increased number of motor neurons in SLC7A11 −/− mice at multiple distances around lesion epicenter. As SLC7A11 has been demonstrated as a regulator of microglial function, markers of microglial activation were studied. At 2 weeks post-SCI, the number of type A Iba1+ cells was unexpectedly much higher in contused SLC7A11 −/− than in SLC7A11+/+ spinal cords. Analysis of M1/M2 polarization sowed that contused SLC7A11 −/− spinal cords contained higher mRNA levels of Ym1 and IGf-1 (M2) while lower levels of NOX2 and TNF-α (M1). Additionally, the number of astrocytes and oligodendrocytes were unchanged between the two injured groups. Thus, following SCI trauma, an early SLC7A11 upregulation appears to exacerbate microglia-driven inflammation and influences motor neuron survival. See Sprimont et al. (2018) *Front. Neurosci. Conference Abstract: Belgian Brain Congress* 2018—*Belgian Brain Council*. Doi:10.3389/conf.fnins.2018.95.00035.

The methods of aiding in recovery of spinal cord injury are largely the same as those described throughout the present disclosure in treating/mitigating/preventing cancer. The difference being that the molecular biology methods applied to modulating the expression of SLC7A11 mRNA and SLC7A11 protein in cancer cells are applied to the cells of the spinal cord and/or the surrounding cells or tissues. The inventors specifically contemplate the methods described herein, as applied to cancer cells, to be further applied to cells of the spinal cord, corresponding neurological cells, and cells surrounding the SCI.

In some aspects, the location of the SCI is in the cervical spinal cord. In some aspects, the cervical spinal cord spans regions C1 to C8. In some aspects, the location of the SCI is in the thoracic spinal cord. In some aspects, the thoracic spinal cord spans regions T1 to T12. In some aspects, the location of the SCI is in the lumbar spinal cord. In some aspects, the lumbar spinal cord spans regions L1 to L5. In some aspects, the location of the SCI is in the sacral spinal cord. In some aspects, the sacral spinal cord spans regions S1 to S5.

In some aspects, the SCI is a complete SCI, meaning that a total lack of sensory and motor function below the injury site. In some aspects, the SCI is an incomplete SCI, meaning that the ability of the spinal cord to convey messages to or from the brain to beyond the SCI is not completely lost.

In some aspects, the SCI is the result of a bruise or contusion. In some aspects, the SCI is the result of a stretch. In some aspects, the SCI is the result of a crush. In some aspects, the SCI is the result of a complete or partial severing. In some aspects, the SCI type is central cord syndrome, anterior cord syndrome, or Brown-Sequard syndrome. In some aspects, the SCI occurs in the cauda equine or the conus medularis.

In some aspects, the interfering RNAs, which include antisense RNA, RNAi, siRNA, and miRNA are administered to the site of the SCI. In some aspects, the interfering RNAs are administered to the spinal cord. In some aspects, the interfering RNAs are administered to the spinal cord tissues, comprising one or more of the following cell types: sensory neurons, motor neurons, interneurons, neuroglia, ependymal cells, oligodentrocytes, astrocytes, microglia, satellite cells, and schwann cells.

In some aspects, the administration is an injection of a composition comprising the interfering RNAs into the cerebrospinal fluid that surrounds the spinal cord. In some aspects, the administration is an injection of a composition comprising the interfering RNAs into the cerebrospinal fluid at the region of the SCI. In some aspects, the administration is an injection of a composition comprising the interfering RNAs into the one or more of the layers of the meninges. In some aspects, the administration is an injection of a composition comprising the interfering RNAs beneath the dura, arachnoid, or the pia mater of the meninges.

In some aspects, the interfering RNAs are administered within 1 day of the SCI. In some aspects, the interfering RNAs are administered within 2, 3, 4, 5, 6, 7, 8, 9, 10, 11, 12, 13, 14, 15, 16, 17, 18 19, 20, 21, 22, 23, 24, 25, 26, 27, 28, 29, or 30 days of the SCI. In some aspects, one or more subsequence administrations of the interfering RNAs occur. In some aspects, the one or more subsequence administrations comprising 1, 2, 3, 4, 5, 6, 7, 8, 9, 10, 11, 12, 13, 14, 15, 16, 17, 18, 19 or 20 administrations of the interfering RNAs after an initial administration. In some aspects, the interfering RNAs are administered only once.

In some aspects, administration of the interfering RNAs yield a decrease in the recovery time by at least 1 week, as compared to a similarly injured subject not having been administered the interfering RNAs. In some aspects, administration of the interfering RNAs yield a decrease in the recovery time by at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24 weeks, as compared to a similarly injured subject not having been administered the interfering RNAs.

Articles of Manufacture or Kits

In another aspect, an article of manufacture or kit is provided which comprises one or more oligonucleotide described herein. The article of manufacture or kit may further comprise instructions for use of the one or more oligonucleotide in the methods of the invention. Accordingly, in certain embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for suppressing metastasis of a cancer, preventing or treating relapse of a cancer, and/or treating metastatic cancer in an individual comprising administering to the individual an effective amount of the one or more oligonucleotide. In certain embodiments, the individual has been previously treated for cancer with a therapy (e.g., chemotherapy, radiation therapy, surgery, or combinations thereof). In some embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for treating a refractory cancer (e.g., a refractory HPV-associated cancer) in an individual comprising administering to the individual an effective amount of the one or more oligonucleotide.

The article of manufacture or kit may further comprise a container. Suitable containers include, for example, bottles, vials (e.g., dual chamber vials), syringes (e.g., single or dual chamber syringes), IV bags, and test tubes. The container may be formed from a variety of materials such as glass or plastic. The container holds the composition (e.g., pharmaceutical formulation).

The article of manufacture or kit may further comprise a label or package insert, which is on, or associated with the container and may indicate directions for reconstitution and/or use of the composition (e.g., pharmaceutical formulation). The label may further indicate that the formulation is useful or intended for intravenous, subcutaneous, or other modes of administration for suppressing metastasis of a cancer, preventing or treating relapse of a cancer, and/or treating metastatic cancer in an individual. In other embodiments, the label may further indicate that the formulation is useful or intended for intravenous, subcutaneous, or other modes of administration for treating a refactory cancer (e.g., a refractory HPV-associated cancer) in an individual. The container holding the formulation may be a single-use vial or a multi-use vial which allows for repeat administrations (e.g., from 2-6 administrations) of the reconstituted composition (e.g., pharmaceutical formulation). The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture of kit described herein optionally further comprises a container comprising a second therapeutic composition (e.g., an anti-cancer agent). For example, the article of manufacture or kit can comprise one or more oligonucleotide as a first composition (e.g., a first pharmaceutical composition) and an anti-cancer agent as a second composition (e.g., a second pharmaceutical composition). In some embodiments, the kit further comprises instructions for use of the one or more oligonucleotide in combination with the anti-cancer agent in the methods of the invention. An exemplary anti-cancer agents may be remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine. IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and/or etoposide.

Host Cells

Yet further provided is an isolated cell or population of cells, comprising, or alternatively consisting essentially of, or yet further consisting of, isolated polynucleotides, viral particles, vectors and packaging systems as described above and incorporated herein by reference. In one aspect, the isolated cell is a packaging cell line.

Also provided is an isolated cell or population of cells, comprising, or alternatively consisting essentially of, or yet further consisting of, a polynucleotide sequence as described herein.

The isolated cells described herein can be any of a cell of a species of the group of: murine, rats, rabbit, simians, bovines, ovine, porcine, canines, feline, farm animals, sport animals, pets, equine, and primate, and in particular a human cell.

The vectors and cells can be contained within a composition that contains the vector and/or host cell and a carrier, e.g., a pharmaceutically acceptable carrier. They can be formulated for various modes of administration and contain an effective amount of the vector and/or host cell that is effective for the patient, the disorder or disease, the vector and mode of administration. In one aspect, the mode of administration is systemic or intravenous. In another aspect, administration is local by direct injection.

EXAMPLES

These examples are provided for illustrative purposes only and not to limit the scope of the claims provided herein.

Example 1—Genome-Wide Search for Factors that Limit OXPHOS Identifies Components of the Pre-mRNA Splicing Machinery To nominate genes whose depletion promotes OXPHOS, we reanalyzed the results of our CRISPR death screen comparing viability in glucose and galactose (Arroyo et al., 2016). This screen quantified viability of CRISPR/Cas9 mutagenized K562 cells grown in glucose that are then shifted to glucose or galactose conditions for 24 hours. Loss of genes required for OXPHOS is tolerated in the presence of glucose, whereas these genes are conditionally essential when the sole sugar glucose is replaced by galactose, as it is a poor substrate for glycolysis (Robinson et al., 1992). We re-analyzed 9,189 expressed non-essential genes in K562 cells, calculating a z-score of viability of the gene knockout under each conditions (FIG. 1B, Table S1) (To et al., 2019). In this analysis, sgRNAs targeting 3,726 non-expressed genes were used as negative controls. Gene Ontology (GO) analysis confirmed the loss of viability conferred by the depletion of genes encoding subunits of the mitochondrial respiratory chain, as expected (FIG. S1A).

Conversely, analysis of the genes whose depletion promotes relative viability in galactose identified splicing-related GO terms including "spliceosomal complex" ($P<10^{-5}$) or "U1 snRNP" ($P<10^{-4}$) (FIG. 1C, SIB). Hits underlying these GO terms included 3 of the 4 U1 snRNP-specific factors (LUC7L2, SNRPA, SNRNP70), heterogeneous nuclear ribonucleoproteins (HNRNPD, HNRNPU), splicing factors (SF3B2, SFPQ), RNA helicases (DHX8, DDX47), an LSm-family protein (LSM1), an exon junction complex protein (ACIN1), and a polyadenylate-binding protein (PABPC1).

We used CRISPR/Cas9 and sgRNA sequences from the screening library to disrupt the expression of six representative genes identified in the screen that were not previously linked to energy metabolism and included LUC7L2, SNRPA (U1A), SNRNP70 (U1-70K), ACIN1, HNRNPD and PABPC1. A gene encoding a subunit of respiratory complex I (NDUFB5) was included as a control with known impact on metabolism. K562 cells were transduced with the two most effective sgRNAs followed by measurement of the oxygen consumption rate (OCR), a proxy for OXPHOS, and the extracellular acidification rate (ECAR), a proxy for glycolysis. Notably, depletion of several of these genes significantly increased basal, maximal and ATP-linked OCR (FIG. 1D, S1C-D), while also decreasing ECAR (FIG. 1E), suggesting rewiring of metabolism from glycolysis to OXPHOS. In fact, the OCR/ECAR ratio was significantly increased upon depletion of all six selected genes (FIG. 1F), whereas it decreased in NDUFB5-depleted cells, as expected. Together, these results confirm the impact of silencing pre-mRNA splicing genes on energy metabolism.

Example 2—Expression of LUC7L2 Represses OXPHOS

Among the validated screening hits, LUC7L2 showed the most robust phenotype. This relatively unstudied gene belongs to the LUC7 family together with LUC7L and LUC7L3, which are all homologs of yeast LUC7, a U1 snRNP protein involved in pre-mRNA splicing (Singh et al., 2013, Fortes et al., 1999). Mutations, haploinsufficiency or complete loss of LUC7L2 are associated with poorer survival in myelodysplastic syndrome (MDS) (Singh et al., 2013), and none of the LUC7 family members in yeast or human have been previously linked to energy metabolism.

To further investigate the function of LUC7L2, we used CRISPR/Cas9 to generate single cell clones in which the expression of LUC7L2 was ablated in K562, HeLa and HAP1 cells (hereafter LUC7L2$^{KO}$) (FIG. S2A-C). Focusing on the K562 cell lines from our screen, we observed that LUC7L2$^{KO}$ cells grew more slowly relative to wild-type in standard 25 mM glucose cell culture conditions (FIG. 2A). However, they grew relatively faster when glycolysis was limited, either pharmacologically by treatment with 2-deoxyglucose (2-DG) or when glucose was replaced by galactose (FIG. 2B). In contrast, LUC7L2 depletion sensitized cells to pharmacologic inhibition of OXPHOS (FIG. 2C).

Next, we characterized the bioenergetic effects of LUC7L2 depletion. OCR measurement confirmed our initial observation that LUC7L2 represses OXPHOS and accordingly all measured respiratory parameters in LUC7L2$^{KO}$ K562 and HAP1 cells were increased relative to controls (FIG. 2D, S2D-F). As expected from our initial validation, LUC7L2-depleted K562 clones exhibited less ECAR (FIG. 2E). To test whether the global abundance of mitochondria was affected by LUC7L2 depletion, we quantified mitochondrial DNA copy number and citrate synthase activity and observed no differences (FIG. 2F-G). Electron microscopy also confirmed the absence of gross differences in mitochondrial abundance or ultrastructure in these cells (FIG. S2G). Collectively, our results indicate that LUC7L2 impacts metabolic state-dependent cell growth and bioenergetics. While LUC7L2 does not appear to affect the gross abundance of mitochondria, it influences the balance between glycolysis and OXPHOS activities.

Example 3—Expression of LUC7L2 Represses OXPHOS

The rewiring of cellular bioenergetics upon LUC7L2 depletion prompted us to analyze the abundance of the metabolic intermediates central to glycolysis and respiration. We used liquid chromatography mass spectrometry to quantify the relative steady-state levels of 123 metabolites in cell pellets and the absolute consumption/release rates of 22 media metabolites (Table S2-3). Consistent with our ECAR results, we observed reduced rates of glucose uptake, lactate secretion, and media acidification, as well as a dramatically reduced media lactate/pyruvate ratio in LUC7L2$^{KO}$ K562 cells, all consistent with decreased glycolysis (FIG. 3A-C, S3C, S3F). In LUC7L2$^{KO}$, we observed significant accumulation of glucose, glucose-6-phosphate and of the fructose-6-phosphate/glucose-1-phosphate isomers. Importantly, levels of fructose-1,6-bisphosphate, the fourth intermediate of glycolysis and the product of phosphofructokinase (PFK), were significantly reduced in the absence of LUC7L2. Thus, we observed accumulation of the substrate of PFK and depletion of its product, identifying this enzyme as a metabolic crossover point in LUC7L2$^{KO}$ cells. Of note, similar to PFKM-related pathologies (Tarui et al., 1965), we also found significant accumulation of glycogen and its precursor UDP-glucose in these cells (FIG. 3A).

Our metabolite analysis also provides insight into how OXPHOS is re-wired with LUC7L2$^{KO}$. We observed accumulation of four of the five TCA metabolites analyzed (2-ketoglutarate, succinate, fumarate and malate). The TCA-derived oncometabolite 2-hydroxyglutarate also accumulated, as well as aspartate, which can be made from the TCA cycle (FIG. 3A, S3A). Glutamine is an important fuel that can contribute glutamate to the TCA cycle (Reitzer et al., 1979), but glutamine consumption and intracellular glutamine levels remained unchanged (FIG. 3A-B). In contrast, intracellular glutamate accumulated in LUC7L2$^{KO}$. Intracellular glutamate mostly originates from glutamine deamination and may either converted into 2-ketoglutarate to serve as an anaplerotic input into the TCA cycle or be exported out of the cell in exchange for cystine via the system $X_c^-$. This plasma membrane antiporter is encoded by two subunits, SLC7A11 (xCT) and SLC3A2 (4F2) (Sato et al., 1999). The system $X_c^-$ has already been implicated in the survival of cells in low glucose conditions (Shin et al., 2017, Koppula et al., 2017). Importantly, we found that while intracellular glutamate accumulated in LUC7L2-depleted cells, its secretion to the culture media was significantly reduced (FIG. 3B). These observations pointed to the existence of a second crossover point at the level of the system $X_c^-$, as LUC7L2-depleted cells consumed less media cystine (FIG. 3B, S3E).

Collectively, analysis of steady state intracellular metabolites as well as consumption and release of media metabolites indicate that the loss of LUC7L2 is associated with to two key crossover points in energy metabolism: (1) upper glycolysis at PFK, and (2) glutamate oxidation via the exchange of cystine and glutamate at the transporter system $X_c^-$. Both of these metabolic changes are consistent with the observed shift from glycolysis to OXPHOS activities in cells lacking LUC7L2.

Example 4—LUC7L2 is a U1 snRNP Subunit Involved in Pre-mRNA Splicing

LUC7L2 is a poorly studied gene, but evidence based on homology with yeast LUC7 (Fortes et al., 1999) and proteomics of human spliceosome complexes (Makarov et al., 2012) suggests that it part of the U1 snRNP. However, a specific association with U1 has not been validated. We investigated the subcellular localization of LUC7L2 as well as its interaction partners. Microscopy showed that LUC7L2 is nuclear-localized and enriched in SRSF2-positive nuclear speckles, which are enriched for the pre-mRNA splicing machinery (Rino et al., 2007) (FIG. 4A). Immunoprecipitation coupled to mass spectrometry revealed 29 LUC7L2-interacting proteins, including our validated screening hits SNRPA and SNRNP70 along with most known U1 subunits (FIG. 4B-C, Table S4). We next identified the transcripts that are bound by endogenous LUC7L2 using enhanced crosslinking and immunoprecipitation coupled to RNA deep-sequencing (eCLIP) (Van Nostrand et al., 2016). In agreement with the proposed role for LUC7L2 as a U1 snRNP subunit, we found that LUC7L2 binds to the U1 snRNA, and to a lesser extent to the U6 snRNA, which comes in close proximity to U1 during the transfer of the 5' splice site (5'SS) during splicing (Plaschka et al., 2018) (FIG. 4D). Analysis of eCLIP peaks identified binding of LUC7L2 in 5,595 and 3,378 transcripts from HeLa and K562 cells, respectively. Of these, 2,614 were common to both cell types (overlap significance $P<10^{-3}$, Poisson) (FIG. 4E). Within pre-mRNAs, we found that LUC7L2 preferentially bound exons and introns, and to a lesser extent untranslated regions (UTRs) (FIG. 4F). A meta-analysis revealed that LUC7L2 preferentially bound near splice sites (FIG. 4G). The pattern binding near splice sites is consistent with association of LUC7L2 with U1 snRNP complexes, which recognize 5'SS and also interact with U2 snRNP bound upstream of 3' splice sites (De Conti et al., 2013)

To understand the impact of LUC7L2$^{KO}$ on gene expression, we profiled transcriptomes of LUC7L2$^{KO}$ HeLa and K562 cells. Loss of LUC7L2 changed the expression of ~1000-1500 genes in each cell type (FDR<10' and >|50%| fold change), 149 of which were shared (overlap not significant) (FIG. 4H, S4, Table S6). Splicing analysis using rMATS (Shen et al., 2014), identified 3,415 and 3,397 alternative splicing events in HeLa and K562 cells, respectively, (FDR<0.1 and |Δψ|>0.05, where ψ represents "percent spliced in" and Δψ is the change in ψ following gene depletion) (FIG. 4I, Table S7). ~20-25% of the alternative splicing events had a LUC7L2 binding site within a distance of 250 nucleotides (FIG. 4J), and alternative exon skipping (SE) was particularly represented in LUC7L2$^{KO}$ (FIG. 4K). In all, 379 splicing changes were shared between both cell types (overlap significance $P<10^{-3}$, Poisson) (FIG. 4I). Among the alternatively spliced events containing LUC7L2 binding sites in close proximity, and as described below, two genes caught our attention: LUC7L, a close paralog of LUC7L2, and PFKM, a glycolytic enzyme whose natural mutations cause aberrant glycogen accumulation (Tarui et al., 1965), and whose inhibition with tryptonilamide was recently shown to cause a glycolysis to OXPHOS shift, both consistent with the phenotype of LUC7L2$^{KO}$ cells.

Example 5—Cross-Regulation and Partial Redundancy within the LUC7 Family

LUC7L and LUC7L2 encode two highly similar proteins with two ZnF-type RNA-binding domains and a C-terminal SR-rich domain (FIG. S5A) (Tufarelli et al., 2001). We investigated the altered splicing of LUC7L in LUC7L2$^{KO}$ and found decreased retention of an annotated exon embedded in an intron between canonical exons 1 and 2 of LUC7L, a region highly bound by LUC7L2 (4=−0.30 and −0.17, respectively) (FIG. 5A, S5B). Importantly, retention of either the exon or the intron results in multiple premature termination codons (PTC) in LUC7L, which likely leads to transcript degradation by nonsense-mediated mRNA decay (NMD). Accordingly, transcript and protein analysis revealed a strong up-regulation of LUC7L in LUC7L2-depleted cells, indicating a repressive role for LUC7L2 (FIG. 5B, S5C).

Negative cross-regulation of paralogous splicing proteins is common and may play a homeostatic role (Spellman et al., 2007). We next looked at the abundance of Luc7 proteins a mouse proteomics atlas (Geiger et al., 2013) (FIG. S5D). Supporting the role played by LUC7L2 in OXPHOS repression, we observed that the expression of the mouse Luc7 proteins was the highest in glycolytic tissues such as the thymus, while it was the lowest in high OXPHOS tissues. However, the expression pattern of individual members of the family was not identical. For example, Luc7l was present at higher levels in the brain, while expression of Luc7l3 was not detectable in the spleen. Thus, while it is likely that all three members of the LUC7 family may be redundant, as expected from sequence conservation, differences in their expression patterns suggests they may also impact aspects of pre-mRNA splicing and energy metabolism in a tissue-specific manner.

To experimentally address the function of each LUC7 genes, we next depleted each individually, as well as LUC7L and LUC7L2 together (FIG. 5B). We found that while LUC7L and LUC7L2-depletion led to a mild defect in cell proliferation (FIG. 5C), depletion of LUC7L3 caused a strong growth defect, while LUC7L and LUC7L2 were synthetic lethal. To directly address redundancy, we investigated whether members of the LUC7 family could rescue the metabolic phenotype observed in LUC7L2$^{KO}$ cells. For this purpose, we stably expressed the cDNA of LUC7L, LUC7L2 and LUC7L3 in these cells and measured oxygen consumption. Importantly, we found that expression of LUC7L2 alone was able to decrease OCR in wild-type cells (FIG. 5D), strongly supporting that LUC7L2 is a limiting factor for the glycolysis/OXPHOS balance. Furthermore, re-expression of any of the members of the family could restore normal oxygen consumption in LUC7L2$^{KO}$ cells, although to varying degrees (FIG. 5D).

Example 6—LUC7L2 Promotes Expression of PFKM and Suppresses Glycogenesis

Next, we investigated changes in the splicing of glycolytic enzymes following LUC7L2 depletion. Most transcripts encoding glycolytic machinery were bound by LUC7L2 and we found alternative splicing in PKM, ALDOA, ENO3 and PKFM (phosphofructokinase M), which was the most altered in both LUC7L2' HeLa and K562 cells (Table S5-6). This kinase resides at the intersection of glycolysis and glycogenesis, and our unbiased metabolomics experiment suggested decreased PFKM activity (FIG. 3A). Two altered splicing events in PFKM were detected: increased usage of an alternative 5'SS between exon 11 and 12 (Δψ=0.29, FDR<10$^{-11}$), and decreased inclusion of exon 12 (Δψ=−0.19, FDR<10$^{-12}$) (FIG. 5E). Notably, both events were expected to disable PFKM activity: first, the alternative 5'SS whose usage increases upon LUC7L2-depletion results in a PTC (FIG. 5E). Second, skipping of exon 12 deletes 30 amino acids in the F1P binding site of the enzyme (FIG. S5E), which contains a well-characterized residue (D309) whose mutation in Tarui disease leads to complete inactivation of the enzyme and aberrant glycogen accumulation (FIG. S5E) (Vives-Corrons et al., 2013). Both altered spliced sites were bound by LUC7L2, suggesting direct regulation (FIG. 5E). To directly test the role of LUC7L2 and the U1 snRNP in splicing PFKM transcripts, we designed an antisense oligonucleotide (ASO) targeting the 5'SS of exon 12, where they bind. We found that both chronic LUC7L2 depletion and acute ASO treatment led to similar skipping of exon 12 and decreased PFKM protein abundance, indicating that skipping of PFKM exon 12 likely destabilizes the protein (FIG. 5G, H). This observation was consistent with the reduced PFK activity initially observed in LUC7L2' cells and the redirection of glucose to glycogen storage (FIG. 3A). To experimentally address the role of PKFM in mediating the phenotype of LUC7L2-depletion, we next re-introduced its cDNA in LUC7L2' cells (FIG. S5F). We observed that whereas expression of PFKM was not sufficient to restore the bulk of glycolysis in a LUC7L2$^{KO}$ background, likely due to the existence of additional splicing events in glycolytic enzymes, it was sufficient to restore normal glycogen storage (FIG. 5I-J). Together, our data indicate that LUC7L2 is required for PFKM pre-mRNA splicing, and that its absence favors glycogenesis.

Example 7—LUC7L2-Depletion Causes Secondary Accumulation of Respiratory Chain Complexes We next performed global quantitative proteomics to obtain a comprehensive view of the proteome remodeling in LUC7L2-depleted cells (FIG. 6A). As expected, we observed up-regulation of LUC7L and depletion of PFKM in LUC7L2$^{KO}$ cells as well as differential expression of multiple glycolytic enzymes (Table S8). Importantly, while abundance of the U1 snRNP and splicing-related proteins was not globally affected by LUC7L2 depletion, an unbiased gene ontology analysis revealed a strong enrichment for OXPHOS proteins, with "NADH dehydrogenase complex" being the top scoring GO term associated with up-regulated proteins in LUC7L2$^{KO}$ cells (P<10$^{-4}$) (FIG. S6A). The anti-correlation between LUC7L2 and OXPHOS protein expression was striking and also observed in two in vivo mouse tissue proteomic atlases, where abundance of Luc7l2 significantly anti-correlated with OXPHOS across organs (P<10$^{-42}$, Wilcoxon) (Geiger et al., 2013, Huttlin et al., 2010) (FIG. S5D, S6B). A similar anti-correlation was observed in a proteomics study of brains from healthy subjects or from patients with neurodegenerative disease and showed that LUC7L2 protein accumulates in patients, whereas OXPHOS proteins is decreased in PD (FIG. S6C) (Ping et al., 2018). While OXPHOS protein abundance decreases in skeletal muscle with aging, as recently confirmed by a proteomic study on 58 skeletal muscle biopsies (Ubaida-Mohien et al., 2019), in this study too, we observed significant up-regulation of LUC7L2 with age and anti-correlation with OXPHOS (P<10$^{-26}$ Wilcoxon) (FIG. S6B). Thus, in these four in vivo datasets from mouse and humans, there appears to be an inverse relationship between the abundance of LUC7L2 and OXPHOS proteins, and accordingly LUC7L2 transcripts accumulate in a mouse model of mitochondrial myopathy, where OXPHOS is compromised and glycolysis is high (Tyynismaa et al., 2010).

Increased OXPHOS protein levels also occur in glycolysis-limiting conditions, such as during galactose growth (Rossignol et al., 2004). To understand whether the increased abundance of OXPHOS proteins was attributable to the effect of LUC7L2 on glycolysis, we performed proteomic analysis of cells grown in galactose. There too, OXPHOS proteins were strongly up-regulated. Importantly, we noticed a similar pattern in both LUC7L2$^{KO}$ cells and in galactose: the up-regulation of subunits of the respiratory chain (RC) complex I, III, IV (FIG. 6A-C, S6D). In contrast, the protein subunits of RC complex II and the ATP synthase, as well as mtDNA genes and global mitochondrial abundance and translation were not affected (FIG. 6A-E, S6E-G). Transcripts of RC complexes I+III+IV did not accumulate in LUC7L2$^{KO}$, suggesting a non-transcriptional mechanism (FIG. 6C). However, RC complexes I+III+IV have the ability to interact within the mitochondrial inner membrane to form "supercomplexes" (SCs), and their proposed roles in reinforcing RC complex stability (Acin-Perez et al., 2004) could explain their accumulation in LUC7L2$^{KO}$ cells. Accordingly, blue-native PAGE confirmed accumulation of higher molecular weight RC complexes in both K562 and HeLa LUC7L2$^{KO}$ and galactose-grown cells (FIG. 6F-G, S6H).

Galactose growth and LUC7L2 depletion both attenuate glycolysis, and we next directly tested whether lower glycolytic rates could explain supercomplex formation. We used CRISPR/Cas9 to acutely deplete six glycolytic enzymes and subsequently measured OXPHOS protein expression (FIG. 6H, S6I). Importantly, we found that depletion of these genes generally led to the accumulation of the same RC subunits as LUC7L2$^{KO}$ and galactose, which was particularly apparent upon depletion of ENOL and TPI1. While the mechanism by which attenuated glycolysis leads to RC complex accumulation was not investigated here, our observations indicate that the increased abundance of RC complexes in LUC7L2$^{KO}$ occurs by a mechanism that is likely secondary to the effect of this gene on glycolysis (FIG. 6I), and possibly involves the stabilization of mitochondrial SCs.

Example 8—LUC7L2 Loss Causes Altered Splicing of the Cystine/Glutamate Antiporter SLC7A11 (xCT) that Fuels OXPHOS Finally, we addressed the molecular basis for the second crossover observed in LUC7L2-depleted cells at the level of cystine/glutamate antiporter and glutamate anaplerosis (FIG. 3, 7A). First, we tested whether this transporter regulates respiration and found that while inhibition with sulfasalazine (SAS) prevented glutamate secretion and promoted maximal respiration, over-expression of the xCT alone restored glutamate secretion in LUC7L2$^{KO}$ in K562 cells (FIG. S7A-E), indicating that SLC7A11 is limiting for glutamate metabolism and OXPHOS. We next examined whether subunits of the $X_c^-$ require LUC7L2 for their expression: SLC3A2 transcripts were not affected by LUC7L2 depletion (Table S6, 7) but we found significant decrease in transcript abundance of SLC7A11 in LUC7L2' HeLa and K562 cells (FIG. 7B). A reduced inclusion of SLC7A11 exon 7 was detected by rMATS in LUC7L2$^{KO}$ K562 cells ($\Delta\psi$=-0.25, FDR<6×10$^{-11}$) and we noticed the presence of a second exon skipping event at exon 9, which was previously annotated and confirmed by RT-PCR and Sanger sequencing (FIG. 7C-D, S7F). Skipping of exon 7 and/or 9 resulted in a PTC in SLC7A11 transcripts (FIG. 7C), likely reducing mRNA abundance via NMD (FIG. S7G), and LUC7L2-binding was also observed at the 5'SS of these exons by eCLIP (FIG. 7C). Accordingly, depletion of LUC7L2 led to a decrease in xCT expression in K562, HeLa and HAP1 cells (FIG. 7E). Loss of xCT was also observed upon depletion of SNRPA and SNRNP70, the two other U1 snRNP subunits identified in our screen (FIG. S7H). Furthermore, we found that LUC7L2 over-expression was sufficient to stabilize both SLC7A11 transcript and protein (FIG. S7I-J).

Figure 1:
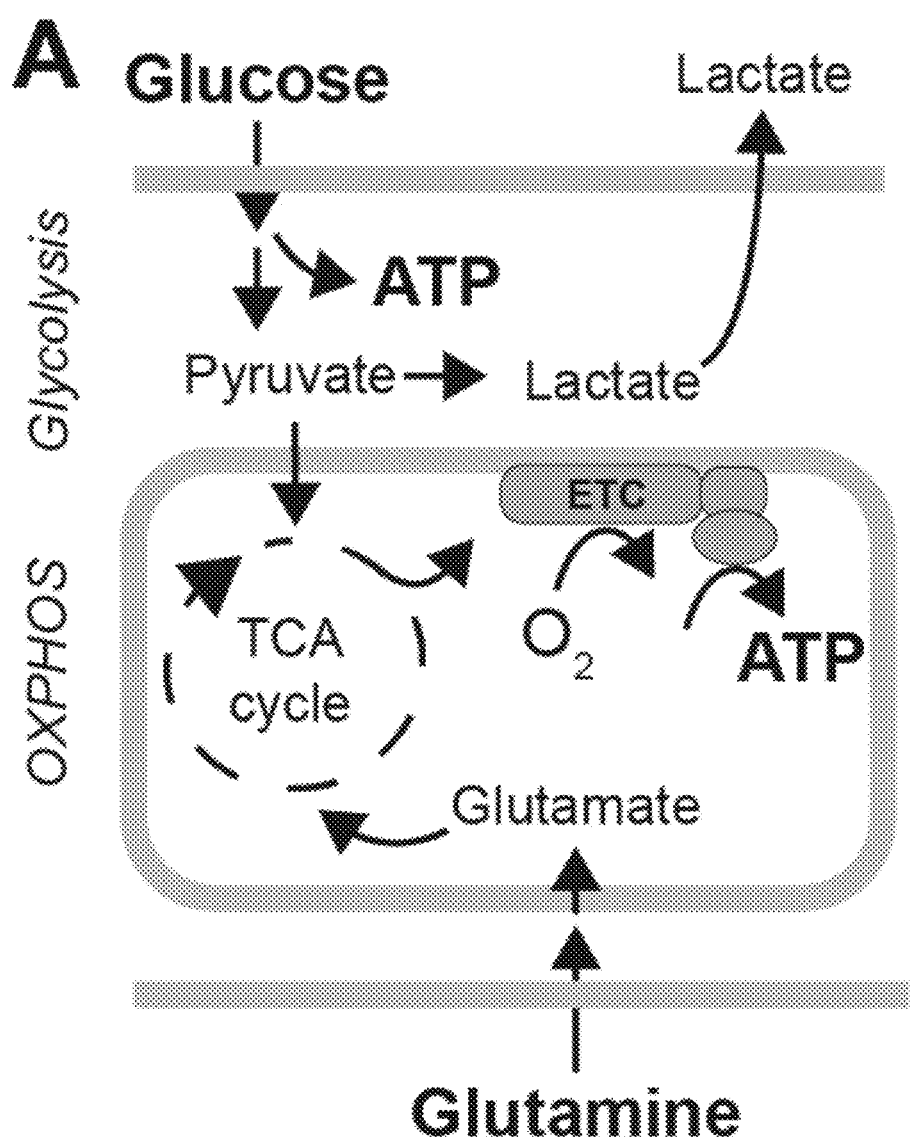
FIG. 1. (A) Overview of the main ATP-generating pathways in cells. OXPHOS: oxidative phosphorylation. ETC.
Figure 1:
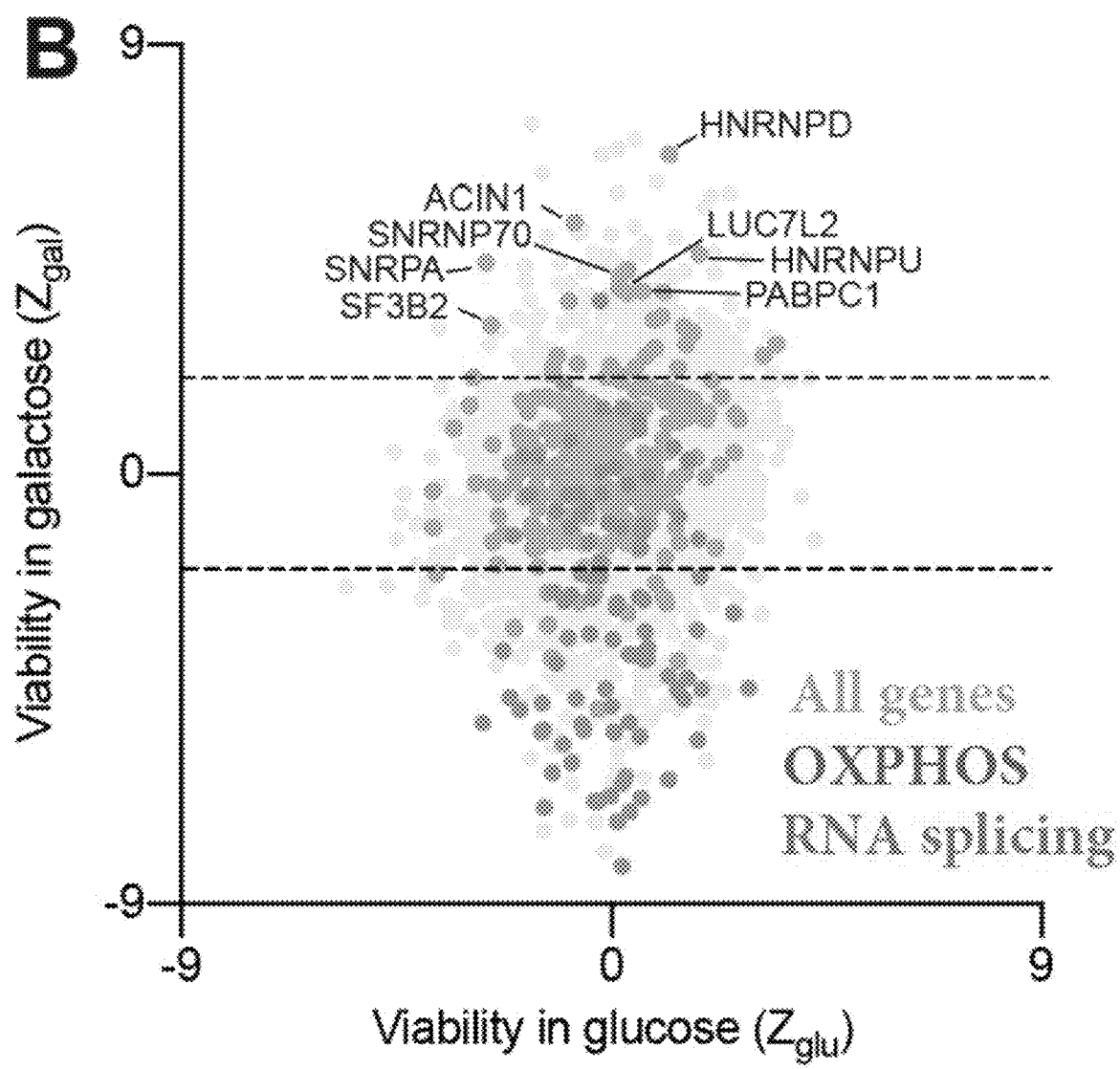
Figure 1:
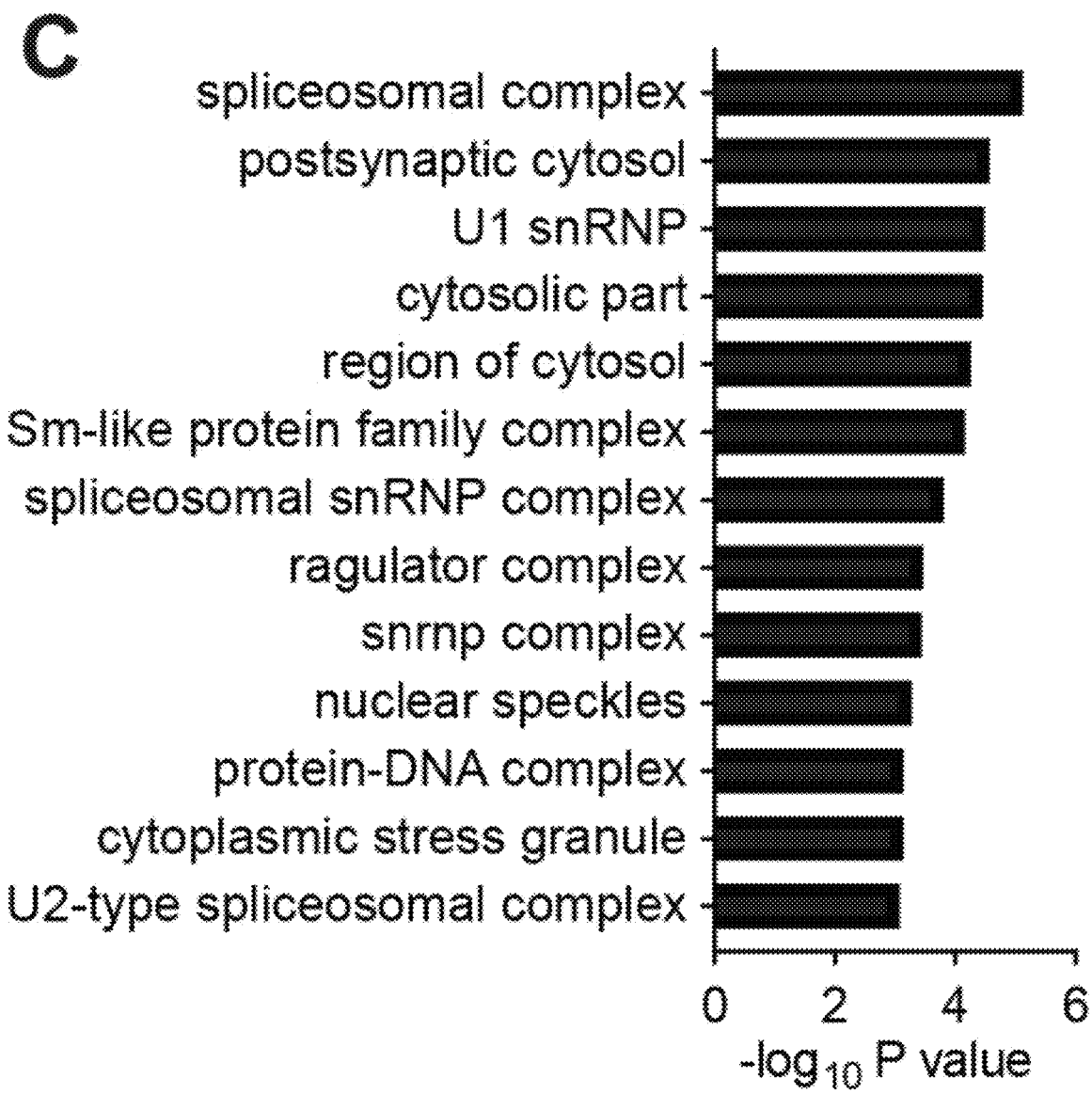
Figure 1:
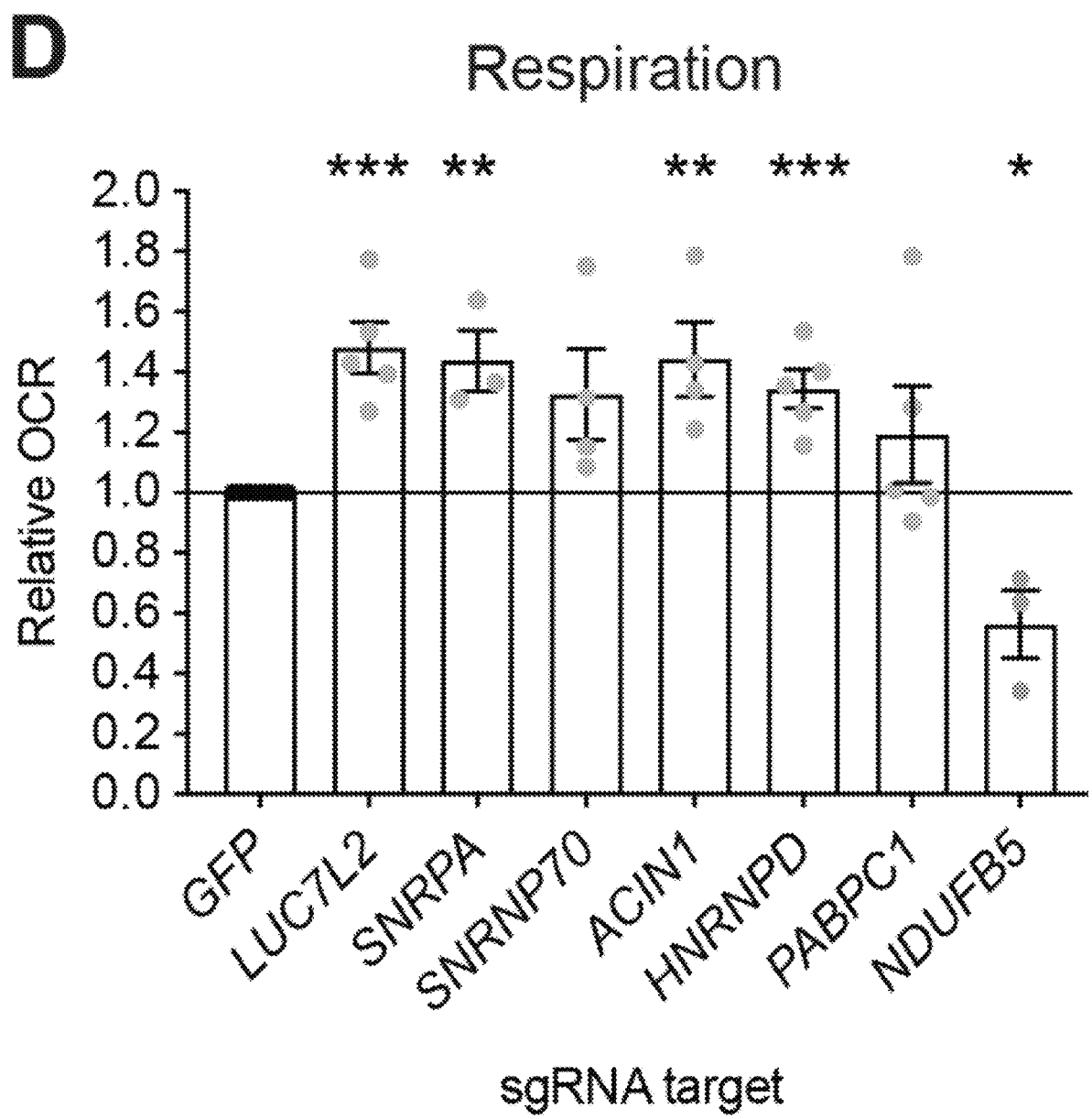
Figure 1:
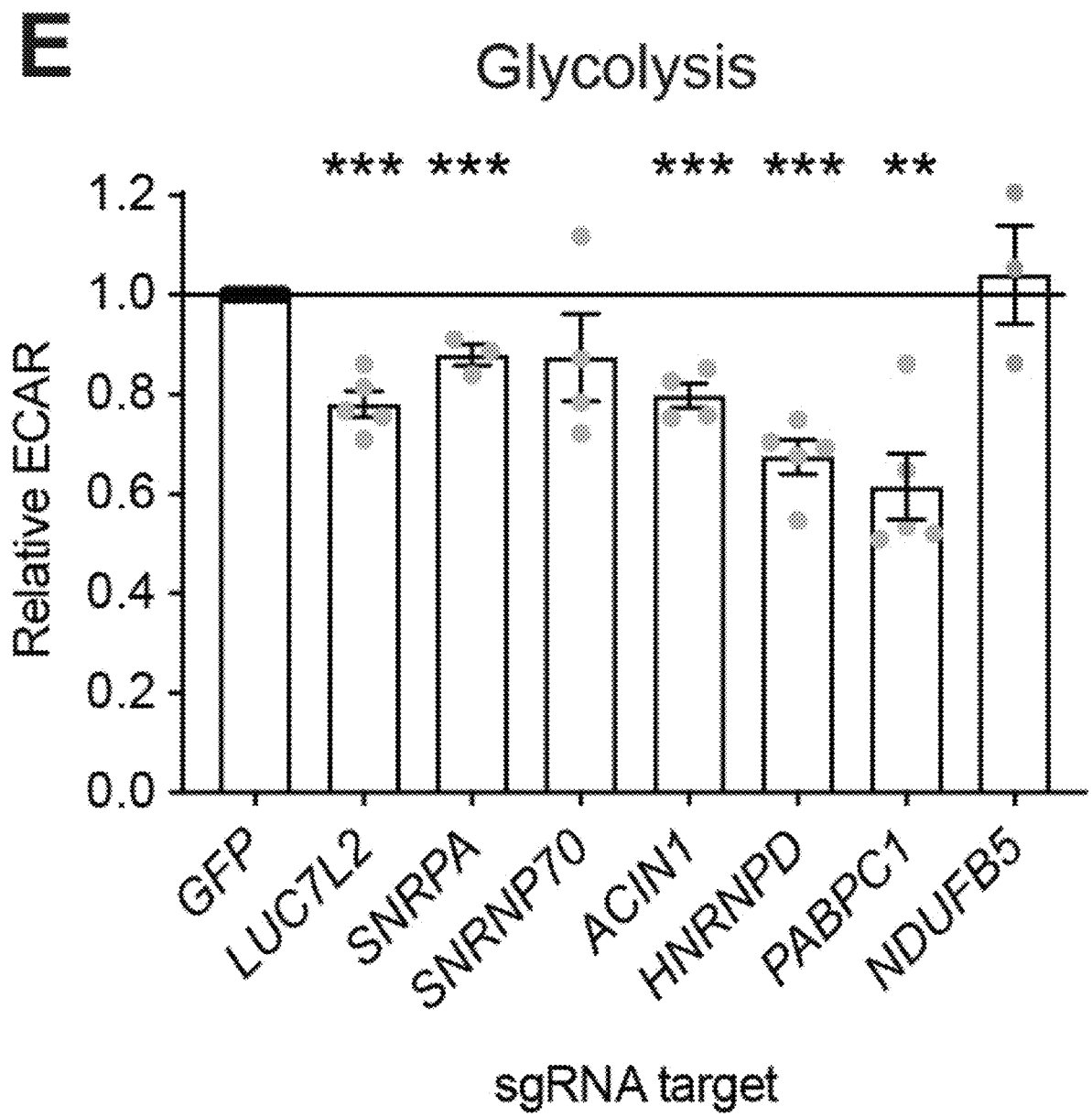
Figure 1:
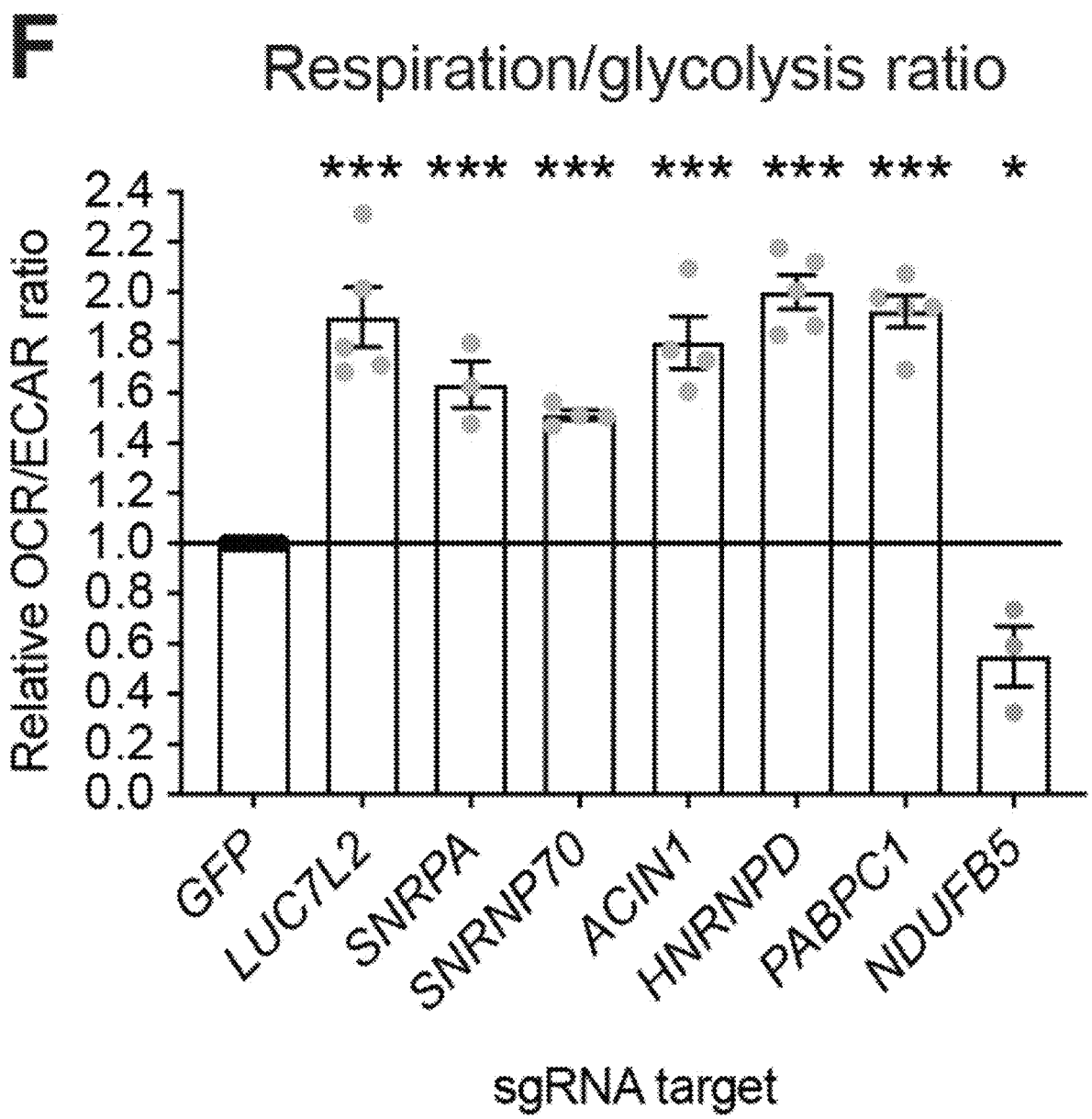

To test for a direct contribution of SLC7A11 splicing in mediating the metabolic phenotypes observed in LUC7L2$^{KO}$, we focused on LUC7L2$^{KO}$ HAP1 cells, a cell line in which the role of the xCT in antagonizing viability in low glucose conditions is well characterized (Shin et al., 2017). As in K562 cells, we found that LUC7L2 depletion increased OXPHOS activity (FIG. S2F) and viability in galactose (FIG. 7F). We then treated HAP1 cells with ASOs targeting the 5'SS of SLC7A11 exon 7 and 9, where LUC7L2 and the U1 snRNP bind. Similar to LUC7L2')

cells, we found that acute ASO treatment led to skipping of these exons, prevented xCT expression and glutamate secretion, and boosted maximal respiration and viability in galactose (FIG. 7G-J), all resembling the phenotype observed upon LUC7L2-depletion in our original screen. Together, we conclude that LUC7L2 and the U1 snRNP are limiting factors required for the correct splicing and expression of SLC7A11, which is consistent with the patterning of metabolism we observed upon LUC7L2 depletion (FIG. 3) and to their improved viability in glycolysis-limiting conditions (FIG. 1).

Example 9—Collective Discussion of Examples 1-8

We have found that the expression of genes related to pre-mRNA splicing and the U1 snRNP impact the balance between glycolysis and OXPHOS. Genetic loss of any three (SNRPA, SNRNP70, LUC7L2) of the four specific subunits of the U1 snRNP boosts cellular fitness when glycolysis is compromised. The U1 snRNP plays an essential role in pre-mRNA splicing and other nuclear RNA-related processes such as cleavage and polyadenylation (Berg et al., 2012) and chromatin retention of non-coding RNAs (Yin et al., 2020). To our knowledge, our work is to first to establish a link between the U1 snRNP and energy metabolism.

In the current study we were able to confirm that LUC7L2 is a genuine component of the U1 snRNP in humans. In yeast and in plants, LUC7 homologs are well characterized component of the U1 snRNP (de Francisco Amorim et al., 2018, Fortes et al., 1999). The human genome encodes three LUC7 paralogs (LUC7L, LUC7L2, LUC7L3). Because LUC7 genes are expressed in a tissue-specific manner (FIG. S5D), as are some of the transcripts bound by LUC7L2, we speculate that their relationship to OXPHOS and glycolysis may show cell type specificity. Future studies will be required to investigate these paralogs across different cell states and the pre-mRNAs that they bind.

The relationship between the expression of the U1 snRNP, LUC7L2 and the OXPHOS/glycolysis balance involves multiple mechanisms and resembles other energy metabolism programs, such as those controlled by PGC1α and HIFα (Puigserver et al., 1998, Huang et al., 1998). Similar to LUC7L2, the programs triggered by these genes is based on on a multitude of genes that cooperate to impact energy metabolism. In this work, we have explored three aspects of the LUC7L2 program: First, we show that LUC7L2 directly impacts glycolysis and glycogenesis by ensuring splicing and expression of multiple glycolytic enzymes, including PFKM. Highly relevant to our observations in LUC7L2$^{KO}$ cells, a recent screen for small molecules that shift energy metabolism from glycolysis to OXPHOS identified a strong effect for tryptolinamide, a novel PFK inhibitor. Second, we show that LUC7L2 directly impacts glutamate anaplerosis by ensuring splicing and expression of the cystine-glutamate exchanger SLC7A11. Third, LUC7L2 impacts assembly of the mitochondrial supercomplexes, a phenomenon that was already reported during galactose growth (Rossignol et al., 2004), and that we show is secondary to the inhibition of glycolysis. These three events explain a significant fraction of the metabolic phenotype observed in LUC7L2$^{KO}$ cells— including glycogen storage, glutamate secretion, increased OXPHOS and survival on galactose. Additional studies are needed to fully characterize the metabolic remodeling triggered by LUC7L2 expression, and in particular how the reduction in glycolysis increases RC assembly, as it may generalize to other metabolic programs.

We have identified alternative splicing events in SLC7A11 whereby exclusion of exons 7 and 9 leads to loss of the SLC7A11 protein. The inventors were able to target both the 5' splice site of exons 7 and 9 to achieve mRNA lacking both exons 7 and 9. The inventors were also capable of targeting both the 3' splice sites of exons 7 and 9 to achieve mRNA lacking both exons 7 and 9. xCT has emerged as a critical regulator of energy metabolism and cell viability, and while high expression of SLC7A11 blunts glutamine anaplerosis and creates a dependency on glycolysis for ATP production (Koppula et al., 2017, Shin et al., 2017), genetic ablation of this cancer-related gene in tumors induces death by lipid peroxidation (Badgley et al., 2020). Expression of SLC7A11 is highly regulated and is known to be activated by ATF4 (Sato et al., 2004) and NRF2 (Shin et al., 2017) and repressed by P53 (Jiang et al., 2015). SLC7A11 activity is also regulated by direct mTORC2 phosphorylation (Gu et al., 2017). To our knowledge, direct regulation of SLC7A11 expression by pre-mRNA splicing has not been previously reported and our work adds an extra layer of complexity to the regulation of this transporter. In the future, it will be interesting to determine whether these splicing events are regulated in disease states to influence the sensitivity to lipid peroxidation and ferroptosis.

Our work predicts that shifts in energy metabolism may accompany human conditions associated with LUC7L2 and other splicing-related genes. U1 snRNP activity and U1 snRNA mutations have been reported to frequently occur in cancer (Shuai et al., 2019, Suzuki et al., 2019, Oh et al., 2020). Similarly, mutations in LUC7L2 or haploinsufficiency through chromosome 7q loss, where LUC7L2 resides, are associated with MDS (Singh et al., 2013). Patient-derived and engineered models of 7q-recapitulate differentiation defects observed in MDS (Kotini et al., 2015) and reintroduction of LUC7L2 in this model is sufficient to restore differentiation. How LUC7L2 loss blunts hematopoietic stem cell differentiation and MDS is not clear, but our work invokes the possibility of a bioenergetics mechanism. It is notable that other splicing factors associated with MDS also participate in the splicing of metabolic enzymes and, for example, MDS-associated mutations in SRSF2 give rise to the exact same splicing change in PFKM (Zhang et al., 2015) as we observe following LUC7L2 loss. Our experiments (FIG. 2C) further predict that pharmacological blockade of OXPHOS using drugs such as metformin may be beneficial in these disorders.

It is important to emphasize that our current analyses focused on the constitutive effects of LUC7L2 depletion on energy metabolism. An important future goal will be to determine whether this process is regulated in physiological and pathological contexts. Expression of LUC7L2 and its paralogs are known to respond to changes in the environment, including changes in oxygen tension (Kimura et al., 2004, Gao et al., 2011), and we observe that across multiple datasets LUC7L2 and OXPHOS anti-correlate in vivo (FIG. S6B). Our experiments support the notion that LUC7L2 expression is limiting for the glycolysis/OXPHOS balance, as its over-expression presents the opposite phenotype as its depletion on oxygen consumption and xCT levels (FIG. 5D, S7I,J). It is notable that previous large-scale proteomics studies have established that LUC7L2 is post-translationally modified via phosphorylation and hydroxylation (Webby et al., 2009, Dephoure et al., 2008). In this context it is possible that proteins of the LUC7 family and, more generally the U1 snRNP, might integrate signals such as oxygen and nutrient availability to regulate energy metabolism.

Pre-mRNA splicing, gene expression and energy metabolism are cell specific processes. We report here that LUC7L2 impacts metabolism in three cellular models, but that differences exist across cell types. For example, while we observed decreased levels of xCT in all three LUC7L2$^{KO}$ cell lines investigated (FIG. 7E), it was not sufficient to lead to a detectable increase in net oxygen consumption in HeLa cells (FIG. S2E). It is possible that cells with different metabolic programs, for example those with low SLC7A11 and PFKM expression, or cells with high expression of LUC7L and LUC7L3, might be indifferent to LUC7L2 depletion.

Example 10—Granular Disclosure of the Methods Utilized in Examples 1-9

Cell Lines

K562 (ATCC CCL-243), HeLa (ATCC CCL-2) and 293T (ATCC CRL-3216) were obtained from ATCC and were re-authenticated by STR profiling at ATCC prior submission of the manuscript. HAP1 cells were from Horizon Discovery (C631). Cells were periodically tested to ensure absence of mycoplasma.

Cell Culture and Cell Growth Assays

Unless otherwise specified, cells were maintained in DMEM containing 1 mM sodium pyruvate (ThermoFisher Scientific) with 25 mM glucose, 10% fetal bovine serum (FBS, ThermoFisher Scientific), 50 µg/mL uridine (Sigma), and 100 U/mL penicillin/streptomycin (ThermoFisher Scientific) under 5% CO2 at 37° C. Cells were counted using a ViCell Counter (Beckman) and only viable cells were considered. Drugs were diluted in the same culture media for cell growth assays and compared to the solvent control (DMSO or water). For galactose growth assays, FBS was replaced by dialyzed FBS (Life Technologies) and glucose was replaced by an equivalent amount of galactose.

Gene-Specific CRISPR-Cas9 Knockouts

The two best sgRNAs from the Avana-library were ordered as complementary oligonucleotides (Integrated DNA Technologies) and cloned in pLentiCRISPRv2. An sgRNA targeting EGFP was used as a negative control. Lentiviruses were produced according to Addgene's protocol (Sanjana et al., 2014) and cells were selected with 2 mg/mL puromycin (ThermoFisher Scientific) for 48 h 24 h post-infection. Cells were then maintained in routine culture media for 10-20 addition days before analysis. Gene disruption efficiency was verified by qPCR and/or immunoblotting. For HAP1 cells, a LUC7L2KO cell line expressing LUC7L2 cDNA was used as control (LUC7L2Rescue). For acute treatment, K562 cells were transduced with a high titer of sgRNAs targeting LUC7L2 and analyzed after 7 days. Sequences of the sgRNAs used are in the Key Resources Table.

Antisense Oligonucleotides (ASOs) Treatment

2×105/mL HAP1 cells were seeded in a culture or seahorse plate. 24 h later, the media was replaced by fresh media containing 10 µM of the specific or control ASO, and 6 µL/mL of PEG-based endoporter (GeneTools). Cells were analyzed 48 h-72 h later and recounter after the experiment.

Oxygen Consumption and Extracellular Acidification Rate by Seahorse XF Analyzer 1.25×105 K562 cells were plated on a Seahorse plate in Seahorse XF DMEM media (Agilent) containing 25 mM glucose and 4 mM glutamine (ThermoFisher Scientific). Oxygen consumption and extracellular acidification rates were simultaneously recorded by a Seahorse XFe96 Analyzer (Agilent) using the mito stress test protocol, in which cells were sequentially perturbed by 2 mM oligomycin, 1 µM CCCP and 0.5 mM antimycin (Sigma). Data were analyzed using the Seahorse Wave Desktop Software (Agilent). Data were not corrected for carbonic acid derived from respiratory CO2. For seahorse in HeLa and HAP1 cells, 5×104 and 1×105 cells were plated in a 96-well seahorse plate the day before the experiment (respectively). Cells were trypsinized after the experiment and recounted and the data was normalized to cell number.

Mitochondrial and Nuclear DNA Determination

Mitochondrial and nuclear DNA determination was carried as previously described (Bao et al., 2016). LUC7L2WT and LUC7L2KO K562 cells were grown for 24 h in fresh cell culture media and counted. 1×105 cells from each condition (n=3) were harvested and lyzed in 100 uL mtDNA lysis buffer (25 mM NaOH, 0.2 mM EDTA) before incubation at 95° C. for 15 min. 100 uL of 40 mM Tris-HCl pH 7.5 was added to neutralize the reaction on ice. Samples were diluted 50× and the ratio between mitochondrial and nuclear DNA was determined using a custom Taqman based assay and qPCR using a CFx96 quantitative PCR machine (Biorad). Relative mtDNA abundance was determine using the ΔΔCt method.

RNA-Extraction, Reverse Transcription and qPC qPCR was performed using the TaqMan assays (ThermoFisher Scientific). RNA was extracted from total cells with an RNeasy kit (QIAGEN) and DNase-I digested before murine leukemia virus (MLV) reverse transcription using random primers (Promega) and a CFx96 quantitative PCR machine (rad). All data were normalized to TBP using ΔΔCt method.

Citrate Synthase Activity Determination

Citrate synthase activity was determined using a commercially available kit (Abcam). LUC7L2WT and LUC7L2KO K562 cells were grown for 48 h in fresh cell culture media and counted. 5×106 cells from each condition (n=3) were harvested, washed in PBS and resuspended in lysis buffer (provided by the kit) and completed with protease inhibitor. 100 uL of lysate was used and the experiment was performed as described in the kit protocol. Protein abundance was determined using a DC protein assay (Biorad) and the citrate synthase activity signal was normalized to the protein abundance of each sample.

Glycogen Determination

Glycogen synthase activity was determined using a commercially available kit (Abcam). LUC7L2WT and LUC7L2KO K562 cells were grown for 24 h in fresh cell culture media and counted. 1×106 cells from each condition (n=8) were incubate in fresh media for another 6 h before harvested, washed in ice-cold PBS and resuspended in lysis buffer (provided by the kit). 25 uL of lysate was used and the experiment was performed as described in the kit protocol and normalized to total protein abundance.

Glutamate Determination

Glutamate levels were determined using a commercially available AMPLEX kit (Life Technologies). LUC7L2WT, LUC7L2Rescue (LUC7L2KO cells were a LUC7L2 cDNA was stably expressed), LUC7L2KO and ASO treated K562 or HAP1 cells were grown for 24 h in fresh culture media and counted. Cells were then washed with PBS, the media was replaced and the cells were incubated for another 3 h. Medias were then collected and centrifuged at 2,000 g for 3 min, and glutamate concentrations were determined from the supernatant.

Cell Viability Assay in Galactose

To measure viability in galactose, cells were PBS washed and counted and an equal number of cells was seeded in culture media containing 25 mM glucose or 25 mM galactose. 24h later, cells were collected and viable cells were determined using a Vi-Cell Counter (Beckman).

Electron Microscopy

5×10⁶ LUC7L2WT and LUC7L2KO K562 cells were grown for 24 h in fresh cell culture media and were fixed in 2.5% gluteraldehyde, 3% paraformaldehyde with 5% sucrose in 0.1M sodium cacodylate buffer (pH 7.4), pelletted, and post fixed in 1% OsO4 in veronal-acetate buffer. The cells were stained en block overnight with 0.5% uranyl acetate in veronal-acetate buffer (pH6.0), then dehydrated and embedded in Embed-812 resin. Sections were cut on a Leica EM UC7 ultra microtome with a Diatome diamond knife at a thickness setting of 50 nm, stained with 2% uranyl acetate, and lead citrate. The sections were examined using a FEI Tecnai spirit at 80 KV and photographed with an AMT CCD camera.

Confocal Microscopy and Immunofluorescence

HeLa cells were transduced with pWPI-LUC7L2-FLAG at least 48 h before the experiment and grown on coverslips until 30-50% confluent. Cells were successively fixed in 4% paraformaldehyde in cell culture media at room temperature for 30 min, blocked/permeabilized for 30 min in Abdil buffer (PBS+0.1% Triton X-100+3% bovine serum albumin (w/v)), incubated with primary antibodies (1:200) in Abdil buffer for 1 h, washed 3×5 min in PBS+0.1% Triton X-100, incubated in fluorophore-coupled secondary antibodies (1:1000) and hoescht (1:10000) in Abdil for 30 min, washed 3× in PBS+0.1% Triton X-100 and mounted on a slide using FluorSave (EMD Millipore). Cells were imaged using a Zeiss LSM700 confocal microscope Polyacrylamide Gel Electrophoresis and Immunoblotting Cells were harvested, washed in PBS and lysed for 5 min on ice in RIPA buffer (25 mM Tris pH 7.5, 150 mM NaCl, 0.1% SDS, 0.1% sodium deoxycholate, 1% NP40 analog, 1× protease (Cell Signaling) and 1:500 Universal Nuclease (ThermoFisher Scientific). Protein concentration was determined from total cell lysates using DC protein assay (Biorad). Gel electrophoresis was done on Novex Tris-Glycine gels (ThermoFisher Scientific) before transfer using the Trans-Blot Turbo blotting system and nitrocellulose membranes (Biorad). All immunoblotting was performed in Intercept Protein blocking buffer (Licor). Washes were done in TBS+0.1% Tween-20 (Sigma). Specific primary antibodies were diluted 1:100-1:5000 in blocking buffer. Fluorescent-coupled secondary antibodies were diluted 1:10,000 in blocking buffer. Membranes were imagined with an Odyssey CLx analyzer (Licor) or by chemoluminescence. In a few instances, the same lysates were loaded on parallel gels to avoid antibody cross-reactivity, or because the proteins of interest could not be resolved on the same percentage gels. In these cases, a loading control is provided for all gels, and panels from the same immunoblots are connected with a dotted line on the figure. All raw immunoblots pictures are provided in the supplemental information document.

Liquid Chromatography-Mass Spectrometry (LC-MS)

Intracellular Metabolite Profiling

LUC7L2WT and LUC7L2KO K562 cells were pre-incubated overnight in profiling media containing glucose-free DMEM media (ThermoFisher Scientific), 10% dialyzed FBS (ThermoFisher Scientific), penicillin and streptomycin (ThermoFisher Scientific) and 25 mM glucose (Sigma) but omitting supplemental pyruvate or uridine. On the day of the experiment, 2.5×10⁶ cells were seeded in 3 mL of profiling media in a 6-well plate (n=6 replicate plates for each genotype). An additional well containing 3 mL of media but no cells was included as control. After 8 h of incubation, cells were centrifuged at 300 g for 3 min at room temperature and the culture media was saved and frozen at −80° C. until further analysis (described below). The cell pellet was briefly washed in ice-cold 150 mM NaCl and centrifuged again. 1 mL dry ice-cold 80% methanol was then added to quench metabolism. Cells were incubated on ice for >20 min, centrifuged at 20,000 g (4° C.) and the supernatant was saved and dried down in a speed vacuum concentrator (Savant SPD 1010, ThermoFisher Scientific) and stored at −80° C. until analysis. On the day of analysis, samples were re-suspended in 1204, of 60/40 acetonitrile/water, vortexed, sonicated in ice-cold water for 1 min, incubated on ice for 20 min and the supernatant was collected in an autosampler vial after centrifugation at 21,000 g for 20 min at 4° C. Pooled quality control (PooledQC) samples were generated by combining ~20 μL of each sample. Metabolite profiling was performed using a Dionex Ultimate 3000 UHPLC system coupled to a Q-Exactive Plus orbitrap mass spectrometer (ThermoFisher Scientific, Waltham, MA) with an Ion Max source and HESI II probe operating in polarity switching mode. A zwitterionic zic pHilic column (150×2.1 mm, 5 μm, Merck KGaA) was used for polar metabolite separation. Mobile phase A (MPA) was 20 mM ammonium carbonate in water, pH9.6 (adjusted with ammonium hydroxide) and MPB was acetonitrile. The column was held at 27° C., with an injection volume of 5 μL, and an autosampler temperature of 4° C. The LC conditions at a flow rate of 0.15 mL/min were: 0 min: 80% B, 0.5 min: 80% B, 20.5 min: 20% B, 21.3 min: 20% B, 21.5 min: 80% B with 7.5 min of column equilibration time. MS parameters were: sheath gas flow=30, aux gas flow=7, sweep gas flow=2, spray voltage=2.80 for negative & 3.80 for positive ion modes, capillary temperature=310° C., S-lens RF level=50 and aux gas heater temp 370° C. Data acquisition was performed using Xcalibur 4.1 (ThermoFisher Scientific) in full scan mode with a range of 70-1000 m/z, a resolving power of 70,000, an AGC target of 1×10⁶, and a maximum injection time of 80 ms. Data analysis was done using Compound Discoverer 3.0. Samples were injected in a randomized order and pooled QC samples were injected regularly throughout the analytical batches. Metabolite annotation was based on accurate mass (±5 ppm) and matching retention time (±0.3 min) as well as MS/MS fragmentation pattern from the pooled QC samples against in-house retention time+MSMS library of reference chemical standards. Metabolites which had a pooled QC CV<20% were used for the statistical analysis.

Media Profiling

30 μL of control or spent media was mixed with 120 μL of ice-cold acetonitrile containing the metabolomics amino acid mix from Cambridge Isotope Labs (MSK-A2-1.2), 13C6-glucose, 13C3-pyruvate, and 13C3-lactate as internal standards, was vortexed, incubated on ice for 20 min, centrifuged at 21,000 g for 20 min at 4° C. and the supernatant was transferred to an autosampler vial for LC-MS analysis. Calibration curves were prepared in water at varying concentration levels depending on the amino acid level in the DMEM media formulation. Metabolite separation was done using XBridge BEH amide (2.1×150 mm, 1.7 μm, Waters Corporation, MA). Mobile phase A was 90/5/5 water/acetonitrile/methanol, 20 mM ammonium acetate, 0.2% acetic acid and mobile phase B was 90/10 acetonitrile/water, 10 mM ammonium acetate, 0.2% acetic acid. The column temperature was 40° C. and flow rate was 0.3 mL/min. The chromatographic gradient was: 0 min: 95% B, 9 min: 70% B, 9.75 min: 40% B, 12 min: 40% B, 13 min: 30% B, 14 min: 30% B, 14.1 min: 10% B, 17 min: 10% B, 17.5 min: 95% B, 22 min: 95% B. MS parameters were: sheath gas flow=50, aux gas flow=12, sweep gas flow=2, spray voltage=2.80 for negative (3.50 for positive), Capillary temperature=320° C., S-lens RF level=50 and aux gas heater temperature 380° C. Data acquisition was done using Xcalibur 4.1 (ThermoFisher Scientific) and performed in full scan mode with a range of 70-1000 m/z, a resolving power of 70,000, an AGC target 106, and a maximum injection time of 100 ms. Tracefinder 4.1 was used for quantitation analysis. One LUC7L2KO sample gave aberrant spectra and was excluded.

LUC7L2-3×FLAG Immunoprecipitation and Mass Spectrometry

For immunoprecipitation, a 3×FLAG-tagged version of LUC7L2 was cloned into pWPI-Neo (Addgene), and viruses were produced. pWPI-GFP served as control. 293T cells were infected and expanded for at least 48 h. An equal number of cells from each condition in duplicate was lysed in IP lysis buffer (50 mM Tris/HCl (pH 7.5), 150 mM NaCl, 1 mM MgCl2, 1% NP-40, 0.1% sodium deoxycholate, 1× protease (Cell Signaling). Lysates were cleared by centrifugation at 20,000 g for 20 min and the supernatants were saved. Washed FLAG M2 magnetic beads (Sigma) were added to the lysate and incubated overnight at 4° C. Beads were recovered after extensive washing, and the protein/RNA complexes were eluted with 100 m/mL 3×FLAG peptide (Sigma). For protein isolation, the eluate was run on an SDS-PAGE gel until the whole lysate entered the gel. Single bands containing all proteins from the sample were then cut and analyzed by mass spectrometry at the Whitehead proteomics facility. Peptides were identified and quantified using the Top 3 total ion current (TIC) method (Scaffold4). Interacting proteins were considered positive when they were enriched >2-fold over either control and identified only by unique peptides.

Enhanced Crosslinking and Immunoprecipitation (eCLIP)

Libraries were generated using standard seCLIP methods according to published protocols (Van Nostrand et al., 2017). In brief, K562 and Hela cells (2×107 for each replicate plate) were UV crosslinked (254 nm, 400 mJ/cm2), then lysed and sonicated (Bioruptor) in eCLIP lysis buffer (50 mM Tris-HCl pH 7.4, 100 mM NaCl, 1% NP-40 (Igepal CA630), 0.1% SDS, 0.5% sodium deoxycholate (protect from light), 1:200 Protease Inhibitor Cocktail I, in RNase/DNase-free H2O). RNA fragments were created by incubating lysates with RNase I (Ambion) and LUC7L2:RNA complexes were immunoprecipitated for 2 h at 4° C. using Dynabeads bound to 4 micrograms of LUC7L2-specific affinity-purified antibody. In parallel, libraries were generated from size-matched input (SMInput) samples containing RNAs present in the whole cell lysates, i.e. sans RBP-specific IP. For the IPs, a series of stringent washes (High salt wash buffer: 50 mM Tris-HCl pH 7.4, 1 M NaCl, 1 mM EDTA, 1% NP-40, 0.1% SDS, 0.5% sodium deoxycholate (protect from light), in RNase/DNase-free H2O; Wash buffer: 20 mM Tris-HCl pH 7.4, 10 mM MgCl2, 0.2% Tween-20, in RNase/DNase-free H2O.) was followed by RNA dephosphorylation with FastAP (ThermoFisher Scientific) and T4 PNK (NEB) then ligation of an adaptor to the 3 ends of the RNAs with T4 RNA ligase 1 (NEB). Protein:RNA complexes were separated on 4-12% polyacrylamide gels, transferred to a nitrocellulose membranes, and RNA was extracted from the membranes using Proteinase K (NEB). Immunoprecipitation was confirmed by parallel western blotting of fractions of each sample with the antibody described previously. Following purification, SMInput RNA were dephosphorylated and 3'-ligated and all samples were reverse transcribed with Superscript III (Invitrogen). Free primers were removed with ExoSap-IT (Affymetrix) and a DNA adaptor was ligated to the 3' ends of the cDNA with T4 RNA ligase 1. cDNA was quantified by qPCR and PCR amplified using Q5 Master Mix (NEB) and resulting libraries were purified prior to Illumina sequencing.

Next-Generation RNA Sequencing

Total RNA from LUC7L2WT and LUC7L2KO K562 and HeLa cells (n=3, replicate plates each) were isolated using a RNeasy kit (QIAGEN). RNA sequencing libraries were prepared by the Genomics Platform at the Broad Institute based on the True-Seq protocol (Illumina), which selects for polyadenylated RNA and preserves strand specificity. Libraries were sequenced using a NovaSeq 6000 instrument, generating 2×101 bp paired-end reads with a minimum of 40M pairs per sample. The RNA sequencing data have been deposited to the Gene Expression Omnibus (GEO) with the dataset identifier GSE157917.

Bioinformatic Analyses eCLIP Analysis

Raw reads were mapped using STAR (Dobin et al., 2013) to the hg19 genome following standard ENCODE guidelines (http://labshare.cshl.edu/shares/gingeraslab/www-data/dobin/STAR/STAR.posix/doc/STARmanual.pdf, page 7). Read length was relaxed to accommodate the slightly shorter average eCLIP read length (outFilterMatchNminOverLread 0.33). Duplicate PCR reads were removed from the mapped reads to generate final reads. Mapped reads were then processed into peaks using CLIPper (Lovci et al., 2013) with standard specifications. For each dataset, only peaks shared between two replicates and not appearing in the input controls were considered in subsequent analyses. Reads were then filtered to a robust p-value of P<1e-3 or P<1e-4 as indicated in the manuscript. Using these highest-confidence peaks, a metaplot was created centered on the exon, with an additional 500 bases upstream and 500 bases downstream of the flanking introns. For each region (exonic or intronic), the relative positions of each single base of a CLIP peak were summed and normalized to the mean base coverage in that region.

Gene Expression Analysis

The reads were aligned with STAR (Dobin et al., 2013) to the human genome hg19 using default parameters and a two-pass approach. Following a first pass alignment of each sample, novel splice junctions were pooled across all samples from the same cell type and incorporated into the genome annotation for a second pass alignment. Second pass gene counts derived from uniquely mapping pairs with the expected strandedness were output by STAR. Differential gene expression analysis between LUC7L2WT and LUC7L2KO samples was performed in R using the package DESeq2 (Love et al., 2014). Differentially expressed genes were considered significant below FDR<10-4 and with an absolute fold change value greater than 50%.

Splicing Analysis

Splicing events were analyzed with rMATS.4.0.2 (with three replicates each) using standard specifications and the hg19 genome. Events were considered significant below FDR<0.1 and with an absolute $\Delta\psi$ value greater than 0.05.

Overlap Analyses

Overlap analyses normalized for gene expression were performed as in (Friedman et al., 2008). Briefly, ten bins (percentiles) of gene expression were established for HeLa and K562 cells using the average gene expression from three (LUC7L2) replicates determined by kallisto (Bray et al., 2016) according to standard parameters and averaged TPMs were filtered for TPM>1. For each bin, the percentage of genes within that bin appearing in either corresponding eCLIP- or rMATS-identified affected genes in that cell line. A 10×10 matrix was created by multiplying these frequencies together for each cell. Another 10×10 matrix was then populated by the actual counts of total overlapping genes for each cell. A third 10×10 matrix of expected counts of eCLIP/rMATS was generated from these two matrices and the total number of events were summed for a final expected value. Finally, the actual count of overlapping genes per cell was calculated and summed for the observed value. Significance was estimated with a Poisson test.

Correlation Analysis

Published protein expression datasets (Geiger et al., 2013, Huttlin et al., 2010, Ping et al., 2018, Ubaida-Mohien et al., 2019) were filtered to exclude genes with null values in >20% of samples and remaining missing values were replaced with half the minimum observed for that protein. Each protein was normalized via Z-score and then Pearson correlations were calculated between LUC7L2 profiles and each protein. Anti-correlation with OXPHOS (table S1) was assessed via Wilcoxon Rank Sum test.

CRISPR Screen Analysis

CRISPR screen analysis was performed either using Z-scores (To et al., 2019) and using MAGeCK (Li et al., 2014). Raw sgRNA read counts were normalized to reads per million and then log 2 transformed using the following formula: Log 2(reads from an individual sgRNA/total reads in the sample 106+1). Log 2 fold-change of each sgRNA was determined relative to the pre-swap control. For each gene in each replicate, the mean log 2 fold-change in the abundance of all 4 sgRNAs was calculated. Genes with low expression (log 2 FPKM<0) according to publicly available K562 RNA-seq dataset (sample GSM854403 in GEO series GSE34740) and essential genes previously reported (Arroyo et al., 2016) were removed. Log 2 fold-changes were averaged by taking the mean across replicates. For each treatment, a null distribution was defined by the 3,726 genes with lowest expression. To score each gene within each treatment, its mean log 2 fold-change across replicates was Z-score transformed, using the statistics of the null distribution defined as above. To score each gene using MAGeCK, normalized sgRNA read counts from the duplicate in each condition were used as input for MAGeCK v0.5.3 to obtain a p value and FDR for gene enrichment or depletion relative to the reference samples (pre-swap). MAGeCK was run with default parameters. For representation purpose, viability in galactose was defined as the annexin V value.

Quantitative Proteomics

LUC7L2WT and LUC7L2KO cells were grown in n=3 replicate plates in DMEM media containing 25 mM glucose or 25 mM galactose for 2 weeks. Quantitative proteomics was performed at the Thermofisher for Multiplexed Proteomics (Harvard). In short, cells were harvested and total protein quantification was performed using micro-BCA assay (Pierce). Samples were reduced with DTT and alkylated with iodoacetamide before protein precipitation in methanol/chloroform. Pellets were resuspended in 200 mM EPPS, pH 8.0 and a digestion was performed sequentially using LysC (1:50) and Trypsin (1:100) based on protease to protein ratio. ~50 μg peptide per sample was labeled with TMTpro 16 reagents. A small aliquot of each sample was then combined and analyzed by LC-MS3 to verify labeling efficiency and mixing ratios. Samples were combined, desalted, and dried by speedvac. 14 fractions from the total proteome HPRP set were analyzed on an Orbitrap Eclipse mass spectrometer using a 180 minute method MS3 method with real-time search. Peptides were detected (MS1) and quantified (MS3) in the Orbitrap. Peptides were sequenced (MS2) in the ion trap. MS2 spectra were searched using the COMET algorithm against a custom protein database containing only one protein per gene (referenced as the canonical isoform). Peptide spectral matches were filtered to a 1% false discovery rate (FDR) using the target-decoy strategy combined with linear discriminant analysis. The proteins from the 14 runs were filtered to a <1% FDR. Proteins were quantified only from peptides with a summed SN threshold of >100. Only unique peptides were considered for downstream analysis. The mass spectrometry proteomics data have been deposited to the ProteomeXchange Consortium via the PRIDE (Perez-Riverol et al., 2019) partner repository with the dataset identifier PXD021917 and 10.6019/PXD021917".

Blue-Native PAGE

For blue-native PAGE, a mitochondria-rich fraction was isolated from LUC7L2WT and LUC7L2KO K562 and HeLa cells grown for two weeks in glucose or galactose-containing by differential centrifugation. An equal amount of mitochondria were resuspended in blue-native loading buffer containing 1% digitonin (Life Technologies) before electrophoresis on a 3 to 12% Native PAGE (Life Technologies) according to the manufacturer's instruction. Gels were then fixed and stained with Coomasie R-250, or transferred to PVDF membranes, denatured by 3% acetic acid treatment, destained with methanol, blocked and an immunodetection was performed with the indicated antibodies and secondary HRP-coupled antibodies. Samples were loaded on parallel gels to avoid cross-reactivity between antibodies.

Mitochondrial Translation

Determination of mitochondrial translation products in LUC7L2WT and LUC7L2KO cells was performed as previously described (Jourdain et al., 2013). K562s cells were incubated for 20 min in methionine/cystine-free DMEM (Sigma) complemented with dialyzed serum and 2 mM L-glutamine. Cells were then incubated for 1 h in the same medium in the presence of 100 μg/ml emetine and 100 μCi/μL 35S-labeled methionine/cystine (PerkinElmer). Total protein concentration of cell lysates was measured, and lysates were resolved on an acrylamide gel, transferred to a nitrocellulose membrane, and analyzed by autoradiography. A mitochondrial translation inhibitor (chloramphenicol) was used as a control.

Gene Ontology Analysis

Gene ontology analysis was performed using GOrilla with default settings and using a ranked gene list as input (Eden et al., 2009). Only GO categories with <500 genes and represented by >2 significant genes were considered. Highlighted genes in figures correspond to the GO categories "RNA splicing" (GO:0008380), "U1 snRNP" (GO: 0005685) and "OXPHOS" (manually curated) and GO gene lists are reported in Table 51.

Gene-Specific cDNA Cloning and Expression cDNAs of interest were custom designed (Genewiz or IDT) and cloned into pWPI-Neo or pLV-lenti-puro (Visanji et al., 2011, Hayer et al., 2016) using BamHI/SpeI and BamHI/NotI (NEB), respectively.

REFERENCES

ACIN-PEREZ, R., BAYONA-BAFALUY, M. P., FERNANDEZ-SILVA, P., MORENO-LOSHUERTOS, R., PEREZ-MARTOS, A., BRUNO, C., MORAES, C. T. & ENRIQUEZ, J. A. 2004. Respiratory complex III is required to maintain complex I in mammalian mitochondria. Mol Cell, 13, 805-15.

ARROYO, J. D., JOURDAIN, A. A., CALVO, S. E., BALLARANO, C. A., DOENCH, J. G., ROOT, D. E. & MOOTHA, V. K. 2016. A Genome-wide CRISPR Death Screen Identifies Genes Essential for Oxidative Phosphorylation. Cell Metab, 24, 875-885.

BADGLEY, M. A., KREMER, D. M., MAURER, H. C., DELGIORNO, K. E., LEE, H. J., PUROHIT, V., SAGALOVSKIY, I. R., MA, A., KAPILIAN, J., FIRL, C. E. M., DECKER, A. R., SASTRA, S. A., PALERMO, C. F., ANDRADE, L. R., SAJJAKULNUKIT, P., ZHANG, L., TOLSTYKA, Z. P., HIRSCHHORN, T., LAMB, C., LIU, T., GU, W., SEELEY, E. S., STONE, E., GEORGIOU, G., MANOR, U., IUGA, A., WAHL, G. M., STOCKWELL, B. R., LYSSIOTIS, C. A. & OLIVE, K. P. 2020. Cysteine depletion induces pancreatic tumor ferroptosis in mice. Science, 368, 85-89.

BAO, X. R., ONG, S. E., GOLDBERGER, O., PENG, J., SHARMA, R., THOMPSON, D. A., VAFAI, S. B., COX, A. G., MARUTANI, E., ICHINOSE, F., GOESSLING, W., REGEV, A., CARR, S. A., CLISH, C. B. & MOOTHA, V. K. 2016. Mitochondrial dysfunction remodels one-carbon metabolism in human cells. Elife, 5.

BERG, M. G., SINGH, L. N., YOUNIS, I., LIU, Q., PINTO, A. M., KAIDA, D., ZHANG, Z., CHO, S., SHERRILL-MIX, S., WAN, L. & DREYFUSS, G. 2012. U1 snRNP determines mRNA length and regulates isoform expression. Cell, 150, 53-64.

BONNET, S., ARCHER, S. L., ALLALUNIS-TURNER, J., HAROMY, A., BEAULIEU, C., THOMPSON, R., LEE, C. T., LOPASCHUK, G. D., PUTTAGUNTA, L., BONNET, S., HARRY, G., HASHIMOTO, K., PORTER, C. J., ANDRADE, M. A., THEBAUD, B. & MICHELAKIS, E. D. 2007. A mitochondria-K+ channel axis is suppressed in cancer and its normalization promotes apoptosis and inhibits cancer growth. Cancer Cell, 11, 37-51.

BRAY, N. L., PIMENTEL, H., MELSTED, P. & PACHTER, L. 2016. Near-optimal probabilistic RNA-seq quantification. Nat Biotechnol, 34, 525-7.

CHRISTOFK, H. R., VANDER HEIDEN, M. G., HARRIS, M. H., RAMANATHAN, A., GERSZTEN, R. E., WEI, R., FLEMING, M. D., SCHREIBER, S. L. & CANTLEY, L. C. 2008. The M2 splice isoform of pyruvate kinase is important for cancer metabolism and tumour growth. Nature, 452, 230-3.

CRABTREE, H. G. 1929. Observations on the carbohydrate metabolism of tumours. Biochem J, 23, 536-45.

DE CONTI, L., BARALLE, M. & BURATTI, E. 2013. Exon and intron definition in pre-mRNA splicing. Wiley Interdiscip Rev RNA, 4, 49-60.

DE FRANCISCO AMORIM, M., WILLING, E. M., SZABO, E. X., FRANCISCO-MANGILET, A. G., DROSTE-BOREL, I, MACEK, B., SCHNEEBERGER, K. & LAUBINGER, S. 2018. The U1 snRNP Subunit LUC7 Modulates Plant Development and Stress Responses via Regulation of Alternative Splicing. Plant Cell, 30, 2838-2854.

DEPHOURE, N., ZHOU, C., VILLEN, J., BEAUSOLEIL, S. A., BAKALARSKI, C. E., ELLEDGE, S. J. & GYGI, S. P. 2008. A quantitative atlas of mitotic phosphorylation. Proc Natl Acad Sci USA, 105, 10762-7.

DOBIN, A., DAVIS, C. A., SCHLESINGER, F., DRENKOW, J., ZALESKI, C., JHA, S., BATUT, P., CHAISSON, M. & GINGERAS, T. R. 2013. STAR: ultrafast universal RNA-seq aligner. Bioinformatics, 29, 15-21.

EDEN, E., NAVON, R., STEINFELD, I., LIPSON, D. & YAKHINI, Z. 2009. GOrilla: a tool for discovery and visualization of enriched GO terms in ranked gene lists. BMC Bioinformatics, 10, 48.

FORTES, P., BILBAO-CORTES, D., FORNEROD, M., RIGAUT, G., RAYMOND, W., SERAPHIN, B. & MATTAJ, I. W. 1999. Luc7p, a novel yeast U1 snRNP protein with a role in 5' splice site recognition. Genes Dev, 13, 2425-38.

FRIEDMAN, B. A., STADLER, M. B., SHOMRON, N., DING, Y. & BURGE, C. B. 2008. Ab initio identification of functionally interacting pairs of cis-regulatory elements. Genome Res, 18, 1643-51.

GAO, G., XIE, A., HUANG, S. C., ZHOU, A., ZHANG, J., HERMAN, A. M., GHASSEMZADEH, S., JEONG, E. M., KASTURIRANGAN, S., RAICU, M., SOBIESKI, M. A., 2ND, BHAT, G., TATOOLES, A., BENZ, E. J., JR., KAMP, T. J. & DUDLEY, S. C., JR. 2011. Role of RBM25/LUC7L3 in abnormal cardiac sodium channel splicing regulation in human heart failure. Circulation, 124, 1124-31.

GAO, J., SCHATTON, D., MARTINELLI, P., HANSEN, H., PLA-MARTIN, D., BARTH, E., BECKER, C., ALTMUELLER, J., FROMMOLT, P., SARDIELLO, M. & RUGARLI, E. I. 2014. CLUH regulates mitochondrial biogenesis by binding mRNAs of nuclear-encoded mitochondrial proteins. J Cell Biol, 207, 213-23.

GEIGER, T., VELIC, A., MACEK, B., LUNDBERG, E., KAMPF, C., NAGARAJ, N., UHLEN, M., COX, J. & MANN, M. 2013. Initial quantitative proteomic map of 28 mouse tissues using the SILAC mouse. Mol Cell Proteomics, 12, 1709-22.

GOHIL, V. M., SHETH, S. A., NILSSON, R., WOJTOVICH, A. P., LEE, J. H., PEROCCHI, F., CHEN, W., CLISH, C. B., AYATA, C., BROOKES, P. S. & MOOTHA, V. K. 2010. Nutrient-sensitized screening for drugs that shift energy metabolism from mitochondrial respiration to glycolysis. Nat Biotechnol, 28, 249-55.

GU, Y., ALBUQUERQUE, C. P., BRAAS, D., ZHANG, W., VILLA, G. R., BI, J., IKEGAMI, S., MASUI, K., GINI, B., YANG, H., GAHMAN, T. C., SHIAU, A. K., CLOUGHESY, T. F., CHRISTOFK, H. R., ZHOU, H., GUAN, K. L. & MISCHEL, P. S. 2017. mTORC2 Regulates Amino Acid Metabolism in Cancer by Phosphorylation of the Cystine-Glutamate Antiporter xCT. Mol Cell, 67, 128-138 e7.

HAYER, A., SHAO, L., CHUNG, M., JOUBERT, L. M., YANG, H. W., TSAI, F. C., BISARIA, A., BETZIG, E. & MEYER, T. 2016. Engulfed cadherin fingers are polarized junctional structures between collectively migrating endothelial cells. Nat Cell Biol, 18, 1311-1323.

HILLENMEYER, M. E., FUNG, E., WILDENHAIN, J., PIERCE, S. E., HOON, S., LEE, W., PROCTOR, M., ST ONGE, R. P., TYERS, M., KOLLER, D., ALTMAN, R. B., DAVIS, R. W., NISLOW, C. & GIAEVER, G. 2008. The chemical genomic portrait of yeast: uncovering a phenotype for all genes. Science, 320, 362-5.

HUANG, L. E., GU, J., SCHAU, M. & BUNN, H. F. 1998. Regulation of hypoxia-inducible factor 1alpha is mediated by an O2-dependent degradation domain via the ubiquitin-proteasome pathway. Proc Natl Acad Sci USA, 95, 7987-92.

HUTTLIN, E. L., JEDRYCHOWSKI, M. P., ELIAS, J. E., GOSWAMI, T., RAD, R., BEAUSOLEIL, S. A., VILLEN, J., HAAS, W., SOWA, M. E. & GYGI, S. P. 2010. A tissue-specific atlas of mouse protein phosphorylation and expression. Cell, 143, 1174-89.

ITO, K. & SUDA, T. 2014. Metabolic requirements for the maintenance of self-renewing stem cells. Nat Rev Mol Cell Biol, 15, 243-56.

JIANG, L., KON, N., LI, T., WANG, S. J., SU, T., HIBSHOOSH, H., BAER, R. & GU, W. 2015. Ferroptosis as a p53-mediated activity during tumour suppression. Nature, 520, 57-62.

JOURDAIN, A. A., KOPPEN, M., WYDRO, M., RODLEY, C. D., LIGHTOWLERS, R. N., CHRZANOWSKA-LIGHTOWLERS, Z. M. & MARTINOU, J. C. 2013. GRSF1 regulates RNA processing in mitochondrial RNA granules. Cell Metab, 17, 399-410.

KIMURA, E., HIDAKA, K., KIDA, Y., MORISAKI, H., SHIRAI, M., ARAKI, K., SUZUKI, M., YAMAMURA, K. I. & MORISAKI, T. 2004. Serine-arginine-rich nuclear protein Luc7l regulates myogenesis in mice. Gene, 341, 41-7.

KOPPULA, P., ZHANG, Y., SHI, J., LI, W. & GAN, B. 2017. The glutamate/cystine antiporter SLC7A11/xCT enhances cancer cell dependency on glucose by exporting glutamate. J Biol Chem, 292, 14240-14249.

KOTINI, A. G., CHANG, C. J., BOUSSAAD, I., DELROW, J. J., DOLEZAL, E. K., NAGULAPALLY, A. B., PERNA, F., FISHBEIN, G. A., KLIMEK, V. M., HAWKINS, R. D., HUANGFU, D., MURRY, C. E., GRAUBERT, T., NIMER, S. D. & PAPAPETROU, E. P. 2015. Functional analysis of a chromosomal deletion associated with myelodysplastic syndromes using isogenic human induced pluripotent stem cells. Nat Biotechnol, 33, 646-55.

LI, W., XU, H., XIAO, T., CONG, L., LOVE, M. I., ZHANG, F., IRIZARRY, R. A., LIU, J. S., BROWN, M. & LIU, X. S. 2014. MAGeCK enables robust identification of essential genes from genome-scale CRISPR/Cas9 knockout screens. Genome Biol, 15, 554.

LI, X., LIU, S., JIANG, J., ZHANG, L., ESPINOSA, S., HILL, R. C., HANSEN, K. C., ZHOU, Z. H. & ZHAO, R. 2017. CryoEM structure of Saccharomyces cerevisiae U1 snRNP offers insight into alternative splicing. Nat Commun, 8, 1035.

LOVCI, M. T., GHANEM, D., MARR, H., ARNOLD, J., GEE, S., PARRA, M., LIANG, T. Y., STARK, T. J., GERMAN, L. T., HOON, S., MASSIRER, K. B., PRATT, G. A., BLACK, D. L., GRAY, J. W., CONBOY, J. G. & YEO, G. W. 2013. Rbfox proteins regulate alternative mRNA splicing through evolutionarily conserved RNA bridges. Nat Struct Mol Biol, 20, 1434-42.

LOVE, M. I., HUBER, W. & ANDERS, S. 2014. Moderated estimation of fold change and dispersion for RNA-seq data with DESeq2. Genome Biol, 15, 550.

MAKAROV, E. M., OWEN, N., BOTTRILL, A. & MAKAROVA, O. V. 2012. Functional mammalian spliceosomal complex E contains SMN complex proteins in addition to U1 and U2 snRNPs. Nucleic Acids Res, 40, 2639-52.

OH, J. M., VENTERS, C. C., DI, C., PINTO, A. M., WAN, L., YOUNIS, I., CAI, Z., ARAI, C., SO, B. R., DUAN, J. & DREYFUSS, G. 2020. U1 snRNP regulates cancer cell migration and invasion in vitro. Nat Commun, 11, 1.

PASTEUR, L. 1861. Animalcules infusoires vivant sans gaz oxygene libre et determinant des fermentations. Comptes rendus—Académie des sciences, 52, 344-347.

PEARCE, E. L., POFFENBERGER, M. C., CHANG, C. H. & JONES, R. G. 2013. Fueling immunity: insights into metabolism and lymphocyte function. Science, 342, 1242454.

PEREZ-RIVEROL, Y., CSORDAS, A., BAI, J., BERNAL-LLINARES, M., HEWAPATHIRANA, S., KUNDU, D. J., INUGANTI, A., GRISS, J., MAYER, G., EISENACHER, M., PEREZ, E., USZKOREIT, J., PFEUFFER, J., SACHSENBERG, T., YILMAZ, S., TIWARY, S., COX, J., AUDAIN, E., WALZER, M., JARNUCZAK, A. F., TERNENT, T., BRAZMA, A. & VIZCAINO, J. A. 2019. The PRIDE database and related tools and resources in 2019: improving support for quantification data. Nucleic Acids Res, 47, D442-D450.

PFEIFFER, T., SCHUSTER, S. & BONHOEFFER, S. 2001. Cooperation and competition in the evolution of ATP-producing pathways. Science, 292, 504-7.

PING, L., DUONG, D. M., YIN, L., GEARING, M., LAH, J. J., LEVEY, A. I. & SEYFRIED, N. T. 2018. Global quantitative analysis of the human brain proteome in Alzheimer's and Parkinson's Disease. Sci Data, 5, 180036.

PLASCHKA, C., LIN, P. C., CHARENTON, C. & NAGAI, K. 2018. Prespliceosome structure provides insights into spliceosome assembly and regulation. Nature, 559, 419-422.

PUIGSERVER, P., WU, Z., PARK, C. W., GRAVES, R., WRIGHT, M. & SPIEGELMAN, B. M. 1998. A cold-inducible coactivator of nuclear receptors linked to adaptive thermogenesis. Cell, 92, 829-39.

REITZER, L. J., WICE, B. M. & KENNELL, D. 1979. Evidence that glutamine, not sugar, is the major energy source for cultured HeLa cells. J Biol Chem, 254, 2669-76.

RINO, J., CARVALHO, T., BRAGA, J., DESTERRO, J. M., LUHRMANN, R. & CARMO-FONSECA, M. 2007. A stochastic view of spliceosome assembly and recycling in the nucleus. PLoS Comput Biol, 3, 2019-31.

ROBINSON, B. H., PETROVA-BENEDICT, R., BUNCIC, J. R. & WALLACE, D. C. 1992. Nonviability of cells with oxidative defects in galactose medium: a screening test for affected patient fibroblasts. Biochem Med Metab Biol, 48, 122-6.

ROSSIGNOL, R., GILKERSON, R., AGGELER, R., YAMAGATA, K., REMINGTON, S. J. & CAPALDI, R. A. 2004. Energy substrate modulates mitochondrial structure and oxidative capacity in cancer cells. Cancer Res, 64, 985-93.

SATO, H., NOMURA, S., MAEBARA, K., SATO, K., TAMBA, M. & BANNAI, S. 2004. Transcriptional control of cystine/glutamate transporter gene by amino acid deprivation. Biochem Biophys Res Commun, 325, 109-16.

SATO, H., TAMBA, M., ISHII, T. & BANNAI, S. 1999. Cloning and expression of a plasma membrane cystine/glutamate exchange transporter composed of two distinct proteins. J Biol Chem, 274, 11455-8.

SHEN, S., PARK, J. W., LU, Z. X., LIN, L., HENRY, M. D., WU, Y. N., ZHOU, Q. & XING, Y. 2014. rMATS: robust and flexible detection of differential alternative splicing from replicate RNA-Seq data. Proc Natl Acad Sci USA, 111, E5593-601.

SHIN, C. S., MISHRA, P., WATROUS, J. D., CARELLI, V., D'AURELIO, M., JAIN, M. & CHAN, D. C. 2017. The glutamate/cystine xCT antiporter antagonizes glutamine metabolism and reduces nutrient flexibility. Nat Commun, 8, 15074.

SHUAI, S., SUZUKI, H., DIAZ-NAVARRO, A., NADEU, F., KUMAR, S. A., GUTIERREZ-FERNANDEZ, A., DELGADO, J., PINYOL, M., LOPEZ-OTIN, C., PUENTE, X. S., TAYLOR, M. D., CAMPO, E. & STEIN,

L. D. 2019. The U1 spliceosomal RNA is recurrently mutated in multiple cancers. Nature, 574, 712-716.

SINGH, H., LANE, A. A., CORRELL, M., PRZYCHODZEN, B., SYKES, D. B., STONE, R. M., BALLEN, K. K., AMREIN, P. C., MACIEJEWSKI, J. & ATTAR, E. C. 2013. Putative RNA-splicing gene LUC7L2 on 7q34 represents a candidate gene in pathogenesis of myeloid malignancies. Blood Cancer J, 3, e17.

SPELLMAN, R., LLORIAN, M. & SMITH, C. W. 2007. Crossregulation and functional redundancy between the splicing regulator PTB and its paralogs nPTB and ROD1. Mol Cell, 27, 420-34.

SUZUKI, H., KUMAR, S. A., SHUAI, S., DIAZ-NAVARRO, A., GUTIERREZ-FERNANDEZ, A., DE ANTONELLIS, P., CAVALLI, F. M. G., JURASCHKA, K., FAROOQ, H., SHIBAHARA, I., VLADOIU, M. C., ZHANG, J., ABEYSUNDARA, N., PRZELICKI, D., SKOWRON, P., GAUER, N., LUU, B., DANIELS, C., WU, X., FORGET, A., MOMIN, A., WANG, J., DONG, W., KIM, S. K., GRAJKOWSKA, W. A., JOUVET, A., FEVRE-MONTANGE, M., GARRE, M. L., RAO, A. A. N., GIANNINI, C., KROS, J. M., FRENCH, P. J., JABADO, N., NG, H. K., POON, W. S., EBERHART, C. G., POLLACK, I. F., OLSON, J. M., WEISS, W. A., KUMABE, T., LOPEZ-AGUILAR, E., LACH, B., MASSIMINO, M., VAN MEIR, E. G., RUBIN, J. B., VIBHAKAR, R., CHAMBLESS, L. B., KIJIMA, N., KLEKNER, A., BOGNAR, L., CHAN, J. A., FARIA, C. C., RAGOUSSIS, J., PFISTER, S. M., GOLDENBERG, A., WECHSLER-REYA, R. J., BAILEY, S. D., GARZIA, L., MORRISSY, A. S., MARRA, M. A., HUANG, X., MALKIN, D., AYRAULT, O., RAMASWAMY, V., PUENTE, X. S., CALARCO, J. A., STEIN, L. & TAYLOR, M. D. 2019. Recurrent non-coding U1-snRNA mutations drive cryptic splicing in Shh medulloblastoma. Nature.

TARUI, S., OKUNO, G., IKURA, Y., TANAKA, T., SUDA, M. & NISHIKAWA, M. 1965. Phosphofructokinase Deficiency in Skeletal Muscle. A New Type of Glycogenosis. Biochem Biophys Res Commun, 19, 517-23.

TO, T. L., CUADROS, A. M., SHAH, H., HUNG, W. H. W., LI, Y., KIM, S. H., RUBIN, D. H. F., BOE, R. H., RATH, S., EATON, J. K., PICCIONI, F., GOODALE, A., KALANI, Z., DOENCH, J. G., ROOT, D. E., SCHREIBER, S. L., VAFAI, S. B. & MOOTHA, V. K. 2019. A Compendium of Genetic Modifiers of Mitochondrial Dysfunction Reveals Intra-organelle Buffering. Cell, 179, 1222-1238 e17.

TUFARELLI, C., FRISCHAUF, A. M., HARDISON, R., FLINT, J. & HIGGS, D. R. 2001. Characterization of a widely expressed gene (LUC7-LIKE; LUC7L) defining the centromeric boundary of the human alpha-globin domain. Genomics, 71, 307-14.

TYYNISMAA, H., CARROLL, C. J., RAIMUNDO, N., AHOLA-ERKKILA, S., WENZ, T., RUHANEN, H., GUSE, K., HEMMINKI, A., PELTOLA-MJOSUND, K. E., TULKKI, V., ORESIC, M., MORAES, C. T., PIETILAINEN, K., HOVATTA, I. & SUOMALAINEN, A. 2010. Mitochondrial myopathy induces a starvation-like response. Hum Mol Genet, 19, 3948-58.

UBAIDA-MOHIEN, C., LYASHKOV, A., GONZALEZ-FREIRE, M., THARAKAN, R., SHARDELL, M., MOADDEL, R., SEMBA, R. D., CHIA, C. W., GOROSPE, M., SEN, R. & FERRUCCI, L. 2019. Discovery proteomics in aging human skeletal muscle finds change in spliceosome, immunity, proteostasis and mitochondria. Elife, 8.

VAN NOSTRAND, E. L., NGUYEN, T. B., GELBOIN-BURKHART, C., WANG, R., BLUE, S. M., PRATT, G. A., LOUIE, A. L. & YEO, G. W. 2017. Robust, Cost-Effective Profiling of RNA Binding Protein Targets with Single-end Enhanced Crosslinking and Immunoprecipitation (seCLIP). Methods Mol Biol, 1648, 177-200.

VAN NOSTRAND, E. L., PRATT, G. A., SHISHKIN, A. A., GELBOIN-BURKHART, C., FANG, M. Y., SUNDARARAMAN, B., BLUE, S. M., NGUYEN, T. B., SURKA, C., ELKINS, K., STANTON, R., RIGO, F., GUTTMAN, M. & YEO, G. W. 2016. Robust transcriptome-wide discovery of RNA-binding protein binding sites with enhanced CLIP (eCLIP). Nat Methods, 13, 508-14.

VANDERSLUIS, B., HESS, D. C., PESYNA, C., KRUMHOLZ, E. W., SYED, T., SZAPPANOS, B., NISLOW, C., PAPP, B., TROYANSKAYA, O. G., MYERS, C. L. & CAUDY, A. A. 2014. Broad metabolic sensitivity profiling of a prototrophic yeast deletion collection. Genome Biol, 15, R64.

VISANJI, N. P., WISLET-GENDEBIEN, S., OSCHIPOK, L. W., ZHANG, G., AUBERT, I., FRASER, P. E. & TANDON, A. 2011. Effect of Ser-129 phosphorylation on interaction of alpha-synuclein with synaptic and cellular membranes. J Biol Chem, 286, 35863-73.

VIVES-CORRONS, J. L., KORALKOVA, P., GRAU, J. M., MANU PEREIRA MDEL, M. & VAN WIJK, R. 2013. First description of phosphofructokinase deficiency in spain: identification of a novel homozygous missense mutation in the PFKM gene. Front Physiol, 4, 393.

WARBURG, O. 1924. Über den Stoffwechsel der Carcinomzelle. Naturwissenschaften, 12, 1131-1137.

WEBBY, C. J., WOLF, A., GROMAK, N., DREGER, M., KRAMER, H., KESSLER, B., NIELSEN, M. L., SCHMITZ, C., BUTLER, D. S., YATES, J. R., 3RD, DELAHUNTY, C. M., HAHN, P., LENGELING, A., MANN, M., PROUDFOOT, N. J., SCHOFIELD, C. J. & BOTTGER, A. 2009. Jmjd6 catalyses lysyl-hydroxylation of U2AF65, a protein associated with RNA splicing. Science, 325, 90-3.

YIN, Y., LU, J. Y., ZHANG, X., SHAO, W., XU, Y., LI, P., HONG, Y., CUI, L., SHAN, G., TIAN, B., ZHANG, Q. C. & SHEN, X. 2020. U1 snRNP regulates chromatin retention of noncoding RNAs. Nature, 580, 147-150.

ZHANG, J., LIEU, Y. K., ALI, A. M., PENSON, A., REGGIO, K. S., RABADAN, R., RAZA, A., MUKHERJEE, S. & MANLEY, J. L. 2015. Disease-associated mutation in SRSF2 misregulates splicing by altering RNA-binding affinities. Proc Natl Acad Sci USA, 112, E4726-34.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the disclosure claimed. Thus, it should be understood that although the present disclosure has been specifically disclosed by preferred embodiments and optional features, modification and variation of the disclosure embodied therein herein disclosed may be resorted to by those skilled in the art, and that such modifications and variations are considered to be within the scope of this disclosure.

The disclosure has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein. The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the present technology. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

One skilled in the art readily appreciates that the present disclosure is well adapted to carry out the objects and obtain the ends and advantages mentioned, as well as those inherent therein. Modifications therein and other uses will occur to those skilled in the art. These modifications are encompassed within the spirit of the disclosure and are defined by the scope of the claims, which set forth non-limiting embodiments of the disclosure.

In addition, where features or aspects of the disclosure are described in terms of Markush groups, those skilled in the art will recognize that the disclosure is also thereby described in terms of any individual member or subgroup of members of the Markush group.

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

What is claimed:

1. A method for inducing exon skipping in a cell during splicing of human SLC7A11 pre-mRNA to form SLC7A11 mRNA lacking exon 7, the method comprising contacting the SLC7A11 pre-mRNA comprising exons 1-12 in the cell with an antisense oligonucleotide, wherein the antisense oligonucleotide comprises the nucleotide sequence set forth in any of SEQ ID NO:1-11.

2. The method according to claim 1, wherein the antisense oligonucleotide binds the pre-mRNA at a region comprising at least the 3' terminal nucleotide of exon 7 and at least the 5' terminal nucleotide of the flanking intron.

3. A method for inducing exon skipping in a cell during splicing of human SLC7A11 pre-mRNA to form SLC7A11 mRNA lacking exon 9, the method comprising contacting the SLC7A11 pre-mRNA comprising exons 1-12 in the cell with an antisense oligonucleotide, wherein the antisense oligonucleotide comprises the nucleotide sequence set forth in any of SEQ ID NO:12-22.

4. The method according to claim 3, wherein the antisense oligonucleotide binds the pre-mRNA at a region comprising at least the 3' terminal nucleotide of exon 9 and at least the 5' terminal nucleotide of the flanking intron.

5. A method for inducing exon skipping in a cell during splicing of human SLC7A11 pre-mRNA to form SLC7A11 mRNA lacking exons 7 and 9, the method comprising contacting the SLC7A11 pre-mRNA comprising exons 1-12 in the cell with:
(a) a first antisense oligonucleotide comprising the nucleotide sequence set forth in any of SEQ ID NO:1-11, and
(b) a second antisense oligonucleotide comprising the nucleotide sequence set forth in any of SEQ ID NO:12-22.

6. The method according to claim 5, wherein the mRNA is subjected to nonsense-mediated decay.

7. The method according to claim 5, wherein the mRNA is translated to a protein deficient for cystine/glutamate antiporter activity, as compared to a protein translated from the mRNA comprising exons 1-12.

8. The method according to any one of claim 5, wherein the method is carried out in vitro.

9. The method according to any one of claim 5, wherein the method is carried out in vivo.

10. The method of claim 1, wherein the antisense oligonucleotide sequence comprises the nucleotide sequence set forth in SEQ ID NO: 1.

11. The method of claim 10, wherein the antisense oligonucleotide comprises the nucleotide sequence set forth in SEQ ID NO: 12.

12. The method of claim 5, wherein the first antisense oligonucleotide comprises the nucleotide sequence set forth in SEQ ID NO: 1, and wherein the second antisense oligonucleotide comprises the nucleotide sequence set forth in SEQ ID NO: 12.

\* \* \* \* \*

SEQUENCE LISTING

```
<160> NUMBER OF SEQ ID NOS: 38

<210> SEQ ID NO 1
<211> LENGTH: 25
<212> TYPE: DNA
<213> ORGANISM: Artificial Sequence
<220> FEATURE:
<223> OTHER INFORMATION: Exon 7 antisense oligo SLC7A11 exon7_55

<400> SEQUENCE: 1
ccaacttgga cttaccactg ccact                                         25

<210> SEQ ID NO 2
<211> LENGTH: 40
<212> TYPE: DNA
<213> ORGANISM: Artificial Sequence
<220> FEATURE:
<223> OTHER INFORMATION: Exon 7 antisense oligo

<400> SEQUENCE: 2
attttgggaa cttggactta ccactgccac tgccactgcc                         40

<210> SEQ ID NO 3
<211> LENGTH: 25
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 3
acttaccact gccactgcca ctgcc                                         25

<210> SEQ ID NO 4
<211> LENGTH: 27
<212> TYPE: DNA
<213> ORGANISM: Artificial Sequence
<220> FEATURE:
<223> OTHER INFORMATION: Exon 7 antisense oligo (subsequence of SEQ ID
      NO:2)
```

<400> SEQUENCE: 4
attttgggaa cttggactta ccactgc                                              27

<210> SEQ ID NO 5
<211> LENGTH: 21
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 5
accactgcca ctgccactgc c                                                    21

<210> SEQ ID NO 6
<211> LENGTH: 10
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 6
cactgccact                                                                 10

<210> SEQ ID NO 7
<211> LENGTH: 11
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 7
ccactgccac t                                                               11

<210> SEQ ID NO 8
<211> LENGTH: 16
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 8
tggacttacc actgcc                                                          16

<210> SEQ ID NO 9
<211> LENGTH: 24
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 9
ggaacttgga cttaccactg ccac                                                 24

<210> SEQ ID NO 10
<211> LENGTH: 26
<212> TYPE: DNA
<213> ORGANISM: Artificial Sequence
<220> FEATURE:
<223> OTHER INFORMATION: Exon 7 antisense oligo (subsequence of SEQ ID
      NO:2)

```
<400> SEQUENCE: 10
attttgggaa cttggactta ccactg                                           26

<210> SEQ ID NO 11
<211> LENGTH: 19
<212> TYPE: DNA
<213> ORGANISM: Artificial Sequence
<220> FEATURE:
<223> OTHER INFORMATION: Exon 7 antisense oligo (subsequence of SEQ ID
      NO:2)

<400> SEQUENCE: 11
gaacttggac ttaccactg                                                   19

<210> SEQ ID NO 12
<211> LENGTH: 25
<212> TYPE: DNA
<213> ORGANISM: Artificial Sequence
<220> FEATURE:
<223> OTHER INFORMATION: Exon 9 antisense oligo SLC7A11 exon9_55

<400> SEQUENCE: 12
atatacttgt taatatgcat tacca                                            25

<210> SEQ ID NO 13
<211> LENGTH: 35
<212> TYPE: DNA
<213> ORGANISM: Artificial Sequence
<220> FEATURE:
<223> OTHER INFORMATION: Exon 9 antisense oligo

<400> SEQUENCE: 13
atatacttgt taatatgcat taccaaaaca ataac                                 35

<210> SEQ ID NO 14
<211> LENGTH: 10
<212> TYPE: DNA
<213> ORGANISM: Artificial Sequence
<220> FEATURE:
<223> OTHER INFORMATION: Exon 9 antisense oligo (subsequence of SEQ ID
      NO:13)

<400> SEQUENCE: 14
atgcattacc                                                             10

<210> SEQ ID NO 15
<211> LENGTH: 10
<212> TYPE: DNA
<213> ORGANISM: Artificial Sequence
<220> FEATURE:
<223> OTHER INFORMATION: Exon 9 antisense oligo (subsequence of SEQ ID
      NO:13)

<400> SEQUENCE: 15
gcattaccaa                                                             10

<210> SEQ ID NO 16
<211> LENGTH: 15
<212> TYPE: DNA
<213> ORGANISM: Artificial Sequence
<220> FEATURE:
<223> OTHER INFORMATION: Exon 9 antisense oligo (subsequence of SEQ ID
      NO:13)

<400> SEQUENCE: 16
taatatgcat tacca                                                       15
```

<210> SEQ ID NO 17
<211> LENGTH: 18
<212> TYPE: DNA
<213> ORGANISM: Artificial Sequence
<220> FEATURE:
<223> OTHER INFORMATION: Exon 9 antisense oligo (subsequence of SEQ ID
    NO:13)

<400> SEQUENCE: 17
cttgttaata tgcattac                                             18

<210> SEQ ID NO 18
<211> LENGTH: 24
<212> TYPE: DNA
<213> ORGANISM: Artificial Sequence
<220> FEATURE:
<223> OTHER INFORMATION: Exon 9 antisense oligo (subsequence of SEQ ID
    NO:13)

<400> SEQUENCE: 18
cttgttaata tgcattacca aaac                                      24

<210> SEQ ID NO 19
<211> LENGTH: 21
<212> TYPE: DNA
<213> ORGANISM: Artificial Sequence
<220> FEATURE:
<223> OTHER INFORMATION: Exon 9 antisense oligo (subsequence of SEQ ID
    NO:13)

<400> SEQUENCE: 19
gttaatatgc attaccaaaa c                                         21

<210> SEQ ID NO 20
<211> LENGTH: 15
<212> TYPE: DNA
<213> ORGANISM: Artificial Sequence
<220> FEATURE:
<223> OTHER INFORMATION: Exon 9 antisense oligo (subsequence of SEQ ID
    NO:13)

<400> SEQUENCE: 20
aatatgcatt accaa                                                15

<210> SEQ ID NO 21
<211> LENGTH: 13
<212> TYPE: DNA
<213> ORGANISM: Artificial Sequence
<220> FEATURE:
<223> OTHER INFORMATION: Exon 9 antisense oligo (subsequence of SEQ ID
    NO:13

<400> SEQUENCE: 21
gcattaccaa aac                                                  13

<210> SEQ ID NO 22
<211> LENGTH: 15
<212> TYPE: DNA
<213> ORGANISM: Artificial Sequence
<220> FEATURE:
<223> OTHER INFORMATION: Exon 9 antisense oligo (subsequence of SEQ ID
    NO:13)

<400> SEQUENCE: 22
taccaaaaca ataac                                                15

```
<210> SEQ ID NO 23
<211> LENGTH: 60
<212> TYPE: DNA
<213> ORGANISM: Homo sapiens

<400> SEQUENCE: 23
aaccattccc cttgcaatat gtatatccat ggccattgtc accattggct atgtgctgac      60

<210> SEQ ID NO 24
<211> LENGTH: 25
<212> TYPE: DNA
<213> ORGANISM: Homo sapiens

<400> SEQUENCE: 24
gtaagtccaa gttgggaaaa tgcca                                           25

<210> SEQ ID NO 25
<211> LENGTH: 97
<212> TYPE: DNA
<213> ORGANISM: Homo sapiens

<400> SEQUENCE: 25
gttattctat gttgcgtctc gagagggtca ccttccagaa atcctctcca tgattcatgt      60
ccgcaagcac actcctctac cagctgttat tgttttg                              97

<210> SEQ ID NO 26
<211> LENGTH: 25
<212> TYPE: DNA
<213> ORGANISM: Homo sapiens

<400> SEQUENCE: 26
gtaatgcata ttaacaagta tatct                                           25

<210> SEQ ID NO 27
<211> LENGTH: 85
<212> TYPE: DNA
<213> ORGANISM: Homo sapiens

<400> SEQUENCE: 27
aaccattccc cttgcaatat gtatatccat ggccattgtc accattggct atgtgctgac      60
gtaagtccaa gttgggaaaa tgcca                                           85

<210> SEQ ID NO 28
<211> LENGTH: 121
<212> TYPE: DNA
<213> ORGANISM: Homo sapiens

<400> SEQUENCE: 28
gttattctat gttgcgtctc gagagggtca ccttccagaa atcctctcca tgattcatgt      60
ccgcaagcac actcctctac cagctgttat tgttttggta atgcatatta acaagtaatc    120
t                                                                    121

<210> SEQ ID NO 29
<211> LENGTH: 1506
<212> TYPE: DNA
<213> ORGANISM: Homo sapiens

<400> SEQUENCE: 29
atggtcagaa agcctgttgt gtccaccatc tccaaaggag gttacctgca gggaaatgtt      60
aacgggaggc tgccttccct gggcaacaag gagccacctg ggcaggagaa agtgcagctg    120
```

```
aagaggaaag tcactttact gaggggagtc tccattatca ttggcaccat cattggagca    180
ggaatcttca tctctcctaa gggcgtgctc cagaacacgg gcagcgtggg catgtctctg    240
accatctgga cggtgtgtgg ggtcctgtca ctatttggag ctttgtctta tgctgaattg    300
ggaacaacta taaagaaatc tggaggtcat tacacatata ttttggaagt ctttggtcca    360
ttaccagctt ttgtacgagt ctgggtggaa ctcctcataa tacgccctgc agctactgct    420
gtgatatccc tggcatttgg acgctacatt ctggaaccat tttttattca atgtgaaatc    480
cctgaacttg cgatcaagct cattacagct gtgggcataa ctgtagtgat ggtcctaaat    540
agcatgagtg tcagctggag cgcccggatc cagattttct taaccttttg caagctcaca    600
gcaattctga taattatagt ccctggagtt atgcagctaa ttaaaggtca aacgcagaac    660
tttaaagacg cctttttcagg aagagattca agtattacgc ggttgccact ggcttttta t    720
tatggaatgt atgcatatgc tggctggttt tacctcaact ttgttactga agaagtagaa    780
aaccctgaaa aaaccattcc ccttgcaata tgtatatcca tggccattgt caccattggc    840
tatgtgctga caaatgtggc ctactttacg accattaatg ctgaggagct gctgctttca    900
aatgcagtgg cagtgacctt ttctgagcgg ctactgggaa atttctcatt agcagttccg    960
atctttgttg ccctctcctg ctttggctcc atgaacggtg gtgtgtttgc tgtctccagg   1020
ttattctatg ttgcgtctcg agagggtcac cttccagaaa tcctctccat gattcatgtc   1080
cgcaagcaca ctcctctacc agctgttatt gttttgcacc ctttgacaat gataatgctc   1140
ttctctggag acctcgacag tcttttgaat ttcctcagtt ttgccaggtg gcttttta tt   1200
gggctggcag ttgctgggct gatttatctt cgatacaaat gcccagatat gcatcgtcct   1260
ttcaaggtgc cactgttcat cccagctttg ttttccttca catgcctctt catggttgcc   1320
ctttccctct attcggaccc atttagtaca gggattggct tcgtcatcac tctgactgga   1380
gtccctgcgt attatctctt tattatatgg gacaagaaac ccaggtggtt tagaataatg   1440
tcagagaaaa taaccagaac attacaaata atactggaag ttgtaccaga agaagataag   1500
ttatga                                                               1506
```

<210> SEQ ID NO 30
<211> LENGTH: 501
<212> TYPE: PRT
<213> ORGANISM: Homo sapiens

<400> SEQUENCE: 30

```
Met Val Arg Lys Pro Val Val Ser Thr Ile Ser Lys Gly Gly Tyr Leu
1               5                   10                  15

Gln Gly Asn Val Asn Gly Arg Leu Pro Ser Leu Gly Asn Lys Glu Pro
            20                  25                  30

Pro Gly Gln Glu Lys Val Gln Leu Lys Arg Lys Val Thr Leu Leu Arg
        35                  40                  45

Gly Val Ser Ile Ile Ile Gly Thr Ile Ile Gly Ala Gly Ile Phe Ile
    50                  55                  60

Ser Pro Lys Gly Val Leu Gln Asn Thr Gly Ser Val Gly Met Ser Leu
65                  70                  75                  80

Thr Ile Trp Thr Val Cys Gly Val Leu Ser Leu Phe Gly Ala Leu Ser
                85                  90                  95

Tyr Ala Glu Leu Gly Thr Thr Ile Lys Lys Ser Gly Gly His Tyr Thr
            100                 105                 110

Tyr Ile Leu Glu Val Phe Gly Pro Leu Pro Ala Phe Val Arg Val Trp
```

```
            115                 120                 125
Val Glu Leu Leu Ile Ile Arg Pro Ala Thr Ala Val Ile Ser Leu
    130                 135                 140

Ala Phe Gly Arg Tyr Ile Leu Glu Pro Phe Phe Ile Gln Cys Glu Ile
145                 150                 155                 160

Pro Glu Leu Ala Ile Lys Leu Ile Thr Ala Val Gly Ile Thr Val Val
                    165                 170                 175

Met Val Leu Asn Ser Met Ser Val Ser Trp Ser Ala Arg Ile Gln Ile
                180                 185                 190

Phe Leu Thr Phe Cys Lys Leu Thr Ala Ile Leu Ile Ile Val Pro
    195                 200                 205

Gly Val Met Gln Leu Ile Lys Gly Gln Thr Gln Asn Phe Lys Asp Ala
    210                 215                 220

Phe Ser Gly Arg Asp Ser Ser Ile Thr Arg Leu Pro Leu Ala Phe Tyr
225                 230                 235                 240

Tyr Gly Met Tyr Ala Tyr Ala Gly Trp Phe Tyr Leu Asn Phe Val Thr
                    245                 250                 255

Glu Glu Val Glu Asn Pro Glu Lys Thr Ile Pro Leu Ala Ile Cys Ile
                260                 265                 270

Ser Met Ala Ile Val Thr Ile Gly Tyr Val Leu Thr Asn Val Ala Tyr
    275                 280                 285

Phe Thr Thr Ile Asn Ala Glu Glu Leu Leu Leu Ser Asn Ala Val Ala
    290                 295                 300

Val Thr Phe Ser Glu Arg Leu Leu Gly Asn Phe Ser Leu Ala Val Pro
305                 310                 315                 320

Ile Phe Val Ala Leu Ser Cys Phe Gly Ser Met Asn Gly Gly Val Phe
                    325                 330                 335

Ala Val Ser Arg Leu Phe Tyr Val Ala Ser Arg Glu Gly His Leu Pro
                340                 345                 350

Glu Ile Leu Ser Met Ile His Val Arg Lys His Thr Pro Leu Pro Ala
    355                 360                 365

Val Ile Val Leu His Pro Leu Thr Met Ile Met Leu Phe Ser Gly Asp
    370                 375                 380

Leu Asp Ser Leu Leu Asn Phe Leu Ser Phe Ala Arg Trp Leu Phe Ile
385                 390                 395                 400

Gly Leu Ala Val Ala Gly Leu Ile Tyr Leu Arg Tyr Lys Cys Pro Asp
                    405                 410                 415

Met His Arg Pro Phe Lys Val Pro Leu Phe Ile Pro Ala Leu Phe Ser
                420                 425                 430

Phe Thr Cys Leu Phe Met Val Ala Leu Ser Leu Tyr Ser Asp Pro Phe
    435                 440                 445

Ser Thr Gly Ile Gly Phe Val Ile Thr Leu Thr Gly Val Pro Ala Tyr
    450                 455                 460

Tyr Leu Phe Ile Ile Trp Asp Lys Lys Pro Arg Trp Phe Arg Ile Met
465                 470                 475                 480

Ser Glu Lys Ile Thr Arg Thr Leu Gln Ile Ile Leu Glu Val Val Pro
                485                 490                 495

Glu Glu Asp Lys Leu
                500

<210> SEQ ID NO 31
<211> LENGTH: 1387
<212> TYPE: DNA
<213> ORGANISM: Homo sapiens
```

<400> SEQUENCE: 31

```
atggtcagaa agcctgttgt gtccaccatc tccaaaggag gttacctgca gggaaatgtt        60
aacgggaggc tgccttccct gggcaacaag gagccacctg ggcaggagaa agtgcagctg       120
aagaggaaag tcactttact gaggggagtc tccattatca ttggcaccat cattggagca       180
ggaatcttca tctctcctaa gggcgtgctc cagaacacgg gcagcgtggg catgtctctg       240
accatctgga cggtgtgtgg ggtcctgtca ctatttggag ctttgtctta tgctgaattg       300
ggaacaacta taaagaaatc tggaggtcat tacacatata ttttggaagt ctttggtcca       360
ttaccagctt ttgtacgagt ctgggtggaa ctcctcataa tacgccctgc agctactgct       420
gtgatatccc tggcatttgg acgctacatt ctggaaccat ttttattca atgtgaaatc       480
cctgaacttg cgatcaagct cattacagct gtgggcataa ctgtagtgat ggtcctaaat       540
agcatgagtg tcagctggag cgcccggatc cagatttct taaccttttg caagctcaca       600
gcaattctga taattatagt ccctggagtt atgcagctaa ttaaaggtca aacgcagaac       660
tttaaagacg ccttttcagg aagagattca agtattacgc ggttgccact ggctttttat       720
tatggaatgt atgcatatgc tggctggttt tacctcaact tgttactga agaagtagaa       780
aaccctgaaa acagtgacct tttctgagcg gctactggga aatttctcat tagcagttcc       840
gatctttgtt gccctctcct gctttggctc catgaacggt ggtgtgtttg ctgtctccag       900
gttattctat gttgcgtctc gagagggtca ccttccagaa atcctctcca tgattcatgt       960
ccgcaagcac actcctctac cagctgttat tgttttgcac cctttgacaa tgataatgct      1020
cttctctgga gacctcgaca gtcttttgaa tttcctcagt tttgccaggt ggcttttat      1080
tgggctggca gttgctgggc tgatttatct tcgatacaaa tgcccagata tgcatcgtcc      1140
tttcaaggtg ccactgttca tcccagcttt gttttccttc acatgcctct tcatggttgc      1200
cctttccctc tattcggacc catttagtac agggattggc ttcgtcatca ctctgactgg      1260
agtccctgcg tattatctct ttattatatg ggacaagaaa cccaggtggt ttagaataat      1320
gtcagagaaa ataaccagaa cattacaaat aatactggaa gttgtaccag aagaagataa      1380
gttatga                                                                1387
```

<210> SEQ ID NO 32
<211> LENGTH: 1281
<212> TYPE: DNA
<213> ORGANISM: Homo sapiens

<400> SEQUENCE: 32

```
atggtcagaa agcctgttgt gtccaccatc tccaaaggag gttacctgca gggaaatgtt        60
aacgggaggc tgccttccct gggcaacaag gagccacctg ggcaggagaa agtgcagctg       120
aagaggaaag tcactttact gaggggagtc tccattatca ttggcaccat cattggagca       180
ggaatcttca tctctcctaa gggcgtgctc cagaacacgg gcagcgtggg catgtctctg       240
accatctgga cggtgtgtgg ggtcctgtca ctatttggag ctttgtctta tgctgaattg       300
ggaacaacta taaagaaatc tggaggtcat tacacatata ttttggaagt ctttggtcca       360
ttaccagctt ttgtacgagt ctgggtggaa ctcctcataa tacgccctgc agctactgct       420
gtgatatccc tggcatttgg acgctacatt ctggaaccat ttttattca atgtgaaatc       480
cctgaacttg cgatcaagct cattacagct gtgggcataa ctgtagtgat ggtcctaaat       540
agcatgagtg tcagctggag cgcccggatc cagatttct taaccttttg caagctcaca       600
```

-continued

| | |
|---|---|
| gcaattctga taattatagt ccctggagtt atgcagctaa ttaaaggtca aacgcagaac | 660 |
| tttaaagacg ccttttcagg aagagattca agtattacgc ggttgccact ggcttttat | 720 |
| tatggaatgt atgcatatgc tggctggttt tacctcaact ttgttactga agaagtagaa | 780 |
| aaccctgaaa acagtgacct tttctgagcg gctactggga aatttctcat tagcagttcc | 840 |
| gatctttgtt gccctctcct gctttggctc catgaacggt ggtgtgtttg ccacccttg | 900 |
| acaatgataa tgctcttctc tggagacctc gacagtcttt tgaatttcct cagttttgcc | 960 |
| aggtggcttt ttattgggct ggcagttgct gggctgattt atcttcgata caaatgccca | 1020 |
| gatatgcatc gtccttcaa ggtgccactg ttcatcccag ctttgttttc cttcacatgc | 1080 |
| ctcttcatgg ttgcccttc cctctattcg gacccattta gtacagggat tggcttcgtc | 1140 |
| atcactctga ctggagtccc tgcgtattat ctctttatta tatgggacaa gaaacccagg | 1200 |
| tggtttagaa taatgtcaga gaaaataacc agaacattac aaataatact ggaagttgta | 1260 |
| ccagaagaag ataagttatg a | 1281 |

<210> SEQ ID NO 33
<211> LENGTH: 800
<212> TYPE: DNA
<213> ORGANISM: Artificial Sequence
<220> FEATURE:
<223> OTHER INFORMATION: GFP-3xFLAG

<400> SEQUENCE: 33

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaaggat | 720 |
| tataaagatc atgatggcga ttataaagat catgatattg attataaaga tgatgatgat | 780 |
| aaataatagt gagcggccgc | 800 |

<210> SEQ ID NO 34
<211> LENGTH: 1196
<212> TYPE: DNA
<213> ORGANISM: Artificial Sequence
<220> FEATURE:
<223> OTHER INFORMATION: LUC7L-3xFLAG

<400> SEQUENCE: 34

| | |
|---|---|
| atgtccgccc aggcgcagat gcgggccctg ctggaccagc tcatgggcac ggctcgggac | 60 |
| ggagacgaaa ccagacagag ggtcaagttt acagatgacc gtgtctgcaa gagtcacctt | 120 |
| ctggactgct gccccatga catcctggct gggacgcgca tggatttagg agaatgtacc | 180 |
| aaaatccacg acttggccct ccgagcagat tatgagattg caagtaaaga aagagacctg | 240 |

-continued

```
tttttttgaat tagatgcaat ggatcacttg gagtcctttta ttgctgaatg tgatcggaga      300
actgagctcg ccaagaagcg gctggcagaa acacaggagg aaatcagtgc ggaagtttct      360
gcaaaggcag aaaaagtaca tgagttaaat aagaaatag gaaaactcct tgctaaagcc       420
gaacagctag gggctgaagg taatgtggat gaatcccaga agattcttat ggaagtggaa      480
aaagttcgtg cgaagaaaaa agaagctgag gaagaataca gaaattccat gcctgcatcc      540
agttttcagc agcaaaagct gcgtgtctgc gaggtctgtt cagcctacct tggtctccat      600
gacaatgacc gtcgcctggc agaccacttc ggtggcaagt tacacttggg gttcattcag      660
atccgagaga agcttgatca gttgaggaaa actgtcgctg aaaagcagga aagagaaat      720 caggatcgct tgaggaggag agaggagagg gaacgggagg agcgtctgag caggaggtcg      780
ggatcaagaa ccagagatcg caggaggtca cgctcccggg atcggcgtcg gaggcggtca      840
agatctacct cccgagagcg acggaaattg tcccggtccc ggtcccgaga tagacatcgg      900
cgccaccgca gccgttcccg gagccacagc cggggacatc gtcgggcttc ccgggaccga      960
agtgcgaaat acaagttctc cagagagcgg gcatccagag aggagtcctg ggagagcggg     1020
cggagcgagc gagggccccc ggactggagg cttgagagct ccaacgggaa gatggcttca     1080
cggaggtcag aagagaagga ggccggcgag atcgattata aagatcatga tggcgattat     1140
aaagatcatg atattgatta taaagatgat gatgataaat aatagtgagc ggccgc        1196
```

<210> SEQ ID NO 35
<211> LENGTH: 1260
<212> TYPE: DNA
<213> ORGANISM: Artificial Sequence
<220> FEATURE:
<223> OTHER INFORMATION: LUC7L2-3xFLAG

<400> SEQUENCE: 35

```
atgtcggcgc aggcccagat gcgcgcgatg ctggaccagt tgatgggcac ctcccgggac       60
ggagatacaa ctcgtcaacg aatcaaattc agtgatgaca gagtatgcaa gagtcaccttt     120 ctcaactgtt gtcctcatga tgtccttttct ggaactagaa tggatcttgg agaatgtctg    180
aaagtccatg acctggcttt aagagcggat tatgaaattg catccaaaga acaagatttt     240
ttctttgaac ttgatgccat ggatcatctg cagtcattca ttgcagattg tgatcgtaga     300
acagaagtgg ccaagaaaag attagcagaa actcaagaag agattagtgc tgaagtagca    360
gcaaaggcag aacgtgttca tgagttaaat aagaaattg gtaaattgtt agccaaggtg     420
gaacaactag gagctgaagg aatgtggag gaatcccaga agtaatgga tgaagtagag      480 aaagcacggg caaagaaaag agaagcagag gaagtttatc ggaattctat gccagcttcc    540
agttttcagc agcagaaact tcgagtctgt gaagtctgct ctgcctattt aggacttcat    600
gataatgaca cacgactggc tgatcatttt ggggtaaac tgcacctggg atttattgaa     660
ataagagaga agcttgaaga attaaagaga gtcgtagctg agaagcagga aaagaaac      720 caggaacggc tgaaacgaag agaagagaga gagagagaag aagggagaa gctgaggagg    780 tcccgatcac acagcaagaa tccaaaaaga tccaggtcca gagagcatcg cagacatcga    840
tctcgctcca tgtcacgtga acgcaagagg agaactcgat ccaaatctcg ggagaaacgc    900
catcgccaca ggtcccgctc cagcagccgt agccgcagcc gtagccacca gagaagtcgg    960
cacagttcta gagataggag cagagaacga tccaagagga gatcctcaaa agaaagattc   1020
agagaccaag acttagcatc atgtgacaga gacaggagtt caagagacag atcacctcgt    1080
```

```
gacagagatc ggaaagataa aagcggtcc tatgagagtg ctaatggcag atcagaagac      1140
aggaggagct ctgaagagcg cgaagcaggg gagatcggag ggggtgatta taaagatcat      1200
gatggcgatt ataagatca tgatattgat tataaagatg atgatgataa ataatagtga      1260
```

<210> SEQ ID NO 36
<211> LENGTH: 1379
<212> TYPE: DNA
<213> ORGANISM: Artificial Sequence
<220> FEATURE:
<223> OTHER INFORMATION: LUC7L3-3xFLAG

<400> SEQUENCE: 36

```
atgatttcgg ccgcgcagtt gttggatgag ttaatgggcc gggaccgaaa cctagccccg        60
gacgagaagc gcagcaacgt gcggtgggac cacgagagcg tttgtaaata ttatctctgt      120 ggttttttgtc ctgcggaatt gttcacaaat acacgttctg atcttggtcc gtgtgaaaaa      180
attcatgatg aaaatctacg aaaacagtat gagaagagct ctcgtttcat gaaagttggc      240
tatgagagag atttttttgcg atacttacag agcttacttg cagaagtaga acgtaggatc      300
agacgaggcc atgctcgttt ggcattatct caaaaccagc agtcttctgg ggccgctggc      360
ccaacaggca aaaatgaaga aaaaattcag gttctaacag acaaaattga tgtacttctg      420
caacagattg aagaattagg gtctgaagga aaagtagaag aagcccaggg gatgatgaaa      480
ttagttgagc aattaaaaga agagagagaa ctgctaaggt ccacaacgtc gacaattgaa      540
agctttgctg cacaagaaaa acaaatggaa gtttgtgaag tatgtggagc ctttttaata      600
gtaggagatg cccagtcccg ggtagatgac catttgatgg aaaacaaca catgggctat      660 gccaaaatta aagctactgt agaagaatta aagaaaagt taaggaaaag aaccgaagaa      720
cctgatcgtg atgagcgtct aaaaaggag aagcaagaaa gagaagaaag agaaaaagaa      780
cgggagagag aaaggggaaga aagagaaagg aaaagacgaa gggaagagga gaaagagaa      840 aaagaaaggg ctcgtgacag agaaagaaga aagagaaagtc gttcacgaag tagacactca      900
agccgaacat cagacagaag atgcagcagg tctcgggacc acaaaaggtc acgaagtaga      960
gaaagaaggc ggagcagaag tagagatcga cgaagaagca gaagccatga tcgatcagaa     1020
agaaaacaca gatctcgaag tcgggatcga agaagatcaa aagccggga tcgaaagtca     1080 tataagcaca ggagcaaaag tcgggacaga gaacaagata gaaaatccaa ggagaaagaa     1140 aagagggga ctgatgataa aaaaagtagt gtgaagtccg gtagtcgaga aaagcagagt     1200
gaagacacaa acactgaatc gaaggaaagt gatactaaga atgaggtcaa tgggaccagt     1260
gaagacatta aatctgaagg tgacactcag tccaatgatt ataaagatca tgatggcgat     1320
tataaagatc atgatattga ttataaagat gatgatgata ataatagtg agcggccgc       1379
```

<210> SEQ ID NO 37
<211> LENGTH: 1539
<212> TYPE: DNA
<213> ORGANISM: Artificial Sequence
<220> FEATURE:
<223> OTHER INFORMATION: SLC7A11-HA

<400> SEQUENCE: 37

```
atggtcagaa agcctgttgt gtccaccatc tccaaaggag gttacctgca gggaaatgtt        60
aacgggaggc tgccttccct gggcaacaag gagccacctg gcaggagaa agtgcagctg      120 aagaggaaag tcacttttact gaggggagtc tccattatca ttggcaccat cattggagca      180
ggaatcttca tctctcctaa gggcgtgctc cagaacacgg gcagcgtggg catgtctctg      240
```

| | |
|---|---|
| accatctgga cggtgtgtgg ggtcctgtca ctatttggag ctttgtctta tgctgaattg | 300 |
| ggaacaacta taaagaaatc tggaggtcat tacacatata ttttggaagt ctttggtcca | 360 |
| ttaccagctt ttgtacgagt ctgggtggaa ctcctcataa tacgccctgc agctactgct | 420 |
| gtgatatccc tggcatttgg acgctacatt ctggaaccat tttttattca atgtgaaatc | 480 |
| cctgaacttg cgatcaagct cattacagct gtgggcataa ctgtagtgat ggtcctaaat | 540 |
| agcatgagtg tcagctggag cgcccgaatc cagattttct taaccttttg caagctcaca | 600 |
| gcaattctga taattatagt ccctggagtt atgcagctaa ttaaaggtca aacgcagaac | 660 |
| tttaaagacg cctttcagg aagagattca agtattacgc ggttgccact ggctttttat | 720 |
| tatggaatgt atgcatatgc tggctggttt tacctcaact ttgttactga agaagtagaa | 780 |
| aaccctgaaa aaaccattcc ccttgcaata tgtatatcca tggccattgt caccattggc | 840 |
| tatgtgctga caaatgtggc ctactttacg accattaatg ctgaggagct gctgctttca | 900 |
| aatgcagtgg cagtgacctt ttctgagcgg ctactgggaa atttctcatt agcagttccg | 960 |
| atctttgttg ccctctcctg ctttggctcc atgaacggtg gtgtgtttgc tgtctccagg | 1020 |
| ttattctatg ttgcgtctcg agagggtcac cttccagaaa tcctctccat gattcatgtc | 1080 |
| cgcaagcaca ctcctctacc agctgttatt gttttgcacc ctttgacaat gataatgctc | 1140 |
| ttctctggag acctcgacag tcttttgaat ttcctcagtt ttgccaggtg gcttttatt | 1200 |
| gggctggcag ttgctgggct gatttatctt cgatacaaat gcccagatat gcatcgtcct | 1260 |
| ttcaaggtgc cactgttcat cccagctttg ttttccttca catgcctctt catggttgcc | 1320 |
| ctttccctct attcggaccc atttagtaca gggattggct tcgtcatcac tctgactgga | 1380 |
| gtccctgcgt attatctctt tattatatgg gacaagaaac ccaggtggtt tagaataatg | 1440 |
| tcagagaaaa taaccagaac attacaaata atactggaag ttgtaccaga agaagataag | 1500 |
| ttatatccat atgatgttcc agattatgct taatagtga | 1539 |

<210> SEQ ID NO 38
<211> LENGTH: 2349
<212> TYPE: DNA
<213> ORGANISM: Homo sapiens

<400> SEQUENCE: 38

| | |
|---|---|
| atgacccatg aagagcacca tgcagccaaa accctgggga ttggcaaagc cattgctgtc | 60 |
| ttaacctctg gtggagatgc ccaaggtatg aatgctgctg tcagggctgt ggttcgagtt | 120 |
| ggtatcttca ccggtgcccg tgtcttcttt gtccatgagg ttatcaagg cctggtggat | 180 |
| ggtggagatc acatcaagga agccacctgg gagagcgttt cgatgatgct tcagctggga | 240 |
| ggcacggtga ttggaagtgc ccggtgcaag gactttcggg aacgagaagg acgactccga | 300 |
| gctgcctaca acctggtgaa gcgtgggatc accaatctct gtgtcattgg gggtgatgc | 360 |
| agcctcactg gggctgacac cttccgttct gagtggagtg acttgttgag tgacctccag | 420 |
| aaagcaggta agatcacaga tgaggaggct acgaagtcca gctacctgaa cattgtgggc | 480 |
| ctggttgggt caattgacaa tgacttctgt ggcaccgata tgaccattgg cactgactct | 540 |
| gcccctgcatc ggatcatgga aattgtagat gccatcacta ccactgccca gagccaccag | 600 |
| aggacatttg tgttagaagt aatgggccgc cactgtggat acctggccct tgtcacctct | 660 |
| ctgtcctgtg gggccgactg gttttttatt cctgaatgtc caccagatga cgactgggag | 720 |
| gaacaccttt gtcgccgact cagcgagaca aggacccgtg gttctcgtct caacatcatc | 780 |

```
attgtggctg agggtgcaat tgacaagaat ggaaaaccaa tcacctcaga agacatcaag      840
aatctggtgg ttaagcgtct gggatatgac acccgggtta ctgtcttggg gcatgtgcag      900
aggggtggga cgccatcagc ctttgacaga attctgggca gcaggatggg tgtggaagca      960
gtgatggcac ttttggaggg gacccccagat accccagcct gtgtagtgag cctctctggt   1020
aaccaggctg tgcgcctgcc cctcatggaa tgtgtccagg tgaccaaaga tgtgaccaag   1080
gccatggatg agaagaaatt tgacgaagcc ctgaagctga gaggccggag cttcatgaac   1140
aactgggagg tgtacaagct tctagctcat gtcagacccc cggtatctaa gagtggttcg   1200
cacacagtgg ctgtgatgaa cgtggggggct ccggctgcag gcatgaatgc tgctgttcgc   1260
tccactgtga ggattggcct tatccagggc aaccgagtgc tcgttgtcca tgatggtttc   1320
gagggcctgg ccaaggggca gatagaggaa gctggctgga gctatgttgg gggctggact   1380
ggccaaggtg gctctaaact tgggactaaa aggactctac ccaagaagag ctttgaacag   1440
atcagtgcca ataactaa gtttaacatt cagggccttg tcatcattgg gggctttgag   1500
gcttacacag ggggcctgga actgatggag ggcaggaagc agtttgatga gctctgcatc   1560
ccatttgtgg tcattcctgc tacagtctcc aacaatgtcc ctggctcaga cttcagcgtt   1620
ggggctgaca cagcactcaa tactatctgc acaacctgtg accgcatcaa gcagtcagca   1680
gctggcacca agcgtcgggt gtttatcatt gagactatgg gtggctactg tggctacctg   1740
gctaccatgg ctggactggc agctgggggcc gatgctgcct acatttttga ggagcccttc   1800
accattcgag acctgcaggc aaatgttgaa catctggtgc aaaagatgaa aacaactgtg   1860
aaaaggggct tggtgttaag gaatgaaaag tgcaatgaga actataccac tgacttcatt   1920
ttcaacctgt actctgagga ggggaagggc atcttcgaca gcaggaagaa tgtgcttggt   1980
cacatgcagc agggtgggag cccaaccccca tttgatagga attttgccac taagatgggc   2040
gccaaggcta tgaactggat gtctgggaaa atcaaagaga gttaccgtaa tgggcggatc   2100
tttgccaata ctccagattc gggctgtgtt ctggggatgc gtaagagggc tctggtcttc   2160
caaccagtgg ctgagctgaa ggaccagaca gattttgagc atcgaatccc caaggaacag   2220
tggtggctga aactgaggcc catcctcaaa atcctagcca agtacgagat tgacttggac   2280
acttcagacc atgcccacct ggagcacatc acccggaagc ggtccgggga agcggccgtc   2340
taatagtga                                                                                    2349
```